US008702774B2

(12) United States Patent  
Baker et al.

(10) Patent No.: US 8,702,774 B2  
(45) Date of Patent: Apr. 22, 2014

(54) DEVICE, SYSTEM AND METHOD OF REMOVING HEAT FROM SUBCUTANEOUS LIPID-RICH CELLS

(75) Inventors: Mark Baker, Livermore, CA (US); Joseph Coakley, Dublin, CA (US); Paul William Martens, Pleasanton, CA (US); Albert L. Ollerdessen, Danville, CA (US); William Patrick Pennybacker, Livermore, CA (US); Jesse Nicasio Rosen, Albany, CA (US); Peter Yee, San Ramon, CA (US); John W. Allison, Los Altos, CA (US); Bryan Weber, Livermore, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 628 days.

(21) Appl. No.: 12/772,040

(22) Filed: Apr. 30, 2010

(65) Prior Publication Data

US 2010/0280582 A1 Nov. 4, 2010

Related U.S. Application Data

(60) Provisional application No. 61/174,487, filed on Apr. 30, 2009.

(51) Int. Cl.  
*A61F 7/00* (2006.01)

(52) U.S. Cl.  
USPC .............. 607/96; 607/104; 607/108; 607/112

(58) Field of Classification Search  
USPC .................................... 607/96, 104, 108, 112  
See application file for complete search history.

(56) References Cited

U.S. PATENT DOCUMENTS

| 681,806 A | 9/1901 | Mignault |
|---|---|---|
| 889,810 A | 6/1908 | Robinson |
| 2,516,491 A | 7/1950 | Swastek |
| 2,766,619 A | 10/1956 | Tribus et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |

(Continued)

FOREIGN PATENT DOCUMENTS

| CN | 1511503 | 7/2004 |
|---|---|---|
| CN | 1741777 A | 3/2006 |

(Continued)

OTHER PUBLICATIONS

U.S. Appl. No. 12/275,002, filed Nov. 20, 2008, Martens.

(Continued)

*Primary Examiner* — Linda Dvorak  
*Assistant Examiner* — Kaitlyn Smith  
(74) *Attorney, Agent, or Firm* — Perkins Coie LLP

(57) ABSTRACT

Devices, systems and methods for removing heat from subcutaneously disposed lipid-rich cells are disclosed. In selected embodiments, suction and/or heat removal sources are coupled to an applicator. The applicator includes a flexible portion and a rigid portion. The rigid portion includes a thermally conductive plate and a frame coupling the thermally conductive plate and the flexible portion. An interior cavity of the applicator is in fluid communication with the suction source, and the frame maintains contiguous engagement between the heat removal source and the thermally conductive plate.

32 Claims, 31 Drawing Sheets

(56) References Cited

U.S. PATENT DOCUMENTS

| | | |
|---|---|---|
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,002,221 A | 1/1977 | Buchalter |
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,362,966 A | 11/1994 | Rosenthal et al. |
| 5,363,347 A | 11/1994 | Nguyen |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Gonçalves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,049,927 A | 4/2000 | Thomas et al. |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,150,148 A | 11/2000 | Nanda et al. |
| 6,180,867 B1 | 1/2001 | Hedengren et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |

(56) References Cited

U.S. PATENT DOCUMENTS

| | | |
|---|---|---|
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,548,297 B1 | 4/2003 | Kuri-Harcuch et al. |
| 6,551,255 B2 | 4/2003 | Van Bladel et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,697,670 B2 | 2/2004 | Chomenky et al. |
| 6,699,237 B2 * | 3/2004 | Weber et al. ................. 606/2 |
| 6,699,266 B2 | 3/2004 | Lachenbruch et al. |
| 6,718,785 B2 | 4/2004 | Bieberich |
| 6,741,895 B1 | 5/2004 | Gafni et al. |
| 6,746,474 B2 | 6/2004 | Saadat |
| 6,749,624 B2 | 6/2004 | Knowlton |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,892,099 B2 | 5/2005 | Jaafar et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,347,855 B2 | 3/2008 | Eshel et al. |
| 7,367,341 B2 | 5/2008 | Anderson et al. |
| 7,713,266 B2 | 5/2010 | Elkins et al. |
| 7,854,754 B2 | 12/2010 | Ting et al. |
| RE42,277 E | 4/2011 | Jaafar et al. |
| 7,938,824 B2 | 5/2011 | Chornenky et al. |
| RE42,835 E | 10/2011 | Chornenky et al. |
| RE43,009 E | 12/2011 | Chornenky et al. |
| 8,133,191 B2 | 3/2012 | Rosenberg et al. |
| 8,192,474 B2 | 6/2012 | Levinson |
| 8,275,442 B2 | 9/2012 | Allison |
| 8,337,539 B2 | 12/2012 | Ting et al. |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0103520 A1 | 8/2002 | Latham |
| 2002/0117293 A1 | 8/2002 | Campbell |
| 2002/0120315 A1 | 8/2002 | Furuno et al. |
| 2002/0128648 A1 * | 9/2002 | Weber et al. ................. 606/45 |
| 2002/0151887 A1 | 10/2002 | Stern et al. |
| 2002/0188286 A1 | 12/2002 | Quijano et al. |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0199226 A1 | 10/2003 | Sommer et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0176667 A1 | 9/2004 | Mihai et al. |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0259855 A1 | 12/2004 | Anderson et al. |
| 2005/0049661 A1 | 3/2005 | Koffroth |
| 2005/0143781 A1 * | 6/2005 | Carbunaru et al. ........ 607/11 |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0036300 A1 | 2/2006 | Kreindel |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0122509 A1 | 6/2006 | Desilets |
| 2006/0200063 A1 | 9/2006 | Munro et al. |
| 2006/0206110 A1 | 9/2006 | Knowlton et al. |
| 2006/0234899 A1 | 10/2006 | Nekmard et al. |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0055173 A1 | 3/2007 | DeLonzor et al. |
| 2007/0078502 A1 | 4/2007 | Weber et al. |
| 2007/0106342 A1 * | 5/2007 | Schumann ................. 607/46 |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |

(56) References Cited

U.S. PATENT DOCUMENTS

| | | |
|---|---|---|
| 2008/0046047 A1 | 2/2008 | Jacobs |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0140371 A1 | 6/2008 | Warner |
| 2008/0183164 A1 | 7/2008 | Elkins et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0281464 A1* | 11/2009 | Cioanta et al. .................. 601/2 |
| 2009/0312676 A1 | 12/2009 | Rousso et al. |
| 2010/0028969 A1 | 2/2010 | Mueller et al. |
| 2010/0081971 A1 | 4/2010 | Allison |
| 2011/0009860 A1 | 1/2011 | Chornenky et al. |
| 2011/0077723 A1 | 3/2011 | Parish et al. |
| 2011/0112405 A1* | 5/2011 | Barthe et al. .................. 600/459 |
| 2011/0196438 A1 | 8/2011 | Mnozil et al. |
| 2012/0016239 A1* | 1/2012 | Barthe et al. .................. 600/439 |
| 2012/0022518 A1 | 1/2012 | Levinson |
| 2012/0035475 A1* | 2/2012 | Barthe et al. .................. 600/439 |
| 2012/0035476 A1* | 2/2012 | Barthe et al. .................. 600/439 |
| 2012/0046547 A1* | 2/2012 | Barthe et al. .................. 600/439 |
| 2012/0053458 A1* | 3/2012 | Barthe et al. .................. 600/439 |
| 2012/0101549 A1* | 4/2012 | Schumann ....................... 607/46 |
| 2012/0239123 A1 | 9/2012 | Weber et al. |
| 2013/0066309 A1 | 3/2013 | Levinson |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0303904 A1* | 11/2013 | Barthe et al. .................. 600/439 |
| 2013/0303905 A1* | 11/2013 | Barthe et al. .................. 600/439 |

FOREIGN PATENT DOCUMENTS

| | | |
|---|---|---|
| CN | 1817990 A | 8/2006 |
| DE | 532976 C | 9/1931 |
| DE | 2851602 | 6/1980 |
| DE | 4213584 A1 | 11/1992 |
| DE | 4224595 | 1/1994 |
| EP | 0263069 A2 | 4/1988 |
| EP | 0397043 | 11/1990 |
| EP | 0406244 A1 | 1/1991 |
| EP | 0598824 A1 | 6/1994 |
| EP | 1201266 | 5/2002 |
| FR | 2745935 | 9/1997 |
| GB | 2286660 A | 8/1995 |
| GB | 2323659 A | 9/1998 |
| JP | S6282977 | 4/1987 |
| JP | 63076895 A | 4/1988 |
| JP | 03051964 | 3/1991 |
| JP | 3259975 A | 11/1991 |
| JP | 4093597 A | 3/1992 |
| JP | 7194666 | 8/1995 |
| JP | 7268274 A | 10/1995 |
| JP | 09164163 A | 6/1997 |
| JP | 10216169 A | 8/1998 |
| JP | 2000503154 | 3/2000 |
| JP | 3065657 | 7/2000 |
| JP | 2002224051 | 8/2002 |
| JP | 2002543668 | 12/2002 |
| JP | 2004013600 | 1/2004 |
| JP | 2004073812 | 11/2004 |
| JP | 2005039790 | 2/2005 |
| JP | 3655820 | 3/2005 |
| JP | 200565984 | 3/2005 |
| JP | 2005110755 | 4/2005 |
| JP | 2005520608 T | 7/2005 |
| JP | 2008323716 | 11/2005 |
| JP | 2006026001 A | 2/2006 |
| JP | 2006520949 | 9/2006 |
| JP | 2008532591 | 8/2008 |
| KR | 1020040094508 | 11/2004 |
| SU | 532976 A1 | 11/1978 |
| TW | 0476644 | 2/2002 |
| WO | WO-8503216 | 8/1985 |
| WO | WO-94/04116 | 3/1994 |
| WO | WO-9404116 | 3/1994 |
| WO | WO-96/36293 | 11/1996 |
| WO | WO-96/37158 | 11/1996 |
| WO | WO-9636293 A1 | 11/1996 |
| WO | WO-9637158 A1 | 11/1996 |
| WO | WO-97/05828 | 2/1997 |
| WO | WO-9705828 A1 | 2/1997 |
| WO | WO-9722262 | 6/1997 |
| WO | WO-9722262 A2 | 6/1997 |
| WO | WO-9725798 | 7/1997 |
| WO | WO-98/41157 | 9/1998 |
| WO | WO-9841156 A1 | 9/1998 |
| WO | WO-9841157 A1 | 9/1998 |
| WO | WO-9938469 | 8/1999 |
| WO | WO-9938469 A1 | 8/1999 |
| WO | WO-0044346 A1 | 8/2000 |
| WO | WO-00/65770 | 11/2000 |
| WO | WO-0067685 | 11/2000 |
| WO | WO-0114012 | 3/2001 |
| WO | WO-0205736 A2 | 1/2002 |
| WO | WO-02102921 A1 | 12/2002 |
| WO | WO-03007859 A1 | 1/2003 |
| WO | WO-03078596 A2 | 9/2003 |
| WO | WO-04000098 A2 | 12/2003 |
| WO | WO-2004080279 A2 | 9/2004 |
| WO | WO-2004090939 | 10/2004 |
| WO | WO-2005033957 | 4/2005 |
| WO | WO-2005046540 A1 | 5/2005 |
| WO | WO-2005096979 | 10/2005 |
| WO | WO-2006/066226 | 6/2006 |
| WO | WO-2006066226 A1 | 6/2006 |
| WO | WO-2006094348 | 9/2006 |
| WO | WO-2006106836 | 10/2006 |
| WO | WO-2006127467 A2 | 11/2006 |
| WO | WO-2007012083 | 1/2007 |
| WO | WO-2007041642 A2 | 4/2007 |
| WO | WO-2007127924 | 11/2007 |
| WO | WO-2008039557 | 4/2008 |
| WO | WO-2008143678 | 11/2008 |
| WO | WO-2009/011708 | 1/2009 |
| WO | WO-2009026471 | 2/2009 |
| WO | WO-2010077841 | 7/2010 |
| WO | WO-2010127315 A2 | 11/2010 |
| WO | WO2012012296 | 1/2012 |
| WO | WO-2012103242 | 8/2012 |

OTHER PUBLICATIONS

U.S. Appl. No. 12/275,014, filed Nov. 20, 2008, Martens.
U.S. Appl. No. 12/337,544, filed Dec. 17, 2008, Alison.
Ardevol, "Cooling rates of tissue samples during freezing with liquid nitrogen," J. of Biochem and Biophysical Methods, 27, 77-86 (1993).
Bohm et al., "Saline-enhanced radiofrequency ablation of breast tissue: an in vitro feasibility study," Invest Radiol, 2000, pp. 149-157, vol. 35—issue (3).
Bondei, E. et al., "Disorders of Subcutaneous Tissue (Cold Panniculitis)," Dermatology in General Medicine, Chapter 108, Section 16: 1333-1334, 1993.
Burge, S.M. et al., "Hair Follicle Destruction and Regeneration in Guinea Pig Skin after Cutaneous Freeze Injury," Cryobiology, 27(2): 153-163, 1990.
Coban, "Ischemia-Reperfusion Injury of Adipofascial Tissue: An Experimental Study Evaluating early Histologic and Biochemical Alterations in Rats," Mediators of Inflammation, 2005, 5, 304-308.
Donski et al., "The Effects of Cooling no Experimental Free Flap Survival," Brit J Plas Surg, 1980, pp. 353-360, vol. 33.
Duncan, W.C. et al., "Cold Panniculitis," Arch. Derm., 94:722-24, 1966.

(56) References Cited

OTHER PUBLICATIONS

Epstein, E.H. et al., "Popsicle Panniculitis," The New England Journal of Medicine, 282(17):996-67, 1970.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
Gage, "Current Progress in Cryosurgery," Cryobiology 25, 483-486 (1988).
Hale et al., "Influence of chronic heat exposure and prolonged food deprivation on execretion of mahnesium, phosphorus, calcium, hydrogen ion & ketones," Aerosp Med. 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).
International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2007/062508; Applicant: Juniper Medical, Inc.; Date of Mailing: Jul. 20, 2007, 13 pages.
International Search Report and Written Opinion for PCT/US2009/058088; Applicant: Zeltiq Aesthetics, Inc.; Date of Mailing: Nov. 20, 2009, 14 pages.
International Search Report and Written Opinion for PCT/US2009/067973; Applicant: Zeltiq Aesthetics, Inc.; Date of Mailing: Feb. 18, 2010, 10 pages.
International Search Report for EP07758558.6; Applicant: Zeltiq Aesthetics, Inc.; Mailed on Jul. 20, 2007, 4 pages.
International Search Report and Written Opinion for PCT/US2005/045988; Applicant: The General Hospital Corporation; Mailed on Apr. 25, 2006, 14 pages.
Kellum, R.E. et al., "Sclerema Neonatorum: Report of Case and Analysis of Subcutaneous and Epidermal-Dermal Lipids by Chromatographic Methods," Arch. Derm., 97:372-80, 1968.

Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Moschella, S.L. et al., "Diseases of the Subcutaneous Tissue," Derm., Section 2:1169-1181, 1985.
Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis—a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 10/391,221; Date of Mailing: Jul. 22, 2005, 6 pages.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 11/016,196; Date of Mailing: Sep. 25, 2009, 8 pages.
Non-Final Office Action; U.S. Appl. No. 11/016,196; Date of Mailing: Apr. 22, 2008, 11 pages.
Non-Final Office Action; U.S. Appl. No. 11/359,092; Date of Mailing: Nov. 19, 2009, 13 pages.
Non-Final Office Action; U.S. Appl. No. 11/435,502; Date of Mailing: Jul. 17, 2009, 10 pages.
Non-Final Office Action; U.S. Appl. No. 11/528,225; Date of Mailing: Apr. 12, 2010, 11 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department

(56) References Cited

OTHER PUBLICATIONS of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Pre-Interview Office Action; U.S. Appl. No. 11/434,478; Date of Mailing: May 6, 2010, 4 pages.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2:59-71.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells," J. Tiss. Cult. Meth., 14:85-92, 1992.
Non-Final Office Action; U.S. Appl. No. 11/558,046; Date of Mailing: Jul. 12, 2010, 14 pages.
Non-Final Office Action; U.S. Appl. No. 11/741,271; Date of Mailing: Jul. 12, 2010, 9 pages.
International Search Report and Written Opinion for PCT/US2010/033290; Applicant: Zeltiq Aesthetics, Inc.; Mailed on Feb. 25, 2011, 12 pages.
International Search Report and Written Opinion for PCT/US2011/022112; Applicant: Zeltiq Aesthetics, Inc.; Mailed on Mar. 18, 2011, 11 pages.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Wang et al., "Cryopreservation of cell/hydrogel constructs based on a new cell-assembling technique", Sep. 5, 2009, 40 pages.
Wharton et al., "Cold acclimation and cryoprotectants in a freeze-tolerant Antarctic nematode, Panagrolaimus davidi," Mar. 7, 2000, 2 pages.
European Search Report, European Patent Application No. 10167756.5, Applicant: The General Hospital Corporation, Mailing Date: Aug. 31, 2010, 6 pages.
European Search Report; Application No. EP10770461; Dated Aug. 31, 2012; Applicamt: Zeltiq Aesthetics, Inc. 5 pgs.
European Search Report, Supplement, European Patent Application No. EP09836823, Applicant: Zeltiq Aesthetics, Inc., Mailing Date: May 15, 2012, 5 pages.
Final Office Action; U.S. Appl. No. 11/741,271; Date of Mailing: Jul. 19, 2012, 8 pages.
Final Office Action; U.S. Appl. No. 11/750,953; Date of Mailing: Jul. 5, 2012, 11 pages.
International Search Report and Written Opinion for PCT/US2012/022585; Mailed on May 18, 2012, 14 pages.
Non-Final Office Action; U.S. Appl. No. 11/777,992; Date of Mailing: Jun. 22, 2012, 5 pages.
Non-Final Office Action; U.S. Appl. No. 12/337,544; Date of Mailing: Mar. 30, 2012, 13 pages.
European Search Report, Eurpean Patent Application No. EP07761461; Applicant: Zeltiq Aesthetics, Inc., Mailing Date: Apr. 25, 2012, 9 pages.
European Search Report, Supplement, European Patent Application No. EP08798416.7, Applicant: Zeltiq Aesthetics, Inc., Mailing Date: Jan. 12, 2012, 7 pages.

Final Office Action; U.S. Appl. No. 11/528,225; Date of Mailing: Dec. 29, 2010, 12 pages.
Final Office Action; U.S. Appl. No. 11/558,046; Date of Mailing: Mar. 30, 2011, 17 pages.
Non-Final Office Action; U.S. Appl. No. 12/942,852; Date of Mailing: Mar. 7, 2011, 6 pages.
International Search Report and Written Opinion for PCT/US2011/022444; Applicant: Zeltiq Aesthetics, Inc., Mailed on Mar. 29, 2011, 14 pages.
Non-Final Office Action; U.S. Appl. No. 11/528,189; Date of Mailing Apr. 6, 2012, 9 pages.
Non-Final Office Action; U.S. Appl. No. 11/528,225; Date of Mailing: Aug. 3, 2011, 13 pages.
Non-Final Office Action; U.S. Appl. No. 12/565,613; Date of Mailing: Sep. 23, 2011, 32 pages.
Non-Final Office Action; U.S. Appl. No. 12/942,852; Date of Mailing: Jun. 30, 2011, 10 pages.
Pope, "Selective Firbous Septae Heating", Thermage Article, Feb. 2005, 7pgs.
Non-Final Office Action; U.S. Appl. No. 12/840,235; Date of Mailing: Apr. 11, 2013; 9 pages.
Manstein et al. "A Novel Cryotherapy Method of Non-invasive, Selective Lipolysis" LasersSurg.Med 40:S20 p. 104 (2008).
Manstein et al."Selective Cryolysis: A Novel Method of Non-Invasive Fat Removal", LasersSurg.Med. 40:595-604 (2008).
Nagle W.A., Soloff, B.L., Moss, A.J. Jr., Henle K.J. "Cultured Chinese Hamster Cells Undergo Apoptosis After Exposure to Cold but Nonfreezing Temperatures" Cryobiology 27, 439-451 (1990).
Narins, "Non-Surgical Radiofrequency Facelift", 2003, 495-500, 6 pgs.
Mazur, P. "Cryobiology: the Freezing of Biological Systems" Science, 68: 939-949 (1970).
Rubinsky, B., "Principles of Low Temperature Preservation" Heart Failure Reviews, 8, 277-284 (2003).
Thermage, News Release, "Study Published in Facial Plastic Surgery Journal Finds Selective Heating of Fibrous Septae Key to Success and Safety of Thermage ThermoCool System", Jun. 20, 2005, 2 pages.
Vallerand, A.L., Zamecnik. J., Jones, P.J.H. Jacobs, I. "Cold Stress Increases Lipolysis, FFA RA and TG/FFA Cycling in Humans" Aviation, Space, and Environmental Medicine 70, 42-50 (1999).
"ThermaCool Monopolar Capacitive Radiofrequency",The one choice for nonabliative tissue tightening and contouring, Tech Brochure, Nov. 30, 2005, 8 pgs.
"So-Called Cellulite: An Invetnted Disease", Nurnberger, Journal Title: Journal of dermatologic surgery and oncology, Mar. 1978, 14 pgs.
"Effect of Controlled Volumetric Tissue Heating with Radiorequency on Cellulite and the Subcutaneous Tissue of the Bottocks and Thighs" Del Pino, 2006, 9 pgs.
Mayoral, "Skin Tightening with a Combined Unipolar and Bipolar Radiofrequency Device" , 2007 Journal of Drugs in Dermatology, 4 pgs.
Becker, "Local Temperature Rises Influence in Vivo Electroporation Pore Development: A Numerical Stratum Corneum Lipid Phase Transition Model", Oct. 2007, 10 pgs.
Miklavcic, "Electroporation-Based Technologies and Treatments", 2010 236:1-2, 2 pgs.
Nanda, "Studies on electroporation of thermally and chemically treated human erythrocytes", May 28, 1993 in revised form Mar. 7, 1994, 6 pgs.
BioMedical Engineering OnLine, "High-Frequency Irreversible electroporation (H-FIRE) for non-thermal ablation without muscle contraction", Nov. 21, 2011, 21 pgs.
Al-Sakere, "Tumor Ablation with Irreversible Electroporation", Nov. 2007, Issue 11, 8 pgs.

* cited by examiner

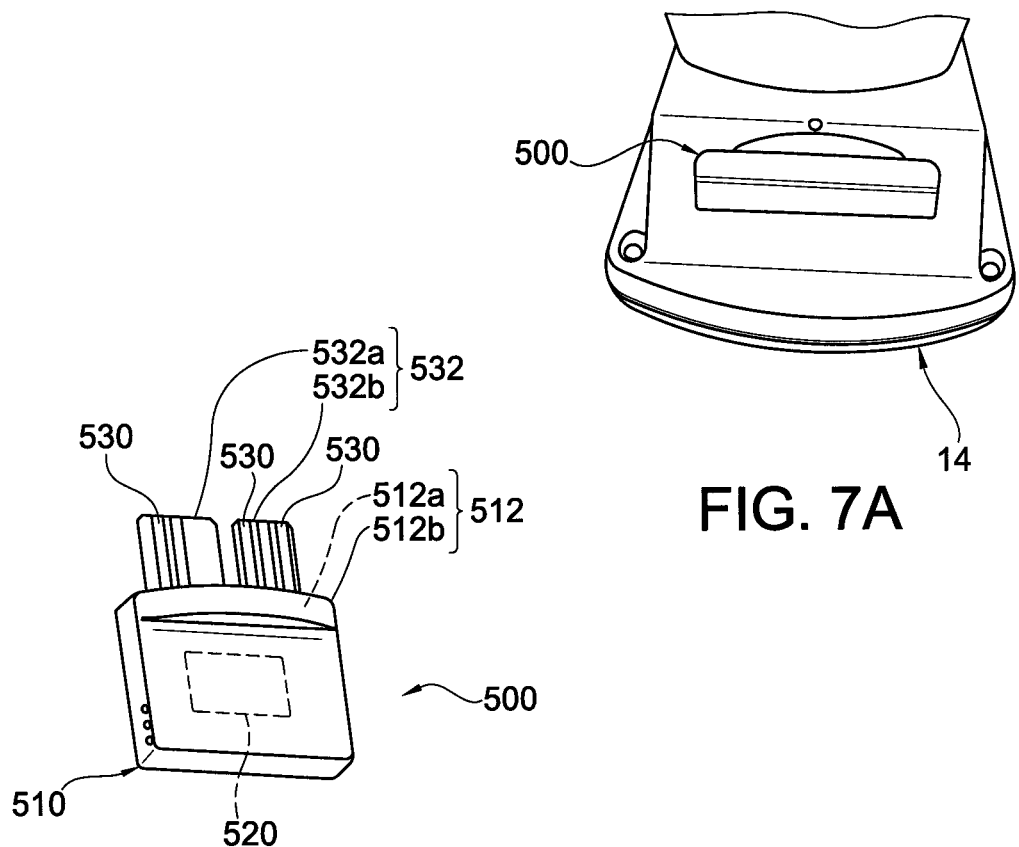
FIG. 7A
FIG. 7B
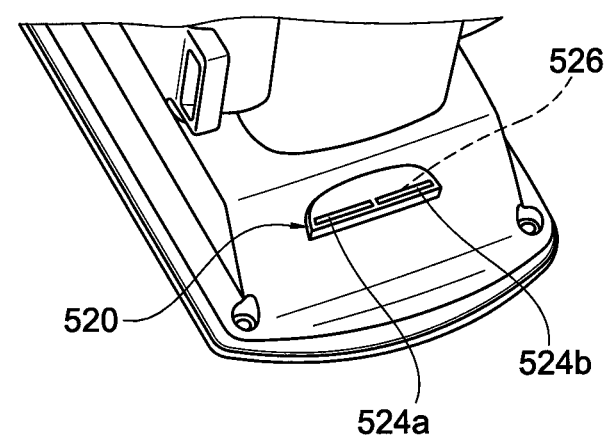
FIG. 7C

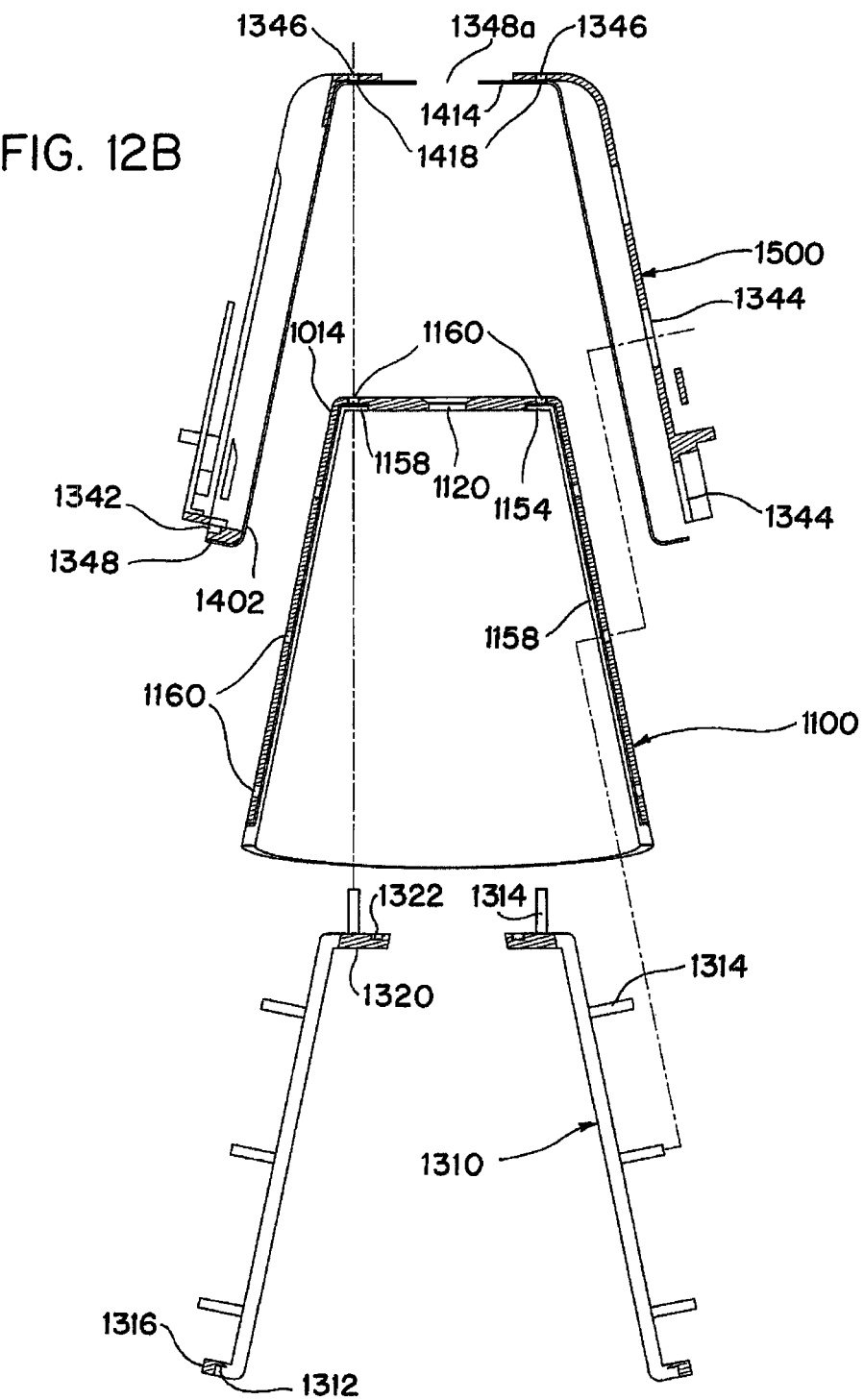

DEVICE, SYSTEM AND METHOD OF REMOVING HEAT FROM SUBCUTANEOUS LIPID-RICH CELLS

CROSS-REFERENCE TO RELATED APPLICATION(S)

This patent application claims the benefit under 35 U.S.C. §119 of U.S. Provisional Patent Application No. 61/174,487, filed on Apr. 30, 2009, entitled "Device, System and Method of Removing Heat from Subcutaneous Lipid-rich Cells." That application is incorporated herein in its entirety by reference.

INCORPORATION BY REFERENCE OF COMMONLY-OWNED APPLICATIONS

The following commonly-assigned U.S. Patent Applications are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Patent Publication No. 2007/0198071 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722 entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SUBJECT PROTECTION DEVICES";

U.S. Patent Publication No. 2009/0018623 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEM FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Patent Publication No. 2009/0149929 entitled "MONITORING THE COOLING OF SUBCUTANEOUS LIPID-RICH CELLS, SUCH AS THE COOLING OF ADIPOSE TISSUE";

U.S. Patent Publication No. 2010/0081971 entitled "TREATMENT PLANNING SYSTEMS AND METHODS FOR BODY CONTOURING APPLICATIONS";

U.S. patent application Ser. No. 12/337,544 entitled "SYSTEMS AND METHODS WITH INTERRUPT/RESUME CAPABILITIES FOR COOLING SUBCUTANEOUS LIPID-RICH CELLS";

U.S. Patent Publication No. 2008/0077202 entitled "TISSUE TREATMENT METHODS"; and U.S. Provisional Patent Application Ser. No. 61/298,175 entitled "HOME CARE METHODS AND SYSTEMS FOR REDUCING SUBCUTANEOUS FAT."

U.S. Patent Publication No. 2007/0270925 entitled "METHOD AND APPARATUS FOR NON-INVASIVELY REMOVING HEAT FROM SUBCUTANEOUS LIPID RICH CELLS INCLUDING A COOLANT HAVING A PHASE TRANSITION TEMPERATURE";

U.S. Provisional Patent Application Ser. No. 61/297,238 entitled "COMPOSITIONS FOR USE WITH A SYSTEM FOR IMPROVED COOLING OF SUBCUTANEOUS LIPID-RICH CELLS".

TECHNICAL FIELD

The present application relates generally to treatment devices, systems, and methods for removing heat from subcutaneous lipid-rich cells. In particular, several embodiments are directed toward a treatment device including a vacuum applicator to effect heat removal or extraction from subcutaneous lipid-rich cells.

BACKGROUND

Excess body fat, or adipose tissue, may be present in various locations of the body, including, for example, the thigh, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. In contrast, methods and devices for non-invasively reducing subcutaneous adipose tissue by cooling are disclosed in U.S.

Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements, and are generally selected for ease of recognition in the drawings.

FIG. 7A shows a perspective view of an embodiment of a token interfacing with the treatment device shown in FIG. 3A.

FIG. 7B shows a perspective view of the token shown in FIG. 6A.

FIG. 7C shows a perspective view of an embodiment of a receptacle for receiving the token shown in FIG. 7A.

FIG. 12B is an exploded, perspective view of an assembly of the vacuum applicator shown in FIG. 8 including the flexible portion, the first frame portions, and the subassembly shown in FIG. 12A.

DETAILED DESCRIPTION

Overview

Figure 1:
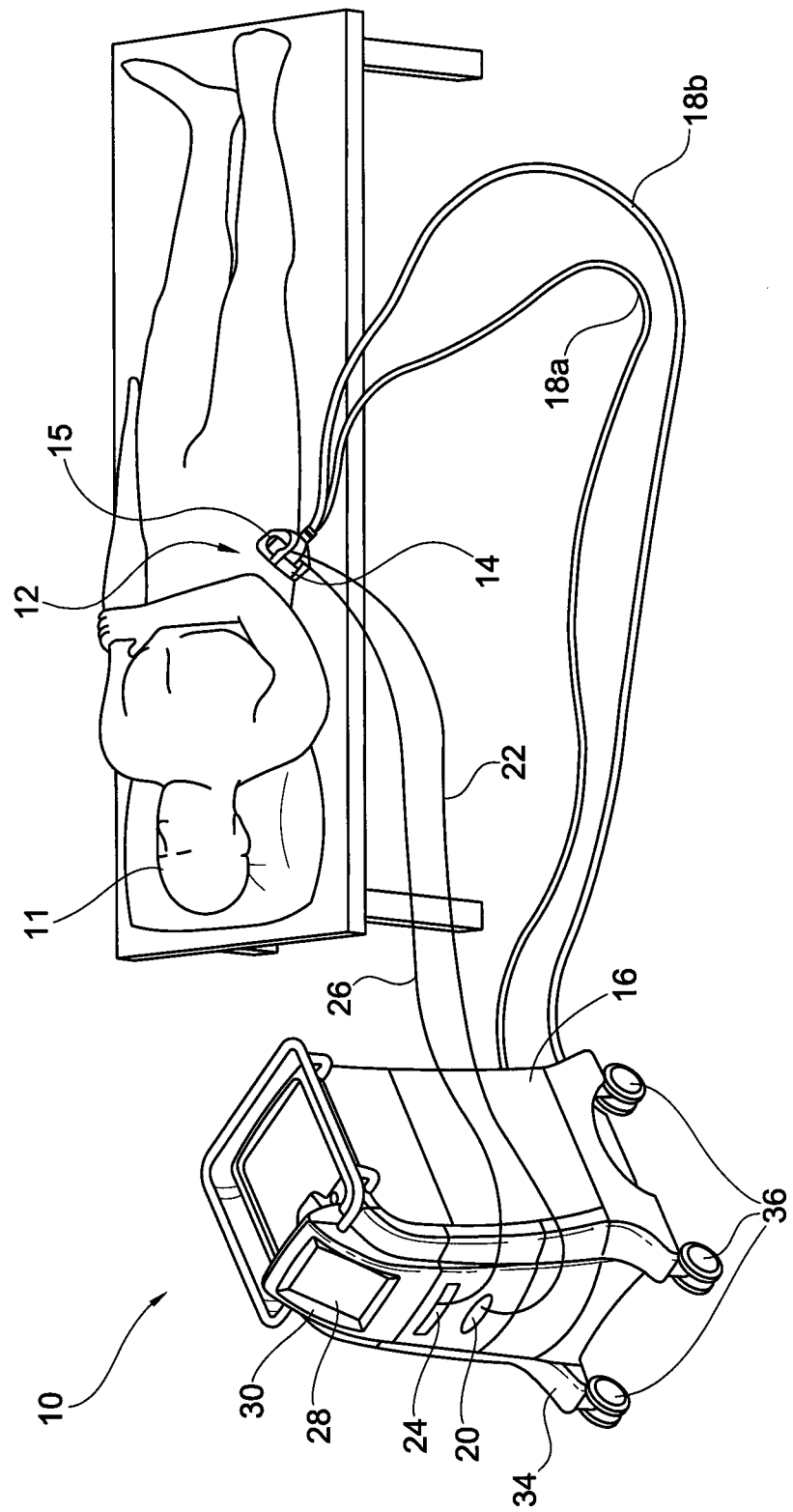
FIG. 1 is an isometric view schematically illustrating a treatment system for treating subcutaneous lipid-rich regions of a subject 11 in accordance with an embodiment of the disclosure.

Devices, systems, and methods for monitoring and closed loop controlling of the treatment (including cooling) of subcutaneous tissue, such as adipose tissue, are described. Several of the details set forth below are provided to describe the following examples and methods in a manner sufficient to enable a person skilled in the relevant art to practice, make and use them. Several of the details and advantages described below, however, may not be necessary to practice certain examples and methods of the technology. Additionally, the technology may include other examples and methods that are within the scope of the claims but are not described in detail.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Aspects of the present invention are generally directed toward a device for treating subcutaneous lipid-rich cells. One aspect of certain embodiments is directed toward a rigid portion and a flexible portion. The rigid portion includes a thermal conductor that has an inside surface and an outside surface positioned opposite the inside surface. The flexible portion has an inner surface, an outer surface positioned opposite the inner surface, and a cutout extending between the inner and outer surfaces. The thermal conductor is positioned in the cutout and the flexible and rigid portions define a body. The body has an interior surface and an exterior surface. The interior surface includes the inside face of the rigid portion and the inner surface of the flexible portion, and the exterior surface includes the outside face of the rigid portion and the outer surface of the flexible portion.

Other aspects of the present invention are generally directed toward a system for treating subcutaneous lipid-rich cells in a target area. One aspect of certain embodiments is directed toward a treatment device and a token. The treatment device includes an applicator that is configured to operably engage the target area. The applicator includes a heat removal source that is configured to remove heat from the lipid-rich cells. The token interfaces with the treatment device to permit a treatment with the treatment device. The token includes a microelectronic device that is electrically coupled with the heat removal source while the token interfaces with the treatment device.

Other aspects of the present invention are generally directed toward a method for treating subcutaneous lipid-rich cells in a target area. One aspect of certain embodiments is directed toward configuring a treatment device for the target area, permitting use of the treatment device within a predetermined limit, verifying that continued use of the treatment device is within the predetermined limit and prohibiting use of the treatment device when the predetermined limit is exceeded. The treatment device includes a heat removal source configured to remove heat from the lipid rich cells.

Other aspects of the present invention are generally directed toward a vacuum applicator for treating subcutaneous lipid-rich cells with a cooling/heating unit. One aspect of certain embodiments is directed toward a rigid portion and a flexible portion. The rigid portion has an inside surface, an outside surface, and a rigid edge that extends between the inside and outside surfaces. The rigid portion includes a thermal conductor coupling the inside and outside surfaces. The flexible portion has an inner surface, an outer surface positioned opposite the inner surface, and a flexible edge that extends between the inner and outer surfaces. The flexible and rigid portions define a body that has an interior surface, an exterior surface, and an aperture. The interior surface includes the inside face of the rigid portion and the inner surface of the flexible portion. The exterior surface includes the outside face of the rigid portion and the outer surface of the flexible portion. The aperture includes the rigid edge of the rigid portion and the flexible edge of the flexible portion.

Other aspects of the present invention are generally directed toward a method for treating lipid-rich cells disposed under a cutaneous layer. One aspect of certain embodiments is directed toward coupling a heat removal source to an exterior surface of a thermally conductive plate of a vacuum applicator, coupling a suction source to an interior cavity of the vacuum applicator, placing the vacuum applicator on the cutaneous layer, activating the suction source to draw the cutaneous layer into the interior cavity of the vacuum applicator, and activating the heat removal source to remove heat from the lipid-rich cells.

Other aspects of the present invention are generally directed toward a device for treating lipid-rich cells disposed under a cutaneous layer. One aspect of certain embodiments is directed toward a base, a fitting, and a thermal conductor. The base includes a first attachment. The fitting includes a first portion of a contour that defines a mouth of a cavity. The fitting also includes a second attachment that is coupled to the first attachment in a first device arrangement and is decoupled from the first attachment in a second device arrangement. The thermal conductor is disposed about at least a portion of the cavity and is configured for heat transfer with respect to the lipid-rich cells when the contour engages the cutaneous layer in the first device arrangement.

Other aspects of the present invention are generally directed toward a device for treating lipid-rich cells disposed under a cutaneous layer. One aspect of certain embodiments is directed toward a vacuum cup that defines an interior cavity, a thermal conductor disposed about at least a portion of the cavity, and an adjustor. The vacuum cup includes a contour that defines a mouth of a cavity. The thermal conductor is configured for heat transfer with respect to the lipid-rich cells when the contour engages the cutaneous layer. The adjustor is configured to adjust at least one of (a) dimensions of the interior cavity, and (b) position of the thermal conductor with respect to the interior cavity.

Other aspects of the present invention are generally directed toward a system for treating subcutaneous lipid-rich cells in a target area. One aspect of certain embodiments is directed toward a base, a first fitting, a second fitting, and a thermal conductor. The base includes a first attachment. The first fitting includes a portion of a first contour that defines a first mouth of a first cavity. The fitting includes a second attachment that is coupled to the first attachment in a first device arrangement and is decoupled from the first attachment in a second device arrangement. The second fitting includes a portion of a second contour that defines a second mouth of a second cavity. The second fitting includes a third attachment that is coupled to the first attachment in a third device arrangement. The thermal conductor is disposed about at least a portion of the cavity. The thermal conductor is configured for heat transfer with respect to the lipid-rich cells when the first contour engages the cutaneous layer in the first arrangement and when the second contour engages the cutaneous layer in the third arrangement.

Other aspects of the present invention are generally directed toward a method. One aspect of certain embodiments is directed toward coupling a first fitting to a base of a vacuum applicator, placing the first fitting on a first cutaneous layer area, transferring heat between a thermal conductor and lipid-rich cells disposed under the first cutaneous layer area, displacing the first fitting from the first cutaneous layer area, decoupling the first fitting from the base, coupling a second fitting to the base, placing the second fitting on a second cutaneous layer area, and transferring heat between the thermal conductor and lipid-rich cells disposed under the second cutaneous layer area.

Suitable Treatment System

FIG. 1 and the following discussion provide a brief, general description of a suitable treatment system 10 in which aspects of the disclosure can be implemented. Those skilled in the relevant art will appreciate that the disclosure can be practiced with other treatment systems and treatment protocols, including invasive, minimally invasive, other non-invasive medical treatment systems, and/or combinations of one or more of the above for treating a subject 11. In general, the term "treatment system", as used generally herein, refers to any of the above system categories of medical treatment as well as any treatment regimes or medical device usage.

The treatment system 10 is suitable for treating a subject's subcutaneous adipose tissue, such as by cooling. "Subcutaneous tissue" can include tissue lying beneath the dermis and includes subcutaneous fat, or adipose tissue that may be composed primarily of lipid-rich cells, or adipocytes. When cooling subcutaneous tissues to a temperature lower than 37° C., subcutaneous lipid-rich cells can be affected selectively. In general, the epidermis and dermis of the subject 11 lack lipid-rich cells compared to the underlying lipid-rich cells forming the adipose tissue. Because non-lipid-rich cells usually can withstand colder temperatures better than lipid-rich cells, the subcutaneous lipid-rich cells can be affected selectively without affecting the non-lipid-rich cells in the dermis, epidermis and other surrounding tissue. In some embodiments, the treatment system 10 can apply cooling temperatures to the skin of the subject 11 in a range of from about −20° C. to about 20° C. In other embodiments, the cooling temperatures can be from about −20° C. to about 10° C., from about 0° C. to about 20° C., from about −15° C. to about 5° C., from about −5° C. to about 15° C., or from about −10° C. to about 0° C.

Without being bound by theory, the selective effect of cooling on lipid-rich cells is believed to result in, for example, membrane disruption, cell shrinkage, disabling, destroying, removing, killing or other method of lipid-rich cell alteration. Such alteration is believed to stem from one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissues. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce cellular apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by macrophages. As a result, phagocytes can engulf and remove the dying cells (e.g., the lipid-rich cells) without eliciting an immune response. Temperatures that elicit these apoptotic events in lipid-rich cells may contribute to long-lasting and/or permanent reduction and reshaping of subcutaneous adipose tissue.

One mechanism of apoptotic lipid-rich cell death by cooling is believed to involve localized crystallization of lipids within the adipocytes at temperatures that do not induce crystallization in non-lipid-rich cells. The crystallized lipids selectively may injure these cells, inducing apoptosis (and may also induce necrotic death if the crystallized lipids damage or rupture the bi-lipid membrane of the adipocyte). Another mechanism of injury involves the lipid phase transition of those lipids within the cell's bi-lipid membrane, which results in membrane disruption, thereby compromising the integrity and/or function of the cell membrane and inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews,* 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure also is believed to induce lipolysis (i.e., fat metabolism) of lipid-rich cells and has been shown to enhance existing lipolysis which serves to further increase the reduction in subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

In various embodiments, the treatment system 10 includes a controller, a computing device, a data acquisition device, a chiller, and one or more applicators. The treatment system 10 can employ these components in various embodiments to receive a selection of a treatment profile and apply the selected treatment to a subject 11.

FIG. 1 is a perspective view illustrating a treatment system 10 for non-invasively removing heat from subcutaneous lipid-rich target areas of a subject 11 such as an abdominal area 12 or another suitable area. The system 10 may include a treatment device 14 that engages the target area of the subject 11 for cooling or removing heat from the subcutaneous lipid-rich cells of the subject 11. It will be understood that treatment devices 14 can have various, configurations, shapes and sizes suitable for different body parts such that removing heat from any subcutaneous lipid-rich target area of the subject 11 can be achieved.

The treatment device 14 includes an applicator 15 that cools a target area of the subject 11, such as a human or animal (i.e., "subject 11"). Various types of applicators may be applied during treatment, such as a vacuum applicator (which may be used in combination with a massage or vibrating capability). Each applicator may be designed to treat target areas of the patient's body, such as chin, cheeks, arms, pectoral areas, thighs, calves, buttocks, back, abdomen, "love handles," and so forth. For example, a vacuum applicator may be applied at the back region with or without massage or vibration. Examples of applicators and their configurations usable with system 10 are described variously in, e.g., commonly assigned U.S. Patent Publication Nos. 2007/0198071, 2008/0077201, and 2008/0077211 and in U.S. patent application Ser. No. 11/750,953. In certain embodiments, the system 10 may also include a patient protective device, e.g., a sleeve or liner, for preventing direct contact between the applicator 15 and a patient's skin, and thereby reducing the likelihood of cross-contamination between patients, minimizing cleaning requirements for the applicator 15, etc. In certain other embodiments, the patient protection device may also include or incorporate various storage, computing, and communications devices, such as a radio frequency identification (RFID) component, allowing for example, use to be monitored and/or metered. Examples of liners or patient protection devices are described herein and in commonly assigned U.S. Patent Publication No. 2008/0077201.

The system 10 may further include a treatment unit 16 and supply and return fluid lines 18a and 18b between the treatment device 14 and the treatment unit 16. The treatment unit 16 can remove heat from a coolant to a heat sink and provide a chilled coolant to the treatment device 14 via the fluid lines 18a and 18b. Alternatively, the treatment unit 16 can circulate warm coolant to the treatment device 14 during periods of warming. Examples of the circulating coolant include water, glycol, synthetic heat transfer fluid, oil, a refrigerant, and/or any other suitable heat-conducting fluid. The fluid lines 18a and 18b may be hoses or other conduits constructed from polyethylene, polyvinyl chloride, polyurethane, and/or other materials that can accommodate the particular circulating coolant. The treatment unit 16 may be a refrigeration unit, a cooling tower, a thermoelectric chiller or cooler, or any other device capable of removing heat from a coolant. Alternatively, a municipal water supply (i.e., tap water) may be used in place of the treatment unit. Furthermore, one skilled in the art will recognize that there are a number of other cooling technologies that could be used such that the treatment unit or chiller need not be limited to those described herein.

In the embodiment illustrated in FIG. 1, the treatment device 14 may provide mechanical energy to create a vibratory, massage, and/or pulsatile effect, such as described in, e.g., U.S. Pat. No. 7,367,341 and commonly assigned U.S. Patent Publication No. 2008/0287839. The treatment device 14 may include one or more actuators, such as motors with eccentric weight, or other vibratory motors such as hydraulic motors, electric motors, pneumatic motors, solenoids, other mechanical motors, piezoelectric shakers, and so on, to provide vibratory energy to the treatment site. Further examples include a plurality of actuators for use in connection with a single treatment device 14 and/or applicator 15 in any desired combination. For example, an eccentric weight actuator (not shown) may be coupled to a housing 14a (FIG. 3D) of the treatment device 14 and a pneumatic motor (not shown) may also be coupled to the housing 14a such that different effects may be provided to different sections of the same treatment device 14. This, for example, would give the operator of treatment system 10 options for differential treatments of lipid rich cells within a single target area or among multiple target areas of subject 11. The use of one or more actuators and actuator types in various combinations and configurations with a treatment device 14 or applicator 15 may be possible.

The treatment device 14 may include one or more Peltier-type thermoelectric elements. For example, the treatment device 14 may have a plurality of individually controlled thermal segments to create a custom spatial cooling profile and/or a time-varying cooling profile. Each custom treatment profile can include one or more segments, and each segment can include a specified duration, a target temperature, and control parameters for features such as vibration, massage, vacuum, and other treatment modes. Cooling devices having multiple individually controlled heat exchanging units are described, e.g., in commonly assigned U.S. Patent Publication No. 2008/0077211.

The system 10 may further include a power supply 20 and a processing unit 24 operatively coupled to the treatment device 14 and the applicator 15. In one example, the power supply 20 provides a direct current voltage via a power line 22 to a thermoelectric element that is coupled to the applicator 15 to remove heat from the subject 11. The processing unit 24 may monitor process parameters via sensors (not shown) placed proximate to the treatment device 14 through a signal line 26 to, among other things, adjust the heat removal rate based on the process parameters. The processing unit 24 may further monitor process parameters to adjust the applicator 15 based on the process parameters.

The processing unit 24 may be in direct electrical communication with treatment device 14 through the signal line 26 as shown in FIG. 1; alternatively, processing unit 24 may be connected to treatment device via a wireless or an optical communication link. Processing unit 24 may be any processor, programmable logic controller, distributed control system, and so on. Note that power line 22 and the signal line 26 are shown in FIG. 1 without any support structure. Alternatively, power line 22 and the signal line 26 (and other lines including, but not limited to fluid lines 18a and 18b) may be bundled into or otherwise accompanied by a conduit or the like to protect such lines, enhance user safety and ergonomic comfort, ensure unwanted motion (and thus potential inefficient removal or extraction of heat from subject 11) is minimized, provide electrical and thermal insulation and to provide an aesthetic appearance to system 10. Examples of such a conduit include a flexible polymeric, fabric, or composite sheath, an adjustable arm, etc. Such a conduit (not shown) may be designed (via adjustable joints, etc.) to "set" the conduit in place for the treatment of subject 11.

Figure 3A:
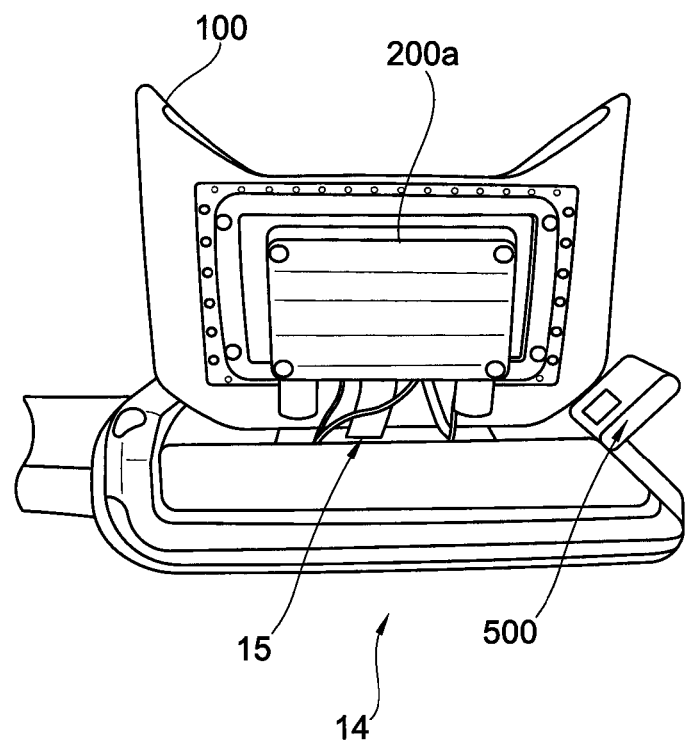
FIG. 3A is a side view showing an embodiment of a device for a treatment to removing or extracting heat from subcutaneous lipid-rich cells.
Figure 3C:
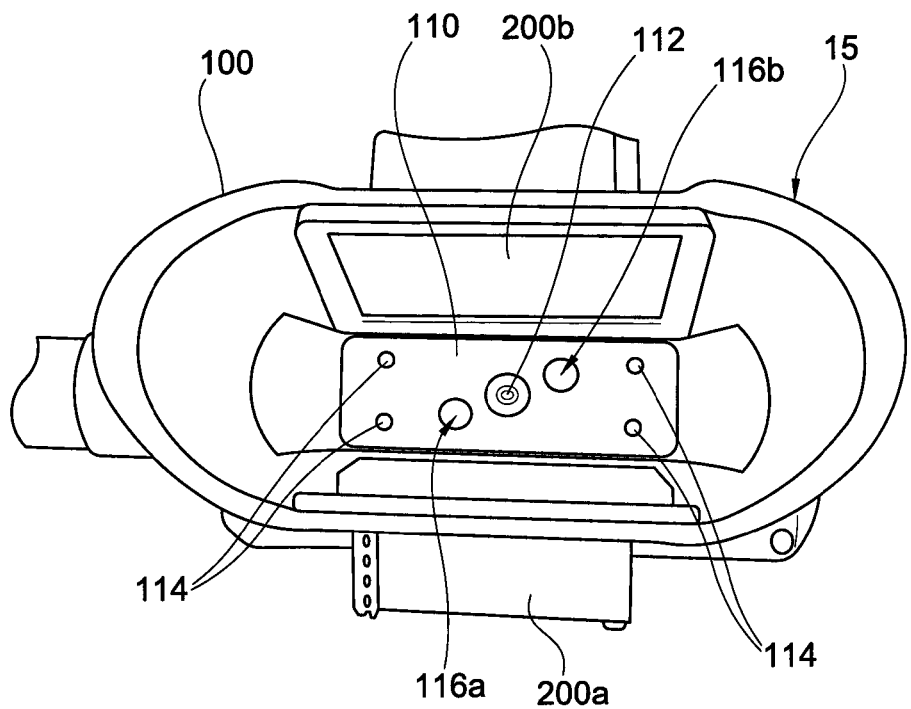
FIG. 3C is a bottom view showing the treatment device shown in FIG. 3A.
Figure 3B:
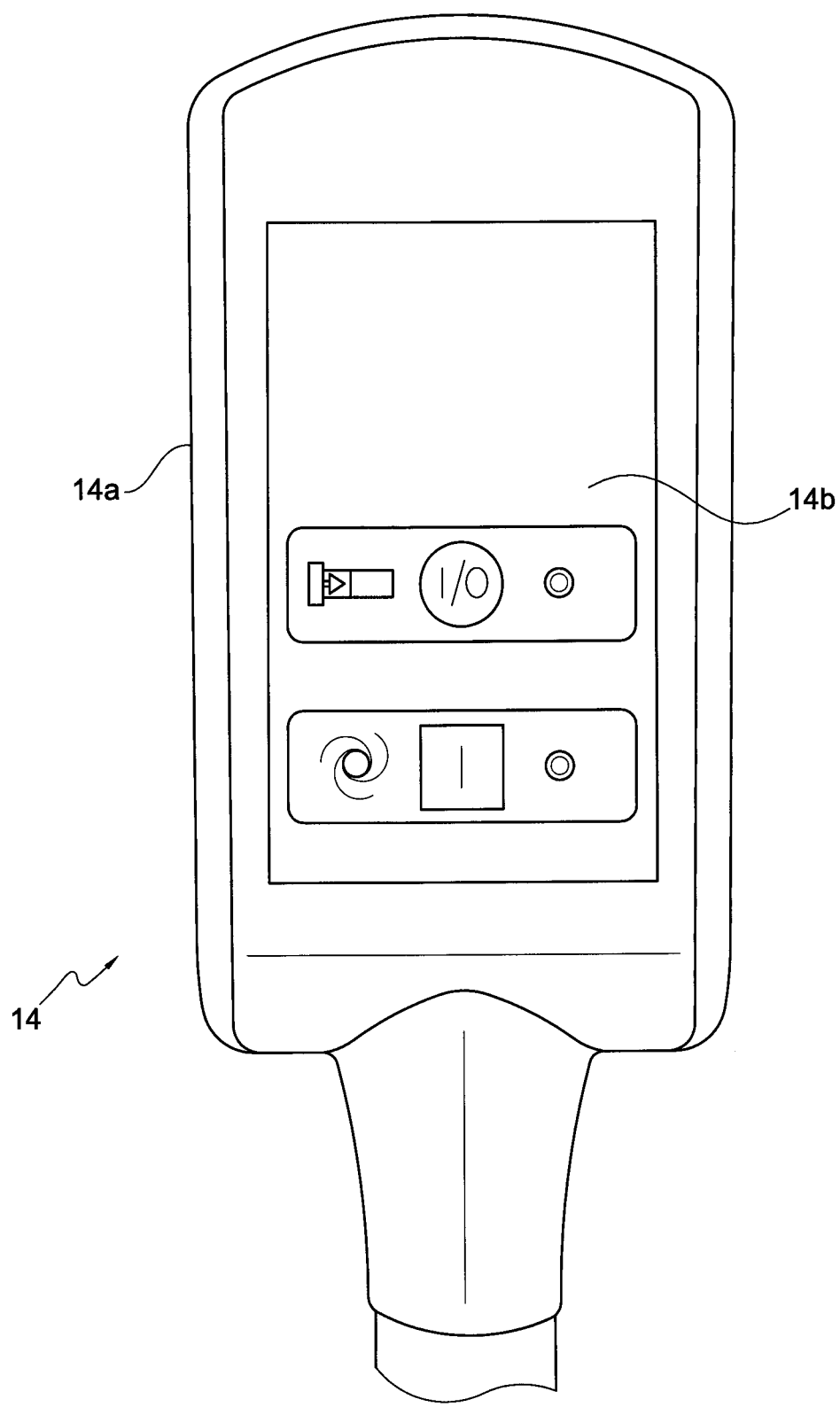
FIG. 3B is a top view showing a control panel of the treatment device shown in FIG. 3A.

In another aspect, the processing unit 24 may be in electrical or other communication with an input device 28, an output device 30, and/or a control panel 14b on the housing 14a of the treatment device 14 (shown in FIG. 3B). The input device 28 may be a keyboard, a mouse, a touch screen, a push button, a switch, a potentiometer, any combination thereof, and any other device or devices suitable for accepting user input. The output device 30 may include a display or touch screen, a printer, a medium reader, an audio device, a visual device, any combination thereof, and any other device or devices suitable for providing user feedback. In the embodiment of FIG. 1, the input device 28 and the output device 30 may be combined in a single unit such as a touch screen. The control panel 14b may include visual indicator devices or controls (lights, numerical displays, etc.) and/or audio indicator devices or controls. The control panel 14b may be a component separate from the input device and/or output device as shown in FIG. 3B, may be integrated with one or more of the input and output devices 28 and 30, may be partially integrated with one or more of the input and output devices 28 and 30, may be in another location, and so on. In this example, processing unit 24, power supply 20, control panel, treatment unit 16, input device 28, and output device 30 are carried by a rack or cart 34 with wheels 36 for portability. In alternative examples, the processing unit 24 may be contained in, attached to, or integrated with the treatment device 14 and/or the applicator 15 and/or the subject 11 protection device described above. In yet another example, the various components may be fixedly installed or integrated with patient supports (e.g., chair, gurney, etc.) or other appliances in a treatment suite. Further details with respect to components and/or operation of treatment device 14, applicator 15, and other components may be found in commonly-assigned U.S. Patent Publication No. 2008/0287839.

Without being bound by theory, it is believed that in operation effective cooling from the applicator 15, which cools through conduction, depends on a number of factors. Examples of factors that impact heat removal or extraction from the skin area and related tissue include, for example, the surface area of the treatment unit, the temperature of the interface member, and the mechanical energy delivered to the tissue. More specifically, in operation, and upon receiving input to start a treatment protocol, the processing unit 24 can cause the treatment device 14 to cycle through each segment of a prescribed treatment plan. In so doing, the treatment device 14 applies power to one or more cooling segments, such as thermoelectric coolers (e.g., TEC "zones"), to begin a cooling cycle and, for example, activate features or modes such as vibration, massage, vacuum, etc. Using temperature or heat flux sensors (not shown in FIG. 1) proximate to the one or more treatment devices 14, the applicator 15, a subject 11 liner or device, the patient's skin, or other locations or combinations thereof, the processing unit 24 determines whether a temperature or heat flux that is sufficiently close to the target temperature or heat flux has been reached. It will be appreciated that while a region of the body (e.g., adipose tissue) has been cooled or heated to the target temperature or by a target heat flux, in actuality that region of the body may be close but not equal to the target temperature, e.g., because of the body's natural heating and cooling variations. Thus, although the system may attempt to heat or cool to the target temperature or by a target heat flux, a sensor may measure a sufficiently close temperature. If the target temperature has not been reached, power can be increased or decreased to change heat flux, as needed, to maintain the target temperature or "setpoint." When the prescribed segment duration expires, the processing unit 24 may apply the temperature and duration indicated in the next treatment profile segment. In some embodiments, temperature can be controlled using a variable other than, or in addition to, power.

According to examples of the system, the treatment device 14 and the applicator 15 enhance disruption of cooled adipose tissue. Further, the examples may provide reduced treatment time, reduced discomfort to the subject 11 and increased efficacy of treatment.

Examples of the system may provide the treatment device 14 and the applicator 15 which damage, injure, disrupt or otherwise reduce subcutaneous lipid-rich cells generally without collateral damage to non-lipid-rich cells in the treatment target area. In general, it is believed that lipid-rich cells can be affected selectively (e.g., damaged, injured, or disrupted) by exposing such cells to low temperatures that do not so affect non-lipid-rich cells to the same extent or in the same manner. As a result, lipid-rich cells, such as subcutaneous adipose tissue, can be damaged while other cells in the same region are generally not damaged even though the non-lipid-rich cells at the surface are subject to even lower temperatures. The mechanical energy provided by the applicator may further enhance the effect on lipid-rich cells by mechanically disrupting the affected lipid-rich cells.

In some examples of the system, the treatment device may be used with a substance that may (a) provide a thermal coupling between the subject's skin and the cooling unit(s) 50 to improve heat transfer therebetween; and/or (b) protect biological tissues of a subject from freezing damage (e.g., damage due to ice formation). The substance may be a fluid, e.g., a liquid, a gel, or a paste, which may be hygroscopic, thermally conductive, and biocompatible. Some embodiments according to the present disclosure may use a cryoprotectant including a temperature depressant that can assist in preventing freezing of non lipid-rich tissue (e.g., dermal tissue) during treatment. Suitable cryoprotectants and processes for implementing cryoprotectants are described in commonly-assigned U.S. Patent Publication No. 2007/0255362. The temperature depressant can be part of a cryoprotectant that may additionally include a thickening agent, a pH buffer, a humectant, a surfactant, and/or other additives. The temperature depressant may include, for example, polypropylene glycol (PPG), polyethylene glycol (PEG), dimethyl sulfoxide (DMSO), or other suitable alcohol compounds. In a particular embodiment, a cryoprotectant may include about 30% polypropylene glycol, about 30% glycerin (a humectant), and about 40% ethanol. In another embodiment, a cryoprotectant may include about 40% propylene glycol, about 0.8% hydroxyethylcellulose (a thickening agent), and about 59.2% water. In a further embodiment, a cryoprotectant may include about 50% polypropylene glycol, about 40% glycerin, and about 10% ethanol.

In one mode of operation, the applicator 15 is coupled to a treatment device 14. As described below, applying the treatment device 14 with a vacuum type force to the skin of the subject 11 may be advantageous to achieve efficient treatment. In general, the subject 11 has a body temperature of about 37° C., and the blood circulation is one mechanism for maintaining a constant body temperature. As a result, blood flow through the skin and subcutaneous layer of the region to be treated may be viewed as a heat source that counteracts the cooling of the subdermal fat. Cooling the tissue of interest accordingly requires not only removing the heat from such tissue but also that of the blood circulating through this tissue. Thus, temporarily reducing or eliminating blood flow through the treatment region, by means such as, e.g., applying a vacuum can improve the efficiency of tissue cooling. Additionally, a vacuum may pull skin and underlying adipose tissue away from the body which can assist in cooling underlying tissue by, e.g., lengthening the distance between the subcutaneous fat and the relatively well-perfused muscle tissue and by allowing the underlying adipose tissue simultaneously to be cooled from two sides. Embodiments according to the present disclosure may include an interior cavity into which the tissue is pulled. The interior cavity may be provided with a single cooling surface or a plurality of cooling surfaces disposed at discrete locations anywhere around the interior cavity, or the interior cavity may be partially or entirely provided with cooling surface(s).

By cooling the subcutaneous tissue to a temperature lower than 37° C., subcutaneous lipid-rich cells may be damaged selectively. In general, the epidermis and dermis of the subject 11 have lower amounts of fatty acids compared to the underlying lipid-rich cells forming the subcutaneous tissues. Because non-lipid-rich cells usually can withstand colder temperatures better than lipid-rich cells, the subcutaneous lipid-rich cells can be injured selectively while maintaining the non-lipid-rich cells in the dermis and epidermis. For example, the temperature range may be from about −20° C. to about 10° C., from about 0° C. to about 20° C., from about −15° C. to about 5° C., from about −5° C. to about 15° C., or from about −10° C. to about 0° C.

Figure 2:
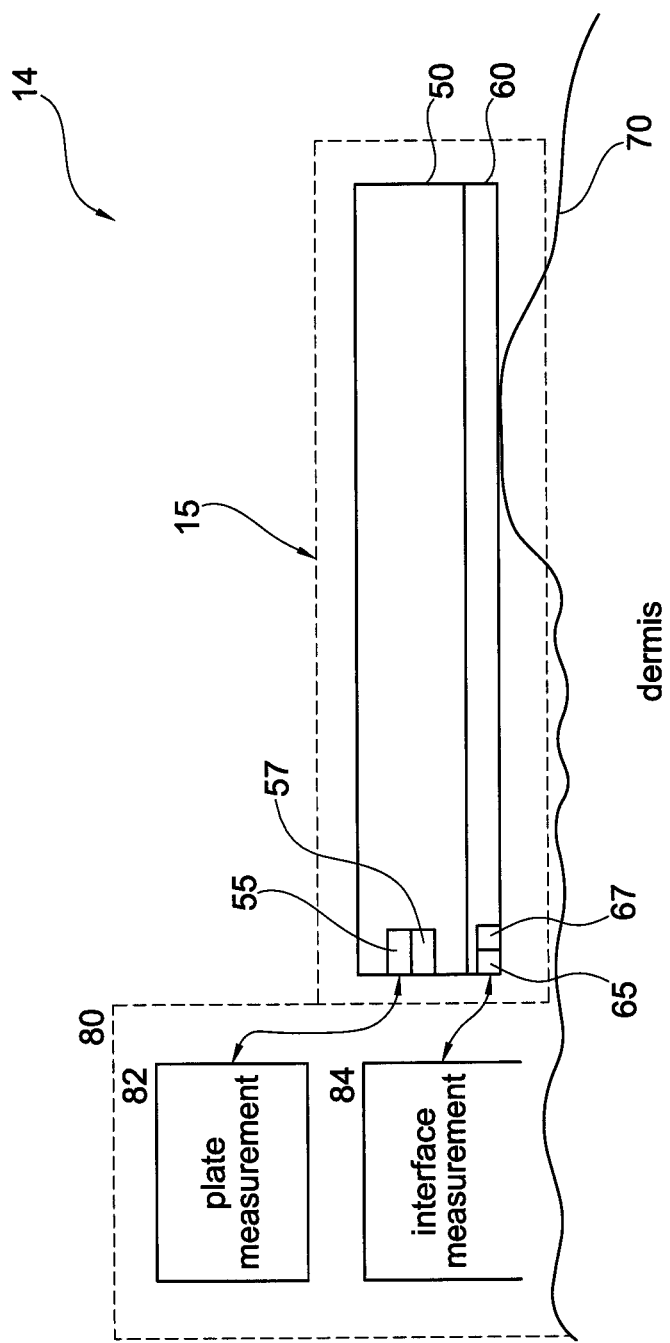
FIG. 2 is a schematic illustrating a treatment device for treating subcutaneous lipid-rich areas of a subject 11 in accordance with an embodiment of the disclosure.

FIG. 2 is a schematic illustrating a treatment device 14 for removing heat from subcutaneous lipid-rich cells. Treatment device 14 may include an applicator 15 with a cooling unit 50 and an interface layer 60. Interface layer 60 may be a plate, a film, a covering, or other suitable materials described herein and may serve as a subject 11 protection device described herein. The interface layer 60 is located between the cooling unit 50 and the skin 70 of a subject 11 receiving treatment via the treatment device 14. The cooling unit 50 may contain a communication component 55 that communicates with a controlling device 80 as described herein, and a measurement component 57 that measures one or more process parameters such as heat flux or the temperature of the cooling plate 50. The interface layer 60 may also contain a similar communication component 65 and a measurement component 67 that measures one or more process parameters such as heat flux or the temperature of the interface layer 60. For example, communication components 55, 65, and/or both may receive and transmit information from controlling device 80, such as temperature information determined by measurement units 57, 67, and/or both. The device 14 may also contain power components and other components described with respect to FIG. 1 and related applications.

In some cases, the patient protection device may include a sleeve and/or interface layer that is used to contact the patient's skin. One example of such a sleeve has a first sleeve portion and a second sleeve portion. The first sleeve portion may contact and/or facilitate the contact of the treatment device with the patient's skin. The second sleeve portion may be an isolation layer extending from the first sleeve portion. For example, the second sleeve portion may be constructed from latex, rubber, nylon, Kevlar®, or other substantially impermeable or semi-permeable material. The second sleeve portion may prevent contact between the patient's skin and the cooling plates, among other things. Further details regarding a patient protection device may be found in U.S. Patent Publication No. 2008/0077201.

The treatment device of the present disclosure may use vacuum to assist in forming a contact between the treatment device and the patient's skin. The vacuum may also be used to impart mechanical energy during treatment. Imparting mechanical vibratory energy to a target area by, e.g., repeatedly applying and releasing a vacuum to the subject's tissue, or for instance, modulating a vacuum level applied to the subject's tissue, creates a massage action during treatment.

Figure 3D:
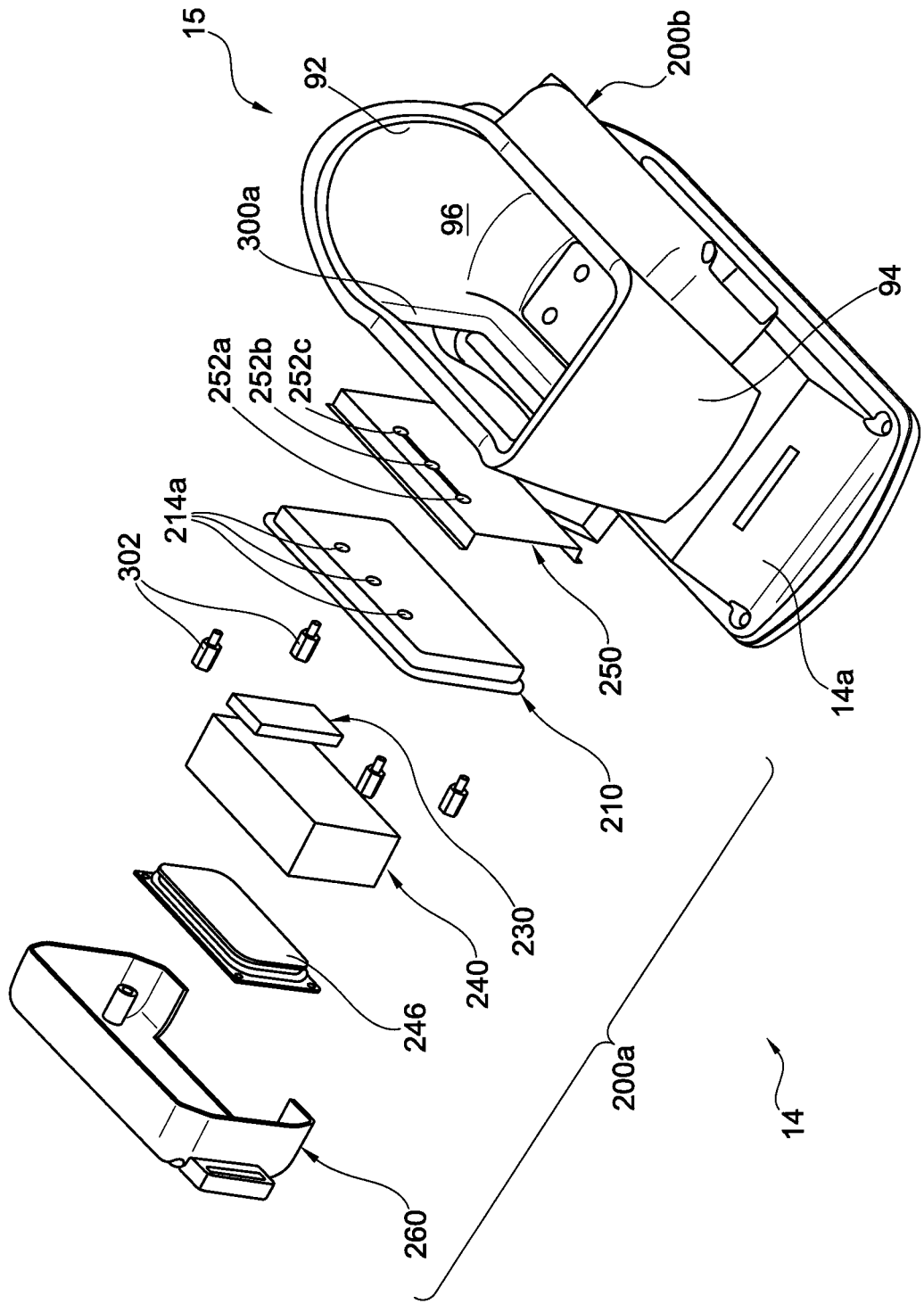
FIG. 3D is a partially exploded perspective view of the treatment device shown in FIG. 3A.
Figure 3E:
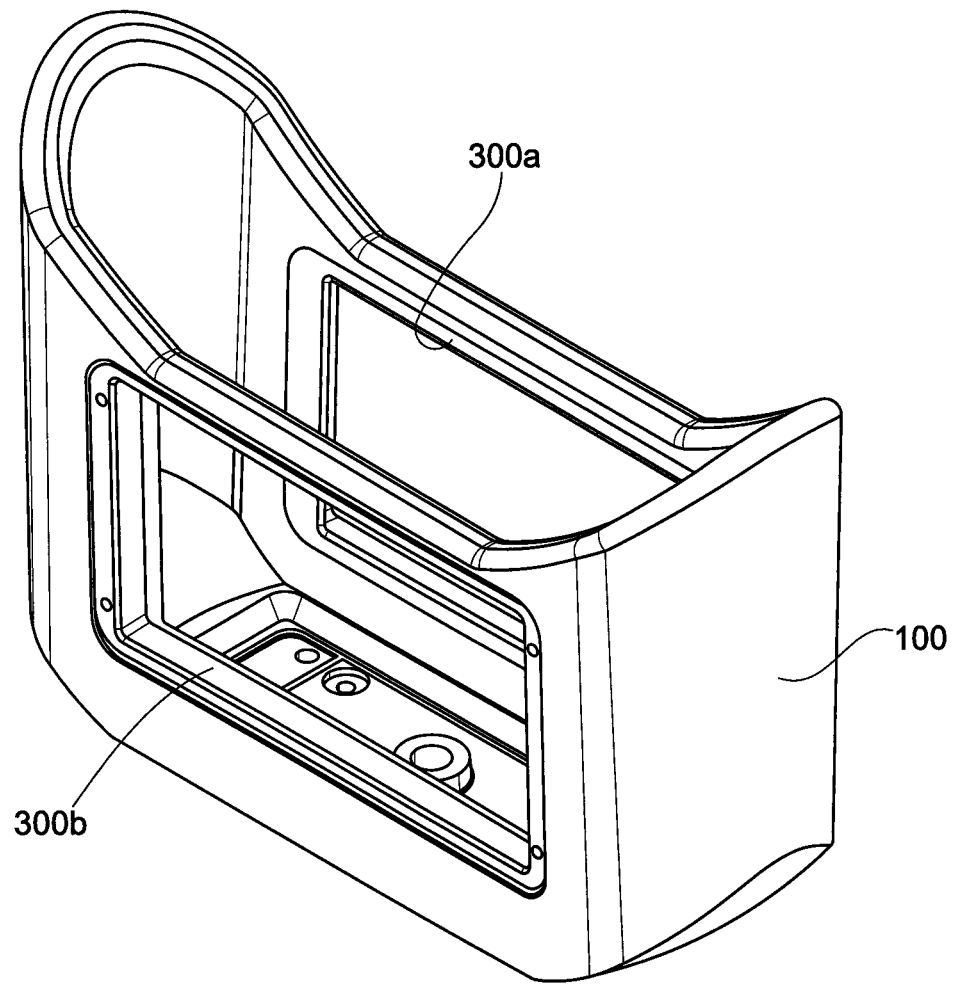
FIG. 3E is a detail view of a component of the treatment device shown in FIG. 3A.

FIG. 3A is a side view showing a portion of a treatment device 14 for removing heat from subcutaneous lipid-rich cells according to one embodiment of the present technology. FIG. 3B is a top view of the treatment device 14 showing the housing 14a and the control panel 14b, and FIG. 3C is a bottom view showing the applicator 15 coupled to the treatment device 14. FIG. 3D is a partially exploded perspective view of the treatment device 14 illustrating certain features of the applicator 15. FIG. 3E is a detail view of a component of the applicator 15. The applicator 15 may include a flexible portion 100, at least one generally rigid portion, for example, panels 200a and 200b, and at least one frame 300 (shown individually as frames 300a and 300b in FIG. 3E) between the panels 200a and 200b and the flexible portion 100. In the illustrated embodiment, the applicator 15 has an interior surface 92 and an exterior surface 94. The interior surface 92 defines an interior cavity 96 in which a vacuum may be drawn.

Referring to FIG. 3B, the control panel 14b may be located on the treatment device 14 so as to be readily accessible to the operator of treatment system 10. The control panel 14b may provide the operator with the ability to control and/or monitor the treatment at the treatment device 14. For example, a first ON/OFF button may toggle the initiation or termination of a treatment and a second ON/OFF button may actuate a pump (not shown) for drawing a vacuum in the interior cavity 96. Indicator lights may provide a visual indication of, for example, whether a treatment is proceeding and/or whether the vacuum pump is activated.

Referring to FIG. 3C, the applicator 15 may be coupled to the treatment device 14 by a mounting plate 110 that clamps the flexible portion 100 into fluid-tight engagement with the housing 14a. The mounting plate 110 may be integrally formed with the flexible portion 100 or separately coupled to the flexible portion 110. An aperture 112 in the mounting plate 110 provides a passage for drawing a vacuum in the interior cavity 96. At least one fastener 114, e.g., four screws are shown in FIG. 3C, may releasably secure the mounting plate 110 to the housing 14a. Accordingly, removing the fasteners 114 allows the applicator 15 to be replaced with respect to the treatment device 14. In other embodiments, adhesive or another type of fastener may be used to couple the applicator 15 to the treatment device 14 either with or without using the mounting plate 110. The mounting plate 110 may also include one or more magnets 116 (two magnets 116a and 116b are shown in FIG. 3C) for releasably retaining the interface layer 60 (FIG. 2). Additionally, a sensor such as an electrical conductivity circuit detector (not shown) may be coupled through the at least two magnets 116 for sensing whether a liner 400 (FIGS. 6A-6C) is disposed in the interior cavity 96 of the applicator 15.

Referring to FIG. 3D, each rigid portion 200 may include a cold plate 210, at least one thermoelectric cooler (TEC) 230, a heat exchanger 240, a flexible printed circuit 250, and a protective housing 260 that covers the rigid portion 200. Individual rigid portions 200 are relatively stiff as compared to the flexible portion 100. Accordingly, the rigid portions 200 may resist bowing or other deformation as a vacuum is drawn in the interior cavity 96. Such deformation could reduce the ability of the TEC 230 to draw heat through the cold plate 210 from the subcutaneous lipid-rich cells.

Figure 4A:
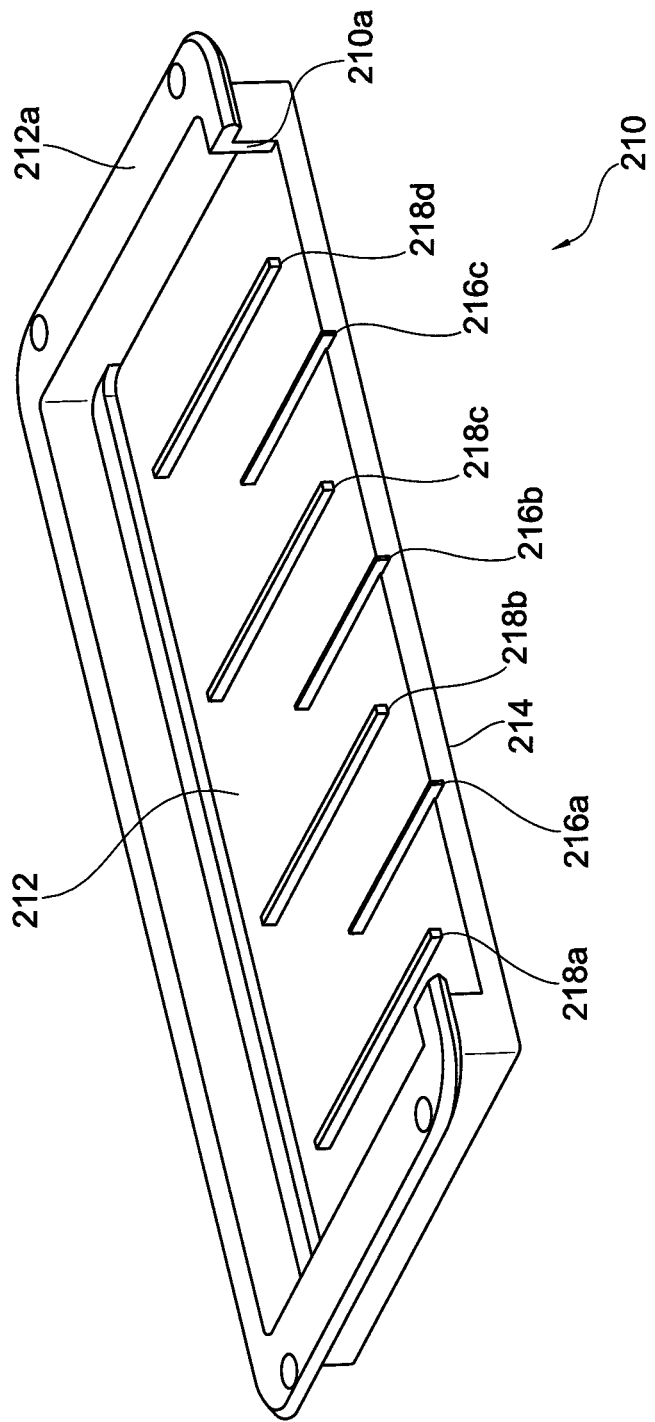
FIGS. 4A-4D show different stages of assembling an embodiment of a rigid portion of the treatment device shown in FIG. 3A.
Figure 4B:
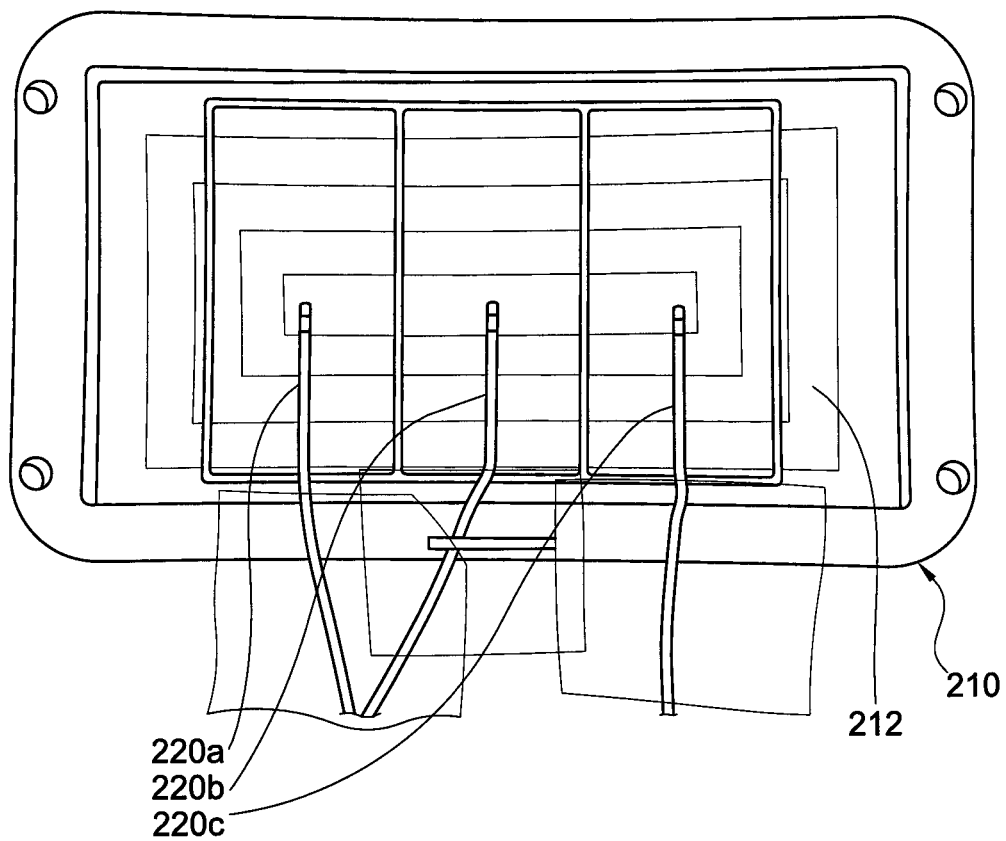
Figure 4C:
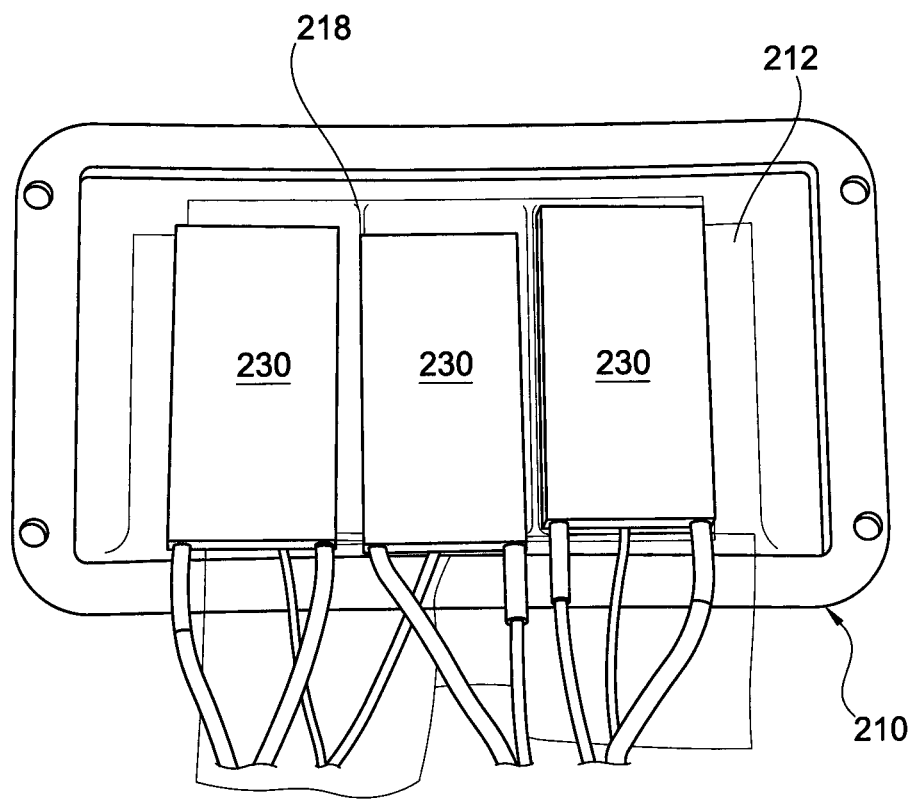
Figure 4D:
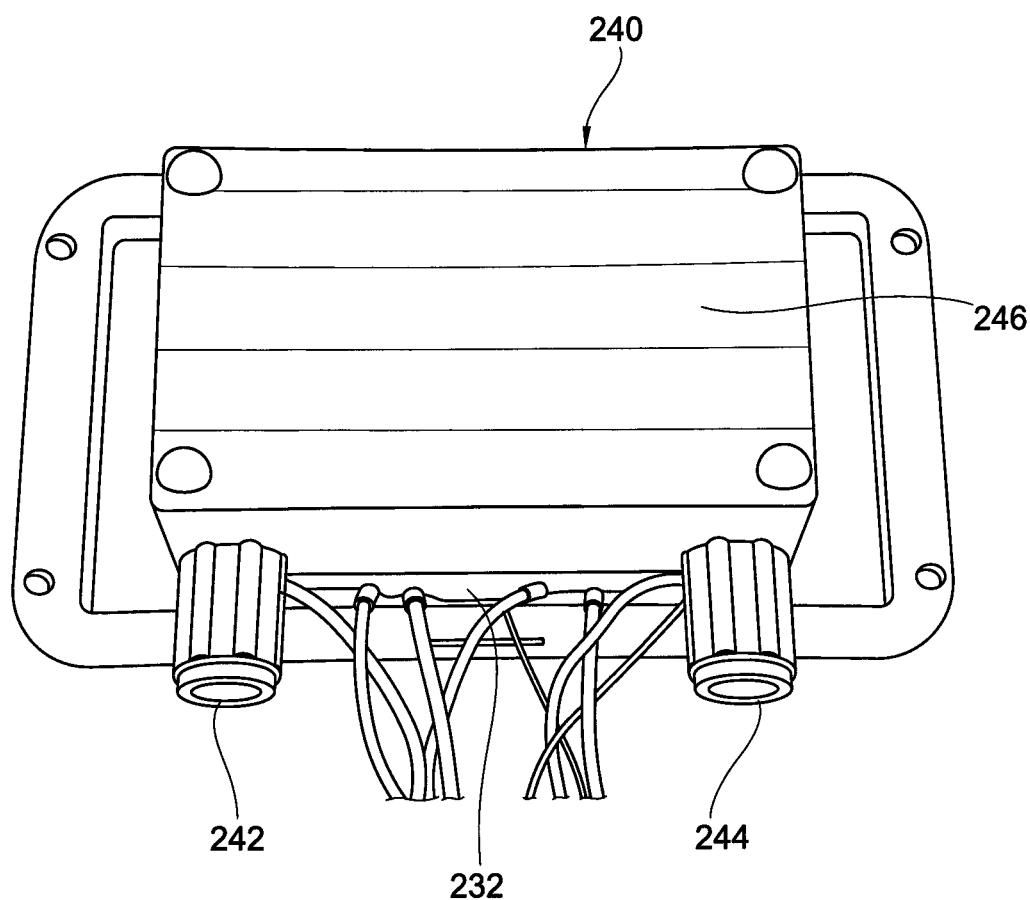

FIGS. 4A-4D show different stages of assembling an individual rigid portion 200. In particular, FIG. 4A shows an embodiment of the cold plate 210, FIG. 4B shows an example of three measurement components 57 (FIG. 2) positioned on the cold plate 210, FIG. 4C shows three TECs 230 (shown individually as TECs 230a-230c) positioned over the measurement components 57, and FIG. 4D shows the heat exchanger 240 covering the TECs 230.

Referring to FIG. 4A, the cold plate 210 may be an aluminum or copper panel having a first surface 212 and a second surface 214. In other embodiments, the cold plate 210 may include other materials that are suitably rigid and thermally conductive. The cold plates 210 resist deformation, such as bowing while a vacuum is drawn in the interior cavity 96 (FIG. 3D), and maintain a thermal path between the TECs 230 (FIG. 3D) and the subject 11. The first surface 212, which may have a concave profile as shown in FIG. 4A, may include one or more recesses 216 (three recesses 216a-216c are shown in FIG. 4A) to receive the measurement components 57 (FIG. 2) and may include one or more shoulders 218 (four shoulders 218a-218d are shown in FIG. 4A) to position the TECs 230. The periphery of the first surface 212 may include a mounting flange 212a having one or more features (e.g., four apertures are shown) for coupling the rigid portion 200 to a frame 300 (FIGS. 3D and 3E). The cold plate 210 may also include a cutout 210a through which wires for the measurement components 57 and/or the TECs 230 may pass.

Referring to FIG. 4B, the measurement components 57 (FIG. 2) may include, for example, at least one temperature sensor 220 (three temperature sensors 220a-220c are shown in FIG. 4B) that are positioned on the first surface 212 to detect the temperature of the cold plate 210. According to certain embodiments, the temperature sensors 220 may include thermisters (e.g., BetaTherm model 10K3MBD12 thermisters) or other types of sensors suitable for detecting the temperature at one or more locations on the cold plate 210. Electrical wires from the temperature sensors 220 may be temporarily held in place by an adhesive coated polyimide film, such as Kapton®, or another suitable tape. Alternatively, the temperature sensors 220 may be inserted in the recesses 216a-216c (FIG. 4A) with their wires passing through the cutout 210a (FIG. 4A). Some embodiments according to the present disclosure may include measurement components 57 and 67 that measure parameters other than temperature, e.g., heat flux. Further, the measurement components 57 and 67 may use differential signals to reduce the coupling or influence of ambient noise into the measurement component signal(s).

Referring to FIG. 4C, the shoulders 218 may be used to position the TECs 230 over the temperature sensors 220 on the first surface 212. The TECs 230 may be coupled with respect to the first surface 212 by a thermal interface pad (not shown), e.g., Loctite® Powerstrate® Xtreme™, or any suitable adhesive that does not provide appreciable thermal insulation between the TECs 230 and the cold plate 210. The TECs 230 may include a Peltier device or another solid-state active heat pump that uses electricity to transfer heat from one side to the other side of the TECs 230. In operation, the TECs 230 transfer heat from a "cold" side that is thermally coupled to the cold plate 210 to a "hot" side that is thermally coupled to the heat exchanger 240 (FIG. 3D). A sealant 232 (FIG. 4D), which may be a thermally conductive adhesive, bonds and provides a seal between the TECs and the cold plate 210, bonds and provides a seal between the cold plate 210 and the heat exchanger 240, and provides a seal around the wires leading from the temperature sensors 220 (FIG. 4B). Sealant 232 also serves to minimize the thermal resistance between the components with which it comes into contact. An example of a suitable sealant material is a thermally conductive elastomer available from the Dow Corning Corporation, Catalog No. 3-6651.

Referring to FIG. 4D, the heat exchanger 240 is positioned over the TECs 230 (FIG. 4C) and sealed relative to the cold plate 210 with the sealant 232. The heat exchanger 240 includes a fluid inlet 242 and a fluid outlet 244 that cooperatively engage corresponding tubing (not shown) from the housing 14a of the applicator 14. The heat exchanger 240 may also include a cover 246 (also FIG. 3D) that provides access to the interior of the heat exchanger 240. In operation, coolant may flow from the treatment unit 16 (FIG. 2), through the fluid supply line 18a (FIG. 2), through the housing 14a, through the fluid inlet 242, to the heat exchanger 240. The fluid absorbs heat from the "hot" side of the TECs 230 in the heat exchanger 240 and then flows through the fluid outlet 244, through the housing 14a, through the fluid return line 18b (FIG. 2), to the treatment unit 16. Accordingly, the treatment unit 16 can provide a heat sink for removing heat transferred by the TECs 230, via the cold plate 210, from the subcutaneous lipid-rich cells.

The flexible printed circuit 250 (FIG. 3D) may be coupled, e.g., adhered, to the second surface 214 of the cold plate 210 and may include one or more heat flux or temperature sensors 252 (three temperature sensors 252a-252c are shown in FIG. 3D) to detect the temperature of the patient's skin. According to certain embodiments, the temperature sensors 252 may include thermistors, thermocouples, thermopiles, or other types of sensors suitable for detecting the temperature and/or heat flux at one or more locations on the patient's skin. In order to provide a flat surface confronting the patient's skin, the temperature sensors 252 can be mounted on the surface of the flexible printed circuit 250 that faces the cold plate 210. The physical volume that each temperature sensor 252 occupies can be accommodated in corresponding recesses 214a (FIG. 3D) that are formed in the second surface 214. Any unoccupied volume in the recesses 214a may be filled with foam, a room temperature vulcanizing material, or another backing material so that the flexible printed circuit 250 cannot deflect into the recesses 214a. Kapton®, another polyimide film, or another suitable material may be included as a substrate for the flexible printed circuit 250.

The signals output from the temperature sensors 252 can be electrically coupled via conductive traces (not shown) that may extend into the housing 14a and electrically couple the temperature sensors 252 to electric circuitry (not shown) in the housing 14a of the applicator 14 and/or to the electrical line 22 (FIG. 1). According to other embodiments, the signals output from the temperature sensors 252 can be transmitted wirelessly rather than via the conductive traces. In operation, the temperature sensors 252 can detect a temperature that can be correlated to the patient's skin temperature, e.g., compensating for the presence of the interface layer 60 (FIG. 2), a thermal coupling fluid, and/or other factors that may cause the temperature measured by the temperature sensors 252 to deviate from the actual temperature of the patient's skin or subcutaneous adipose tissue at a pre-defined depth.

The printed circuit 250 may also include a microelectronic device (not shown) that may include a microprocessor, memory, an input/output device, or combinations thereof. The microelectronic device may be electrically coupled to the signals output from the temperature sensors 252 and provide, for example, storage, computing, and/or communications for the output signals.

Figure 5A:
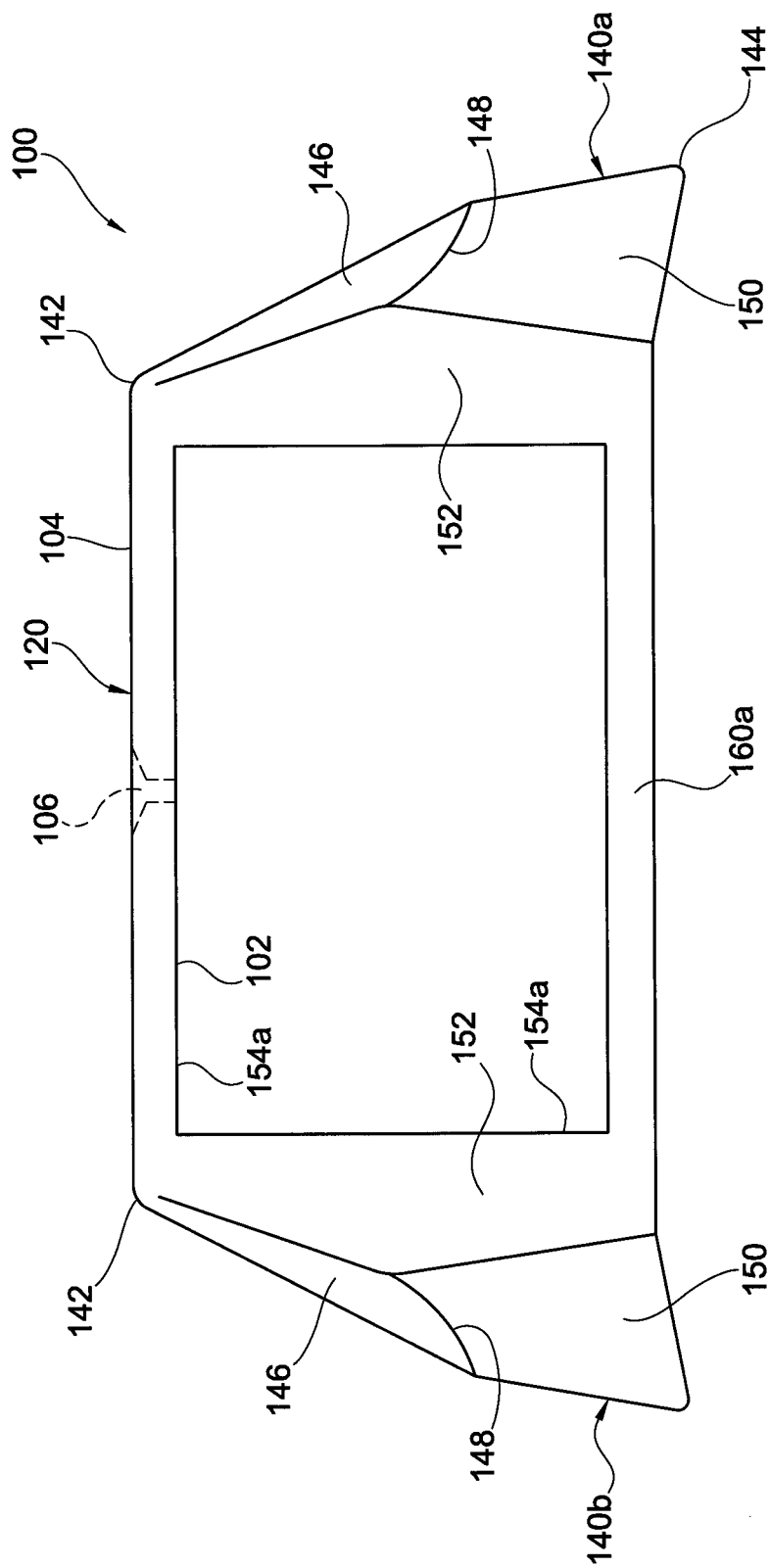
FIG. 5A shows a front view of an embodiment of a flexible portion of the treatment device shown in FIG. 3A.
Figure 5B:
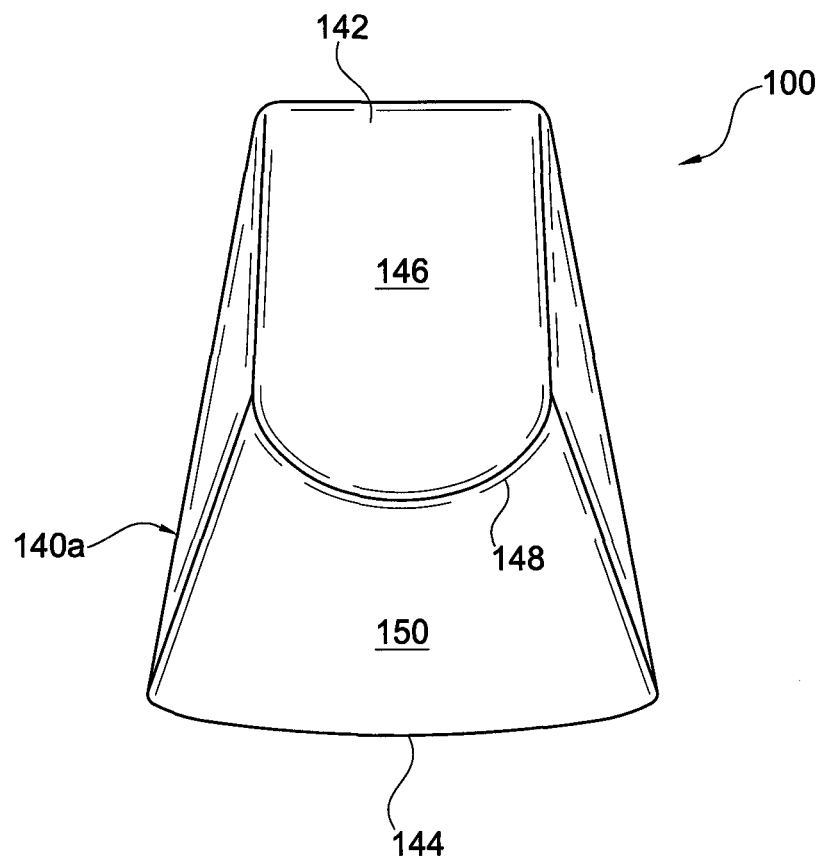
FIG. 5B is an end view of the flexible portion shown in FIG. 5A.
Figure 5C:
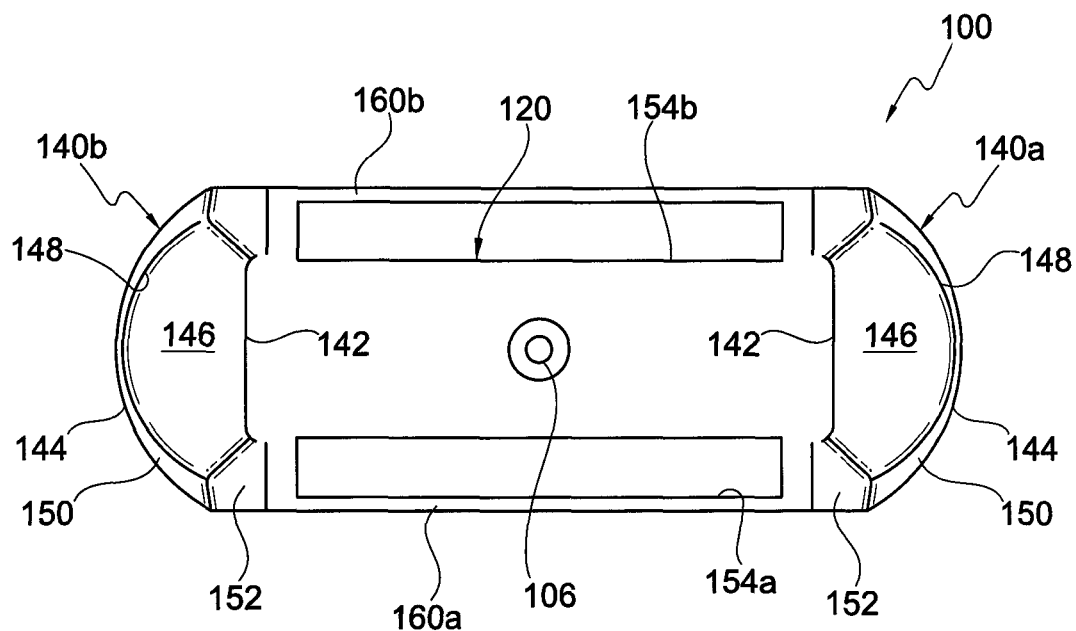
FIG. 5C is a top view of the flexible portion shown in FIG. 5A.
Figure 5D:
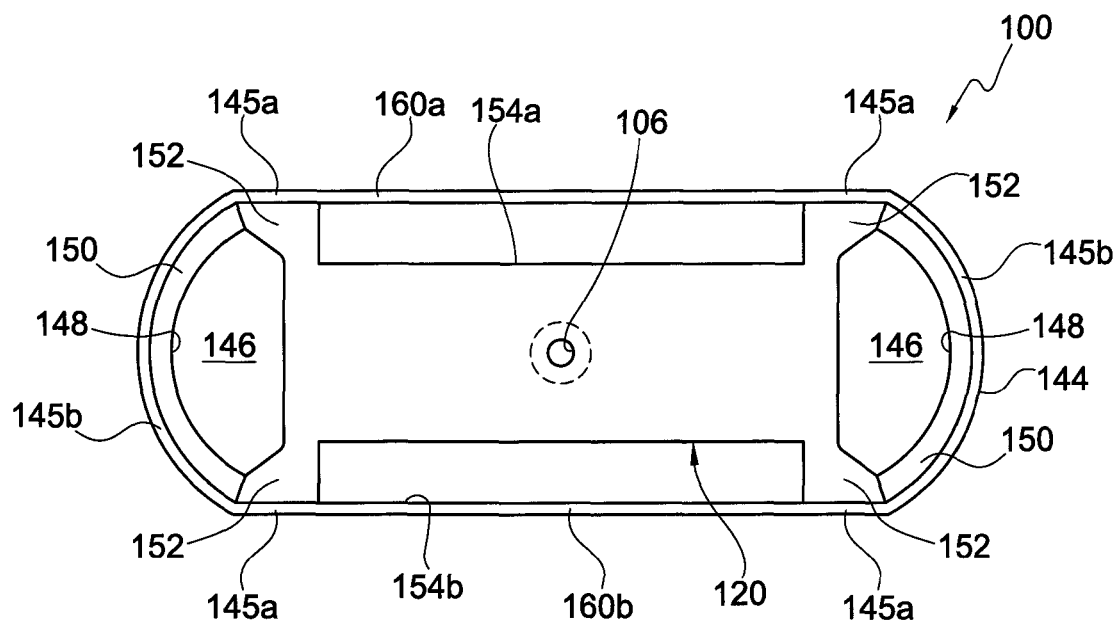
FIG. 5D is a bottom view of the flexible portion shown in FIG. 5A.

FIG. 5A shows a front view of an embodiment of the flexible portion 100 of the applicator 15. FIG. 5B is an end view, FIG. 5C is a top view, and FIG. 5D is a bottom view of the flexible portion 100 shown in FIG. 5A. The flexible portion 100 can be molded from an elastically deformable plastic, e.g., silicone, elastomer, or another material that is suitably flexible. The flexible portion 100 may be transparent to facilitate viewing the skin through the flexible portion 100. In other embodiments, the flexible portion 100 can be translucent or opaque. The flexible portion 100 may include a generally rectangular top surface coupled to the housing 14a and a bottom surface including parallel or nearly parallel sides and elliptical ends.

Referring to FIG. 5A, the flexible portion 100 includes a central portion 120, ends 140 (shown individually as ends 140a and 140b), and connectors 160 (shown individually as connectors 160a and 160b) that extend between and couple the bottoms of the ends 140, i.e., opposite from the central portion 120. In the embodiment shown in FIGS. 5A-5D, a "contour" or the shape of the applicator 15 that is fitted to the subject 11 includes a combination of the lips 144 and the connectors 160. The flexible portion 100 also includes an interior surface 102, an exterior surface 104, and a port 106 that extends between the interior and exterior surfaces 102 and 104 and through which a vacuum is drawn in the interior cavity 96 (FIG. 3D). The port 106 and the aperture 112 (FIG. 3C) are approximately aligned when the mounting plate 110 (FIG. 3C) is used to couple the flexible portion 100 to the housing 14a.

Referring to FIG. 5B, each end 140 has a top portion 142 extending from the central portion 120. The ends 140 and central portion 120 can be integrally molded or formed as separate components that are coupled together. As best shown in FIGS. 5B-5D, each end 140 has a lip 144 at the bottom, i.e., opposite from the top portion 142. The lip 144 may have a three dimensional geometry to facilitate conforming to a contour of a patient's skin. For example, with particular reference to FIG. 5D, a nominal configuration of the lip 144 may include straight segments 145a, arcuate segments 145b, or a combination of both when viewed from above or below. Concurrently, with particular reference to FIG. 5B, the nominal configuration of the lip 144 may include an arcuate profile view, and with particular reference to FIG. 5A, the frontal view of the nominal configuration of the lip 144 may include a downward slant with respect to the central portion 120. According to other embodiments, lip 144 may have different geometries suitable for conforming to the contours of given target areas of the applicator 15.

The individual ends 140 may have overall geometries between the top portion 142 and the lip 144 that also facilitate the lip 144 conforming to a contour of a cutaneous layer. In the embodiment shown in FIGS. 5A-5D, individual ends 140 may have a shoulder 146 that flares outwardly from the top portion 142 toward an arcuate waistline 148, an apron 150 including a conical flare between the waistline 148 and the lip 144, and flanks 152 including a panel in the shape of a five sided polygon. In the embodiment shown in FIG. 5A, individual flanks 152 extend from a tip at the top portion 142 to the lip 144, and extend from the shoulder and aprons 146 and 150 to a cutout 154. According to other embodiments, the ends 140 may have any suitable geometry that facilitates conformation of the lip 144 to the contours of individual target areas. For example, the shape of a typical human torso may vary between having a relative large radius of curvature, e.g., on the stomach or back, and having a relatively small radius of curvature, e.g., on the abdominal sides. Moreover, the size of a contour having an approximately consistent curvature may vary. Accordingly, an advantage of the present disclosure is the capability to provide flexible portions 100 with various geometries, e.g., shapes and sizes, to suitably conform to the cutaneous contours of individual target areas.

As shown in FIGS. 5A, 5B and 5C, the cutouts 154 (shown individually as cutouts 154a and 154b) are bounded by the flanks 152 of the ends 140, the central portion 120, and the connectors 160. The cutouts 154 receive the frames 300 (FIG. 3E) that, in turn, receive the rigid portions 200 as described herein.

According to certain embodiments of the present disclosure, the frames 300 (FIG. 3E) include rigid metal polygons, e.g., rectangles, around which the flexible portion 100 may be molded. Accordingly, the frames 300 may include a number of apertures, grooves, or other recesses into which the material of the flexible portion 100 may flow during a molding process to provide a strong, fluid-tight connection. Alternatively, the frames 300 can be adhered, welded or otherwise coupled to the flexible portion 100 in the openings 154. The frames 300 may also include materials other than metal, e.g., plastic, to which the rigid portions 200 can be secured. Alternatively, the flexible section can be clamped and/or bonded between two frames.

Each frame 300 (FIG. 3E) may be coupled to the cold plate 210 of an individual rigid portion 200 by any suitable fastener. For example, screws 302 (FIG. 3D) may extend through the apertures in the flange 212a (FIG. 4A) of the cold plate 210 and operably engage screw apertures (not shown) in the frame 300. Additionally, the frame 300 may be thermally coupled to the cold plate 210 via the flange 212a such that the TECs 230 may also transfer heat via the frame 300 from the subcutaneous lipid-rich cells.

Figure 6A:
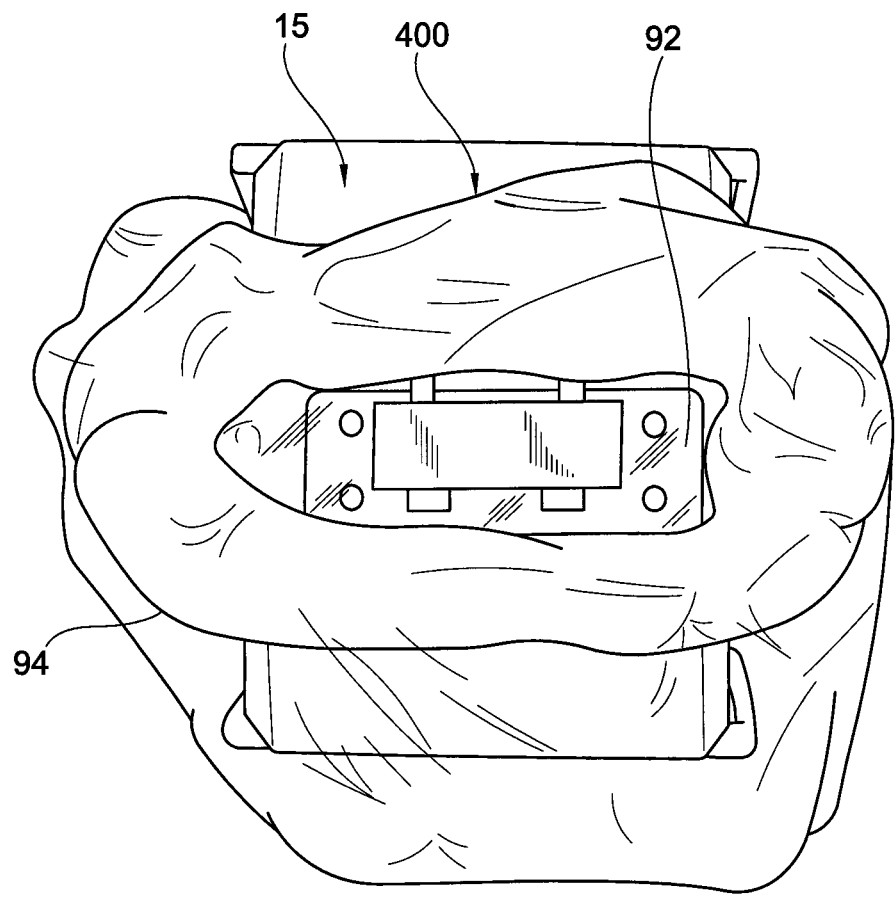
FIG. 6A is a perspective view showing an embodiment of a subject 11 liner for the treatment device shown in FIG. 3A.
Figure 6B:
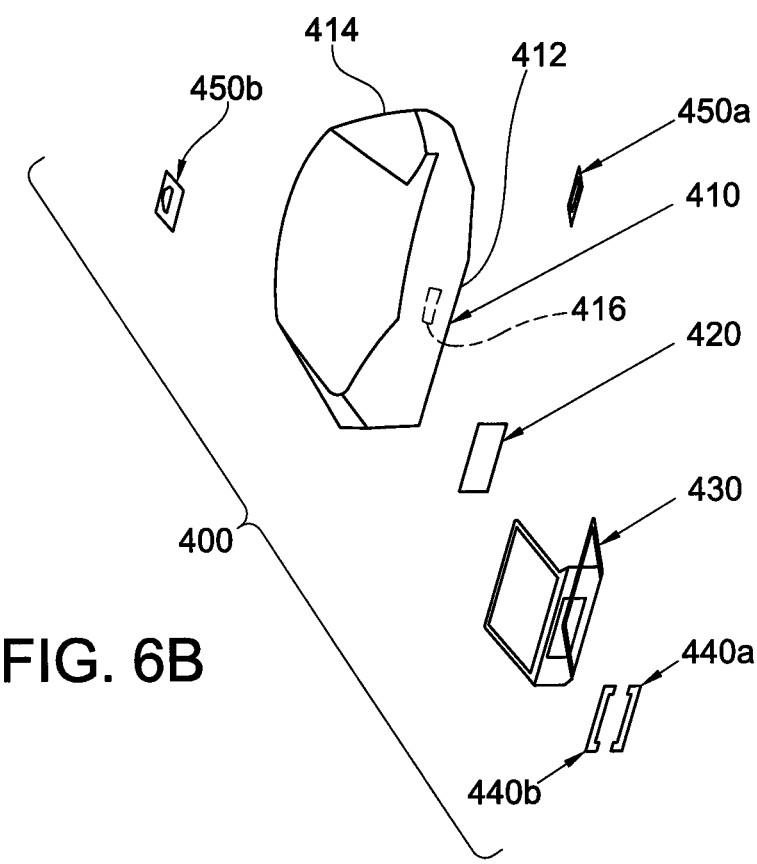
FIG. 6B is an exploded view of the subject 11 liner shown in FIG. 6A.
Figure 6C:
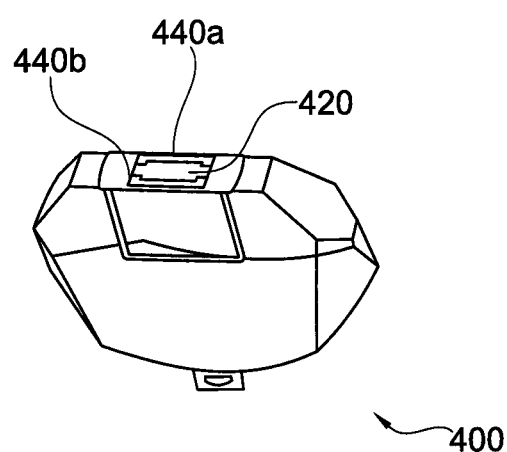
FIG. 6C is a perspective view of the subject 11 liner shown in FIG. 6A.

FIG. 6A is a perspective view showing a disposable liner 400 on the applicator 15. FIG. 6B is an exploded view of the liner 400 and FIG. 6C is a perspective view showing the liner of FIG. 6A. The liner 400 may be one embodiment of the interface layer 60 (FIG. 2) for providing a barrier between the treatment device 14 and a subject 11 receiving a treatment via the treatment device 14.

Referring to FIGS. 6A and 6B, a cup shaped liner film 410 includes a central portion 412 and a peripheral portion 414. The central portion 412 generally lies against the interior surface 92 of the applicator 15. The peripheral portion 414 is sized and shaped to be folded back over the exterior surface 94 (FIGS. 6A and 3D) of the applicator 15, the protective housing 260 (FIG. 3D) of the rigid portion 200, and/or the housing 14a of the treatment device 14. Accordingly, the liner 400 shields the treatment device 14 from contact with the subject 11 and/or a thermal coupling fluid, e.g., a cryoprotectant gel including a temperature depressant, and provides a sanitary barrier that is inexpensive and thus disposable. With appropriate ancillary treatment or by use of a different design or materials, liner 400 may serve as a sterile barrier.

Referring to FIG. 6B, one embodiment of the liner film 410 includes an 80 Shore A polyether urethane film that is approximately 0.002 inches thick. This film may be cut to shape and then the edges may be welded or adhesively sealed to form the desired cup shape. The liner film 410 can alternatively include materials such as polyethylene or other thin gauge films that are generally impermeable, are generally 0.001-0.006 inches thick so as avoid inhibiting heat movement from the subcutaneous lipid-rich cells, and have a Young's modulus of approximately 500-2,500 pounds per square inch (psi) to provide adequate elasticity.

The central portion 412 of the liner film 410 includes a hole or aperture 416 that aligns with the port 106 (FIGS. 5A, 5C and 5D) of the flexible portion 100 and the aperture 112 (FIG. 3C) of the mounting plate 110 when drawing a vacuum in the interior cavity 96. A membrane 420 is secured to the liner film 410 across aperture 416 to provide a selectively permeable barrier, e.g., a barrier that is generally permeable to air but is substantially impermeable to a thermal coupling material. The membrane 420 can include expanded polytetrafluoroethylene (ePTFE) or other hydrophilic or hydrophobic materials that have selective permeability. In the present example, membrane 420 includes ePTFE having a pore size in the range of approximately 0.1 to 10 microns that is bonded to a non-woven polyester backing (e.g., W.L. Gore & Associates, Flagstaff, Ariz., Part No. R10126). The periphery of the membrane 420 may be sealed to the central portion 412 by heat sealing, ultrasonic welding, adhesives, or any other suitable method that provides a fluid-tight coupling or joint.

A frame 430 may be coupled to the liner film 410 for shaping the central portion 412 of the liner film 410 in the vicinity of the flexible printed circuits 250 (FIG. 3D). The frame 430 may include a framework that generally corresponds to the shape and position of the frames 300 (FIG. 3E) along the interior surface 92 of the applicator 15. The frame 430 can include glycol-modified polyethylene terephthalate (PETG) or another material that can be bonded to the membrane 420 and liner film 410 on the central portion 412 by heat welding, ultrasonic welding, adhesives, or any other suitable method that provides a fluid-tight coupling or joint. Frame 430 may also serve to hold the liner film 410 taut over the flexible printed circuit 250 (FIG. 3D). Some embodiments according to the present disclosure may include a frame 430 that, along with the liner film 410, may be folded into a flattened arrangement that may facilitate packing one or more liners 400 in a container (not shown). Accordingly, the frame 430 may include segmentation perforations or one or more living hinges. Other embodiments according to the present invention may not include the framework corresponding to the frame 300 or other portions of a frame 430 shown in FIGS. 6B and 6C.

Magnetic or ferromagnetic strips 440 (shown individually as strips 440a and 440b) are coupled to the frame 430 for releasably attaching the liner 400 to the treatment device 14. The strips 440 may include a ferrous material and may be adhered on opposite sides of the aperture 416 using double sided tape (e.g., including acrylic adhesive 350) or another suitable adhesive for coupling strips 440 to frame 430 or liner film 410. The strips 440 cooperatively engage the magnets 116 on the mounting plate 110 to position and retain the liner 400 at the bottom of the cavity 96. Additionally, the strips 440 may be electrically conductive for closing a circuit (not shown) that detects the liner 440 is in position on the treatment applicator 14. Hang tabs 450 (shown individually as hang tabs 450*a* and 450*b*) may be coupled to the peripheral portion 414 of the liner film 410 for engaging cooperating features on treatment device 14 to retain the liner 440.

Referring to FIG. 6C, the convex side of the central portion 412 of the liner film 410 may be coupled to the membrane 420 and the frame 430 coupled over the membrane 420. Alternatively, the one or both of the membrane 420 and the frame 430 may be coupled on the concave side of the central portion 412, and/or the order in which the liner film 410, the membrane 420, and the frame 430 are coupled may be rearranged. The strips 440 are generally provided as the outermost layer on the convex side of the central portion 412 to facilitate their cooperation with the magnets 116, but the strips 440 may be coupled in other arrangements with respect to the liner film 410, the membrane 420, and the frame 430.

Figure 7D:
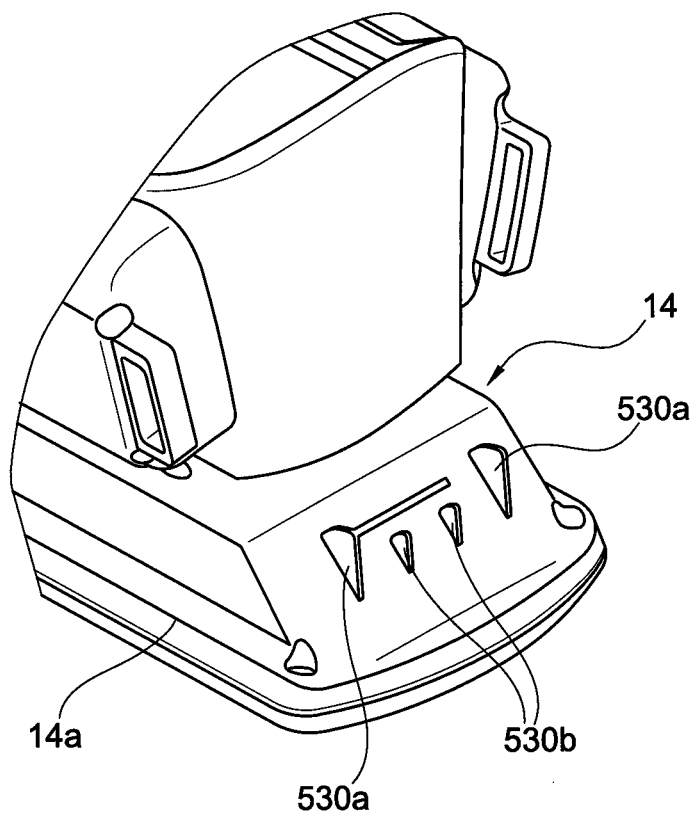
FIG. 7D shows another embodiment of a receptacle for the treatment device shown in FIG. 3A.
Figure 7E:
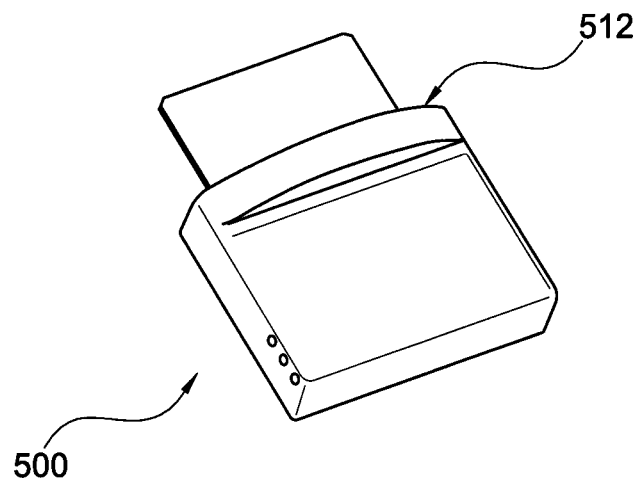
FIG. 7E shows another embodiment of a token for the treatment device shown in FIG. 3A.

FIG. 7A shows a token 500 interfacing with the treatment device 14. FIG. 7B shows a perspective view of the token 500 and FIG. 7C shows an embodiment of a receptacle 520 on the treatment device for receiving the token 500. FIG. 7D shows alternate receptacles according to another embodiment and FIG. 7E shows alternate token according to another embodiment. According to the embodiment shown in FIG. 7A, the interface between the token 500 and the treatment device 14 may provide a number of structural and/or functional advantages. The structural advantages may include, for example, preventing the token 500 from being incorrectly coupled to the treatment device and the functional advantages may include, for example, monitoring the system 10.

Referring to FIG. 7B, the token 500 includes an enclosure 510, a microelectronic device 520 disposed within the enclosure 510, and a set of contacts 530 that are electrically coupled to the microelectronic device 520 and extend from the enclosure 510. The enclosure 510 includes a first asymmetric mating feature 512. In the embodiment shown in FIG. 7B, the first asymmetric mating feature 512 includes a female recess 512*a* within a rim 512*b*. The set of contacts 530 may extend from the female recess 512*a*. As also shown in the embodiment of FIG. 7B, the shape of the rim 512*b* may include, for example, an arcuate side and three straight sides. Accordingly, the first asymmetric mating feature 512 in general and the shape of the rim 512*b* in particular are asymmetrical such that the enclosure 510 can matingly engage the receptacle 520 (FIG. 7C) in only one relative orientation. The asymmetrical mating feature 512 may be implemented adjacent to contacts 530 as shown in Figure B, or it may be implemented involving other portions of enclosure 510. Some embodiments according to the present disclosure may include a slot in the treatment device 14 that cooperatively receives some or all of the enclosure 510 in only one relative arrangement, e.g., to avoid or prevent inserting the token 500 into the slot in an unintended relative arrangement.

The microelectronic device 520 may include a microprocessor, memory, an input/output device, or combinations thereof that provide, for example, computing, storage, and/or communications. The microelectronic device 520 may, for example, meter the usage of the treatment device 14. According to some embodiments of the present disclosure, the microelectronic device 520 may count down from a predetermined limit. Use of the treatment device 14 is, accordingly, allowed when a non-zero number of counts remain and is prohibited when a zero number of counts remain prior to the intended use. The amount of treatments for which the treatment device 14 and/or system 10 can be used may be limited to an amount that is predetermined, e.g., pre-purchased by the system operator. Accordingly, when the microelectronic device 520 determines that the usage limit is reached, the microelectronic device 520 may communicate to the operator that it is necessary to obtain, e.g., purchase, additional treatments by replacing or replenishing the token 500. The token 500 may be replenished, for example, via the internet. Also, different operators may possess individual tokens 500 to monitor and limit their specific usage. The microelectronic device 520 may also, for example, store profiles of treatment parameters and limits. Examples of parameters may include identifying the body part that is to be targeted for treatment, the duration of a treatment, the number of cycles in a treatment, the heat extraction rate during a treatment, etc. Examples of limits that the microelectronic device 520 may store include, for example, limiting certain applicators, systems and/or operators in specific geographic regions to specific treatments.

The token 500 may also be used in conjunction with the treatment device 14 and the processing unit 24 (FIG. 2) to provide information about the system 10 (FIG. 2). For example, the token 500 may monitor the performance of the system 10, including storing a record of any system abnormalities, and/or to direct a prescribed maintenance schedule. When the token 500 is replaced or replenished, system information can be downloaded from the microelectronic device 520. The microelectronic device 520 can also be used to load software upgrades or operating parameters to the system 10 and provide new or modified profiles of treatment parameters.

The set of contacts 530 may provide a second asymmetric mating feature 532. In the embodiment shown in FIG. 7B, the second asymmetric mating feature 532 includes a first tab 532*a* and a second tab 532*b* that are different sizes. Accordingly, the tabs 532*a* and 532*b* are asymmetrical such that the set of contacts 530 can matingly engage the receptacle 520 (FIG. 7C) in only one relative orientation that also corresponds to the first asymmetric mating feature 512.

The set of contacts 530 can be located on only the first tab 532*a*, on only the second tab 532*b*, or distributed on both the first and second tabs 532*a* and 532*b*. Additionally, the set of contacts 530 can be located on only one face of the tabs 532*a* and 532*b*, on both faces of the tabs 532*a* and 532*b*, or a combination thereof. Moreover, the second asymmetric mating feature 532 may include more than one or two tabs.

Referring to FIG. 7C, the receptacle 520 provides the counterparts to the asymmetric mating features on the token 500. In the embodiment shown in FIG. 7C, the receptacle 520 includes a male projection 522 that is shaped and sized to be received in the female recess 512*a* of the token 500 (FIG. 7B) in only one relative orientation. Specifically, the male projection 522 may include, for example, an arcuate side and three straight sides that are the counterparts to the rim 512*b* on the token 500 (FIG. 7B). As also shown in the embodiment of FIG. 7C, the receptacle 520 includes a first slot 524*a* that is shaped and sized to receive the first tab 532*a* of the token 500 (FIG. 7B) and a second slot 524*b* that is shaped and sized to receive the second tab 532*b* of the token 500 (FIG. 7B). Accordingly, the first and second slots 524*a* and 524*b* receive the first and second tabs 532*a* and 532*b*, respectively, in only one relative orientation.

The receptacle 520 may also include a wiper 526 for wiping any material, e.g., a thermal coupling fluid such as a cryoprotectant gel including a temperature depressant, off the set of contacts 530 when they are being inserted into the receptacle 520. The wiper 526 may include, for example, a flap or another projection that is biased into contact with the set of contacts 530 so as to squeegee the material off the set of contacts 530. Removing such material from the set of contacts 530 may avoid or eliminate interference in electrically connecting with the set of contacts 530 and protect the interior electronics from electrical shorts or corrosion.

The asymmetric mating features on the enclosure 510 and their counterparts on the receptacle 520 may help to avoid contaminating the interface between the token 500 and the treatment device 14. For example, when the token 500 and the treatment device 14 are interfaced, the enclosure 500 and the receptacle 520 overlap one another such that debris would have to follow a tortuous path including moving over the rim 512*b*, between the rim 512*b* and the male projection 522, across the top of the male projection 522, and into the first and/or second slots 524*a* and 524*b*. Additionally, the male projection 522 may help to avoid contamination when the token 500 and the treatment device 14 are not interfaced because debris would have to climb the male projection 522 before entering the first and/or second slots 524*a* and 524*b*.

Other embodiments in accordance with the present disclosure may include reversing certain members. For example, the rim and female recess may be provided on the treatment device 14 and the male projection may extend from the token 500. Also, the set of contacts may project from the treatment device 14 and the token 500 can include the counterpart connection(s) for electrically engaging the set of contacts.

The curved sides of the rim and male projection may be oriented to shed debris. Orienting convex surfaces upward in a nominal arrangement of the treatment device 14, e.g., with the treatment device 14 sitting on the control panel 14*b* (FIG. 3B) and the applicator 15 extending upward, may tend to shed debris rather than allowing it to collect on a flat or concave surface.

Referring to FIG. 7D, the housing 14*a* may include one or more types of guides 530 (shown individually as guides 530*a* and 530*b*) to assist in orienting and inserting the token (not shown) into the treatment device 14. For example, the guides 530 may be desirable for orienting and inserting the token 500 perpendicular to a surface of the housing 14*a*.

Referring to FIG. 7E, a single asymmetric mating feature may be provided to ensure that the token 500 correctly interfaces with the treatment device 14. For example, a single tab may be implemented in lieu of the second asymmetric mating feature 532 (FIGS. 7B and 7C). Accordingly, the first asymmetric mating feature 512 (also FIGS. 7B and 7C) may provide sufficient asymmetry to ensure that the token 500 is not incorrectly inserted into the treatment device 14.

Other embodiments in accordance with the present disclosure may include interfacing the token 500 with other features of the treatment system 10. For example, the receptacle 520 for the token 500 may be disposed on the processing unit 24, the input device 28, the output device 30, or elsewhere disposed on the cart 34 (FIG. 1). Receptacles 520 for matingly engaging the token 500 may also be provided at multiple locations on the treatment system 10, including on the treatment device 14.

Embodiments of some applicators according to the present disclosure include variable geometry cooling panels. For example, the number and relative arrangement of the cooling panels may be varied to position panels closer together or in various relative orientations.

Figure 7F:
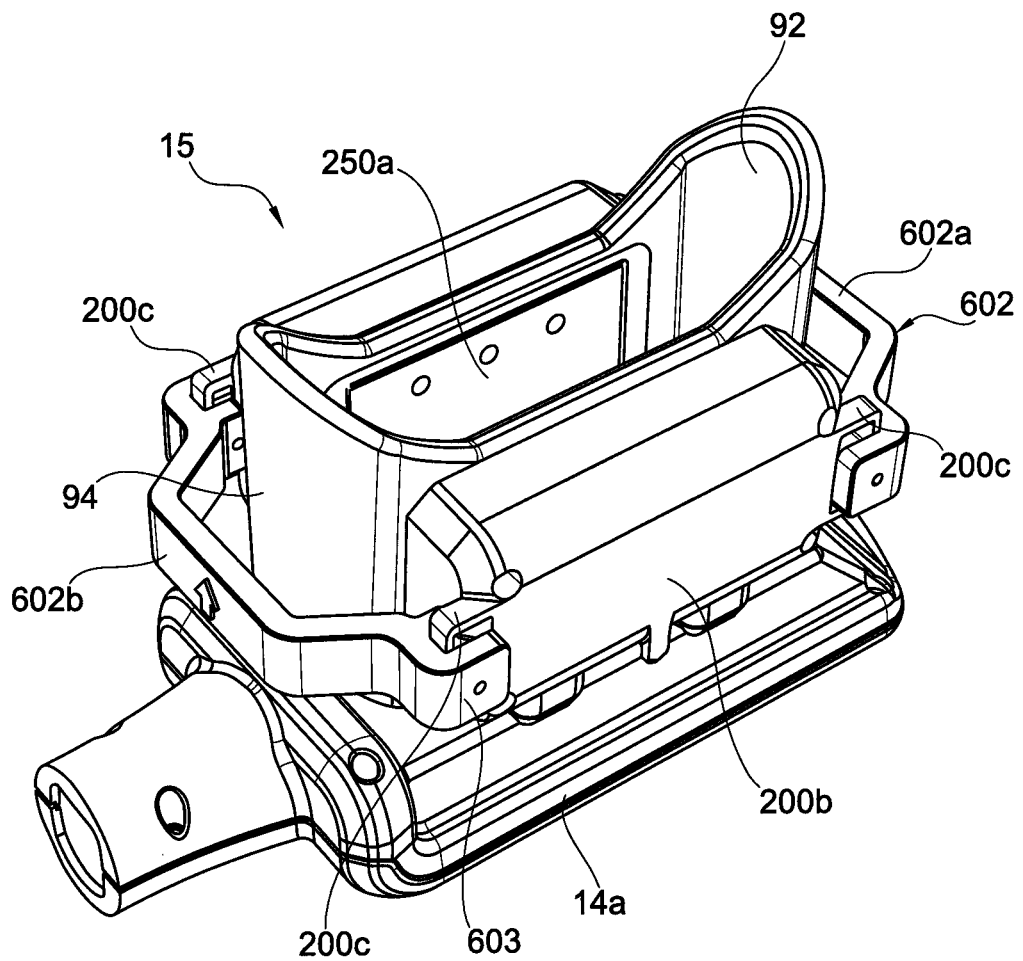
FIG. 7F shows an adjustor for the treatment devices described herein.

Referring to FIG. 7F, an adjustor 600, here shown as clamp 602, is depicted. It may be advantageous for particular treatment regimens to adjust the dimensions of the interior cavity 96, e.g., the shape of the contour, the distance between facing portions of flexible portion 100, and/or facing portions 250*a* and 250*b* (not shown) of the flexible printed circuit 250 in interior cavity 96, etc., when tissue is drawn into the applicator 15 during treatment. According to some embodiments of the present disclosure, the adjustor 600 shapes, sizes, fixes, or controls the dimensions of the interior cavity 96 to help ensure greater uniformity of cooling or heat extraction from the subcutaneous lipid-rich tissue that is drawn into the interior cavity 96 by vacuum during treatment. Such uniformity may be accompanied by improved efficiency of treatment and greater and/or more uniform selective damage, injury or disruption of the affected subcutaneous lipid-rich tissue. A distance between opposite faces of the interior cavity 96, or gap width, of between approximately 0.5 and 3 or more inches may be desired. Alternatively, a gap width of between approximately 1.0 and 2.0 inches, or alternatively approximately 1.5 inches, may be desired.

In the embodiment of FIG. 7F, clamp 602 includes first clamp portion 602*a* and second clamp portion 602*b* having a fixed length that corresponds to the desired gap width. Two receiving portions 603 on each of first and second clamp portions 602*a* and 602*b* are affixed to two tabs 200*c* on each of panels 200*a*, 200*b* by screws, adhesive, welding, etc., or it may be integrally formed with panels 200*a*, 200*b*. Any suitable material, such as a metal, polymeric or other material to include cast urethane, may be used for clamp 602. An advantage of clamp 602 in the configuration shown in FIG. 7F is that it allows the lips (edges) of flexible portion 100 to remain flexible, in turn allowing the contour of applicator 15 to conform to different subject 11 body sizes and/or geometries. Other clamp 602 configurations may be used to affect the desired gap width control.

The adjuster 600 may be affixed to applicator 15 during the manufacturing or assembly process prior to treating a subject 11. This ensures that as tissue of the subject 11 is drawn into the interior cavity 96 of flexible portion 100, the desired gap width is achieved. Alternatively, adjuster 600 may be temporarily affixed to applicator 15 so that an operator, such as a physician, may adjust the dimensions of the interior cavity 96 either before or after tissue has been drawn into the interior cavity 96. The adjuster 600 may additionally or alternatively include clips, drawstrings, or other mechanisms suitable for reshaping and/or resizing the interior cavity of the applicator. The adjuster 600 may adjust any dimension of the cavity and is not limited to a single dimension. Some embodiments according to the present disclosure may include at least one insert that may be introduced into the interior cavity of the applicator to change at least one internal dimension of the cavity.

Embodiments of some applicators according to the present disclosure include variable orientation cooling panels. For example, cooling panels on opposite sides of a vacuum cup can be oriented in a splayed-out arrangement when applied to a relatively large tissue segment, and in a narrowed arrangement, e.g., with the cooling plates arranged roughly parallel to one another, when applied to a relatively small tissue segment. Two clamps 602, e.g., one located nearer the contour mouth and one nearer the vacuum port 106 (FIGS. 5A, 5C and 5D), may provide adjustable gap width control and/or controlling the relative cooling plate angle. The system 10 may include sensors (not shown) to sense the adjuster position or adjusted dimensions of the interior cavity 96, the gap width, and/or cooling plate angle and use this information to modify one or more treatment parameters available for selection by a practitioner, e.g., to ensure consistent performance for the cavity dimensions selected by the practitioner.

Spacing and orienting the cooling panels between different arrangements may be used to reduce patient discomfort and affect the degree of tissue cooling that can be achieved within a treatment cycle. For example, the splayed-out arrangement of the cooling panels maintains a large enough mouth to allow tissue to pass easily into the cup and be drawn along the cooling panels for treatment without causing a high degree of patient discomfort. On the other hand, the narrowed arrangement provides faster cooling and shorter treatments to also decrease patient discomfort. Accordingly, angling or fluting the cup geometry may be used to optimize the time required to achieve sufficient cooling for subcutaneous fat layer reduction. Further, cooling tissue more quickly allows longer treatment times that, along with shorter treatment times, allows a practitioner to vary the dosage and thereby control efficacy in a single treatment cycle.

Additionally, a flared edge or taper on the cup edge may reduce the friction that the pad/liner/tissue experience when vacuum pressure is applied and they are drawn up into the applicator cup. A flare may also reduce a "pinch" point where an edge of the applicator comes into contact with the patient's soft tissue causing discomfort and potential bruising after the treatment.

According to a further embodiment, the token 500 and the treatment device 14 may each have corresponding arrangements that allow any relative orientation to be used for mating engagement. For example, the token 500 may include a symmetrical enclosure that can interface with the treatment device 14 in any of a plurality of relative orientations, and redundant sets of contacts may be distributed such that the proper electrical connections may be completed in any of the plurality of relative orientations.

In operation, an embodiment according to the present disclosure may include preparing a target area for treatment by topically applying to the patient's skin a pad, e.g., Webril® manufactured by Kendall, which is saturated with thermal coupling fluid such as a cryoprotectant gel including a temperature depressant. The treatment device 14 is prepared by positioning the central portion 412 of a liner 400 in the interior cavity 96 with the strips 440 cooperatively engaging the magnets 116, folding the peripheral portion 414 of the liner 400 over the exterior surface 94 of the applicator 15, and coupling the hang tabs 450 to treatment device 14. A token 500 is interfaced with the treatment device 14, the treatment device is positioned over the pad on top of the target area of the patient's skin, and a treatment may be initiated using at least one of the control pad 14b and the touch screen 28.

Figure 8:
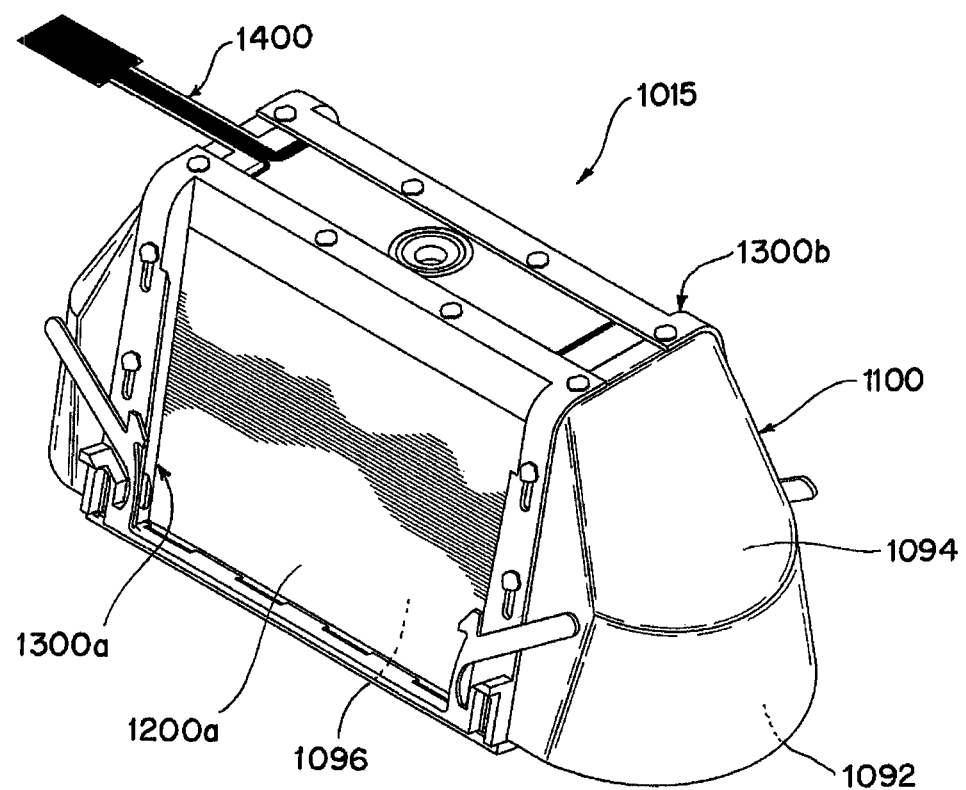
FIG. 8 is a perspective view showing an embodiment of another applicator for a treatment to remove or extract heat from lipid-rich cells disposed under a cutaneous layer.

FIG. 8 is a perspective view showing a vacuum applicator 1015 for a treatment to remove heat from subcutaneous lipid-rich cells in accordance with another embodiment of the technology. The vacuum applicator 1015 may have a generally rectangular top face and a bottom face including parallel sides and elliptical ends. In the illustrated embodiment, the vacuum applicator 1015 has an interior surface 1092 and an exterior surface 1094. The interior surface 1092 defines an interior cavity 1096 in which a vacuum is drawn. The vacuum applicator 1015 may further include a flexible portion 1100 and at least one rigid portion including at least one panel 1200 (the embodiment of FIG. 8 includes individual panels 1200a and 1200b, however, only panel 1200a is shown in FIG. 8) and at least one frame 1300 (the embodiment shown in FIG. 8 includes individual frames 1300a and 1300b). In operation, a disposable patient protection device (PPD) 1400 may be used in conjunction with the vacuum applicator 1015.

Figure 9A:
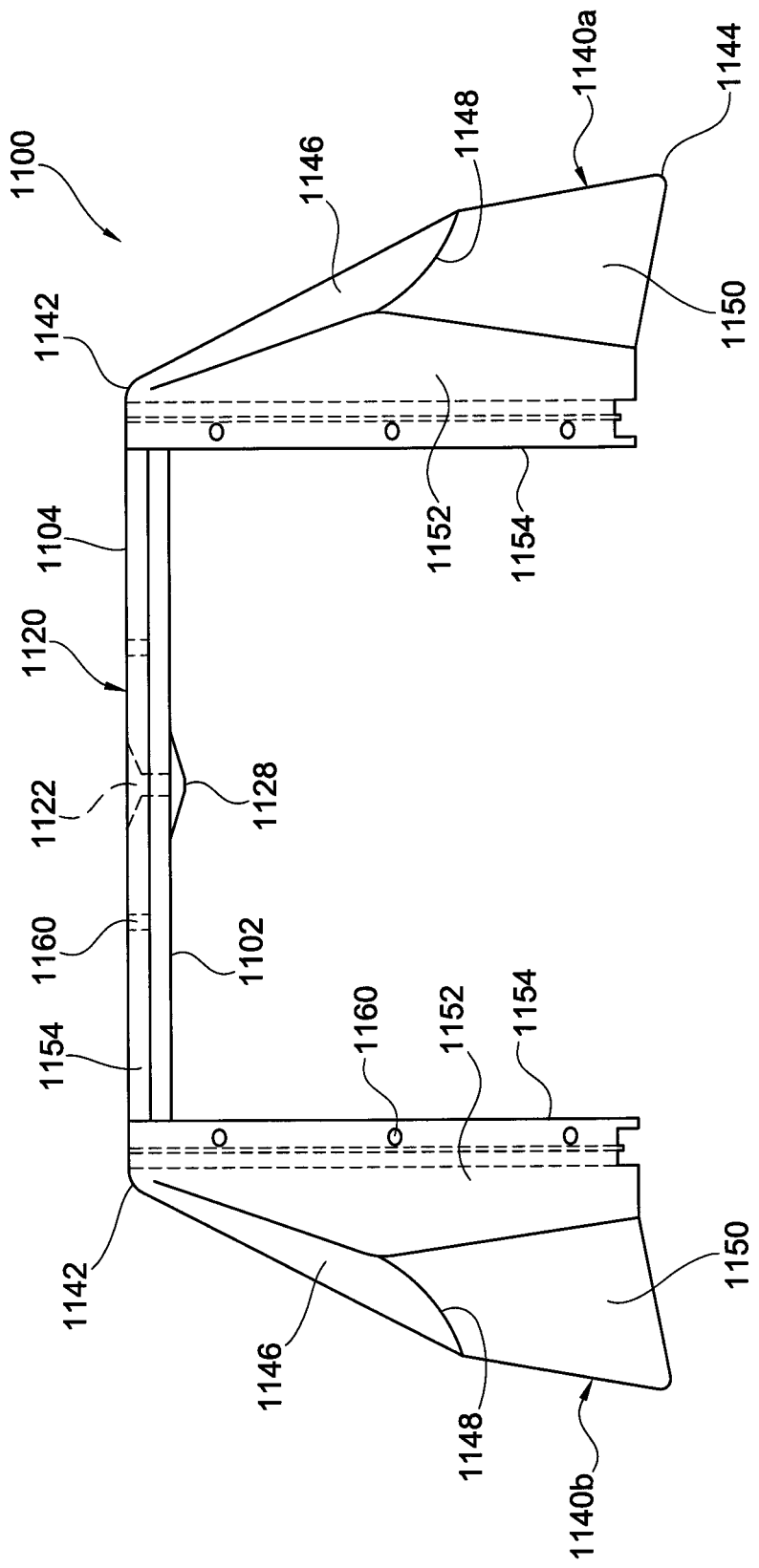
FIG. 9A is an elevation view of a flexible portion of the applicator shown in FIG. 8.
Figure 9B:
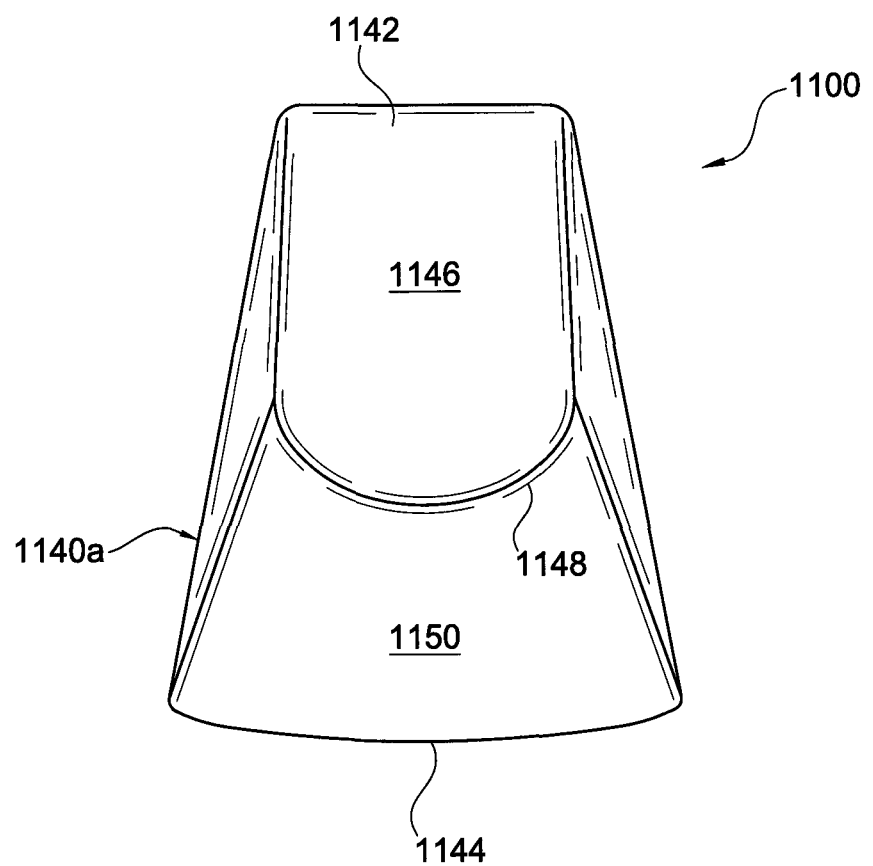
FIG. 9B is a side view of a flexible portion of the applicator shown in FIG. 8.
Figure 9C:
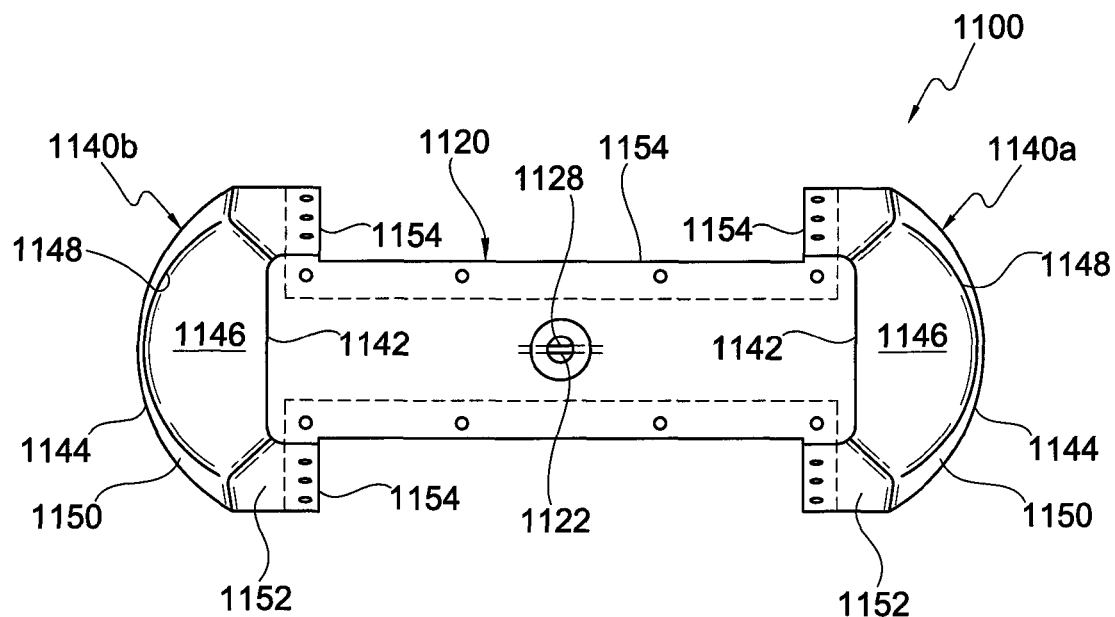
FIG. 9C is a plan view of a flexible portion of the vacuum applicator shown in FIG. 8.
Figure 9D:
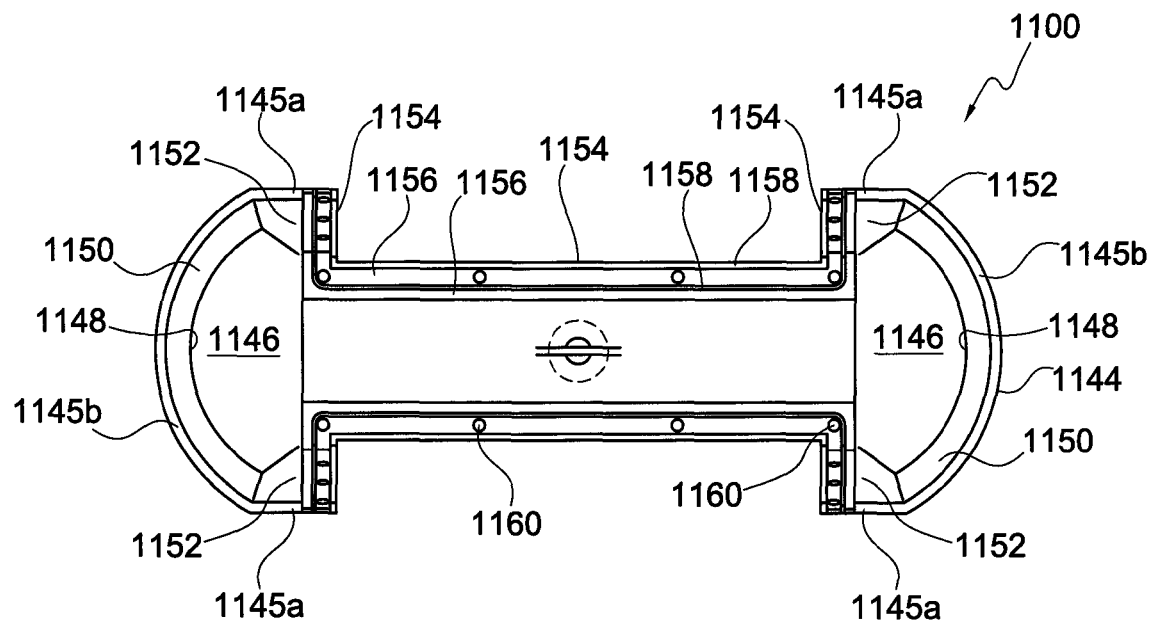
FIG. 9D is a bottom view of a flexible portion of the vacuum applicator shown in FIG. 8.

FIG. 9A is a front view of an embodiment of the flexible portion 1100 of the vacuum applicator 1015. FIG. 9B is an end view, FIG. 9C is a top view, and FIG. 9D is a bottom view of the flexible portion 1100 shown in FIG. 9A. The flexible portion 1100 can be molded from an elastically deformable plastic, e.g., silicone, or another material that is suitably flexible. The flexible portion 1100 may be transparent to facilitate viewing the skin through the flexible portion 1100. In other embodiments, the flexible portion 1100 can be translucent or opaque.

Referring to FIG. 9A, the flexible portion 1100 includes a central portion 1120, ends 1140 (shown individually as ends 1140a and 1140b), an interior surface 1102, and an exterior surface 1104. The flexible portion 100 may also include a port 1122 having an obstruction 1128 that partially occludes the port 1122 to inhibit the skin or another solid structure from entering the port 1122 while permitting air or other fluids to pass through the port 1122.

Referring to FIGS. 9A and 9B, each end 1140 has a top portion 1142 extending from the central portion 1120. The ends 1140 and central portion 1120 can be integrally molded or separate components. As best shown in FIGS. 9A, 9B and 9D, each end 1140 has a lip 1144 at the bottom, i.e., opposite from the top portion 1142. The lip 1144 may have a three dimensional geometry to facilitate conforming to a contour of a cutaneous layer (not shown in FIGS. 9A-9D). For example, with particular reference to FIG. 9D, a nominal configuration of the lip 1144 may include straight segments 1145a, arcuate segments 1145b, or a combination of both when viewed from above or below. Concurrently, with particular reference to FIG. 9B, the nominal configuration of the lip 1144 may include an arcuate profile view, and with particular reference to FIG. 9A, the frontal view of the nominal configuration of the lip 1144 may include a downward slant with respect to the central portion 1120. According to other embodiments, lip 1144 may have different geometries suitable for conforming to the contours of given cutaneous layers.

The individual ends 1140 may have overall geometries between the top portion 1142 and the lip 1144 that also facilitate the lip 1144 conforming to a contour of a cutaneous layer. In the embodiment shown in FIGS. 9A-9D, individual ends 1140 may have a shoulder 1146 that flares outwardly from the top portion 1142 toward an arcuate waistline 1148, an apron 1150 including a conical flare between the waistline 1148 and the lip 1144, and flanks 1152 including a panel in the shape of a five sided polygon. In the embodiment shown in FIG. 9A, individual flanks 1152 extend from a tip at the top portion 1142 to the lip 1144, and extend from the shoulder and aprons 1146 and 1150 to a periphery 1154. According to other embodiments, the ends 1140 may have any suitable geometry that facilitates conformation of the lip 1144 to the contours of individual cutaneous layers. For example, the shape of a typical human torso may vary between having a relative large radius of curvature, e.g., on the stomach or back, and having a relatively small radius of curvature, e.g., on the abdominal sides. Moreover, the size of a contour having an approximately consistent curvature may vary. Accordingly, an advantage of the present disclosure is the capability to provide flexible portions 1100 with various geometries, e.g., shapes and sizes, to suitably conform to the contours of individual cutaneous layers.

As shown in FIGS. 9A, 9C and 9D, the periphery 1154 extends up the flank 1152 of the end 1140a, across the central portion 1120, and down the flank 1152 of the end 1140b. The periphery 1154 may include grooves 1156 (FIG. 9D) and/or ribs 1158 (FIG. 9D) that provide the flexible portion 1100 with a fluid tight seal. The periphery 1154 may also include a plurality of apertures 1160 for coupling the flexible portion 1100 to one or more rigid portions 1200. The periphery 1154 accordingly defines a cutout from the flexible portion 1100, and the cutout receives an individual rigid portion.

Figure 10:
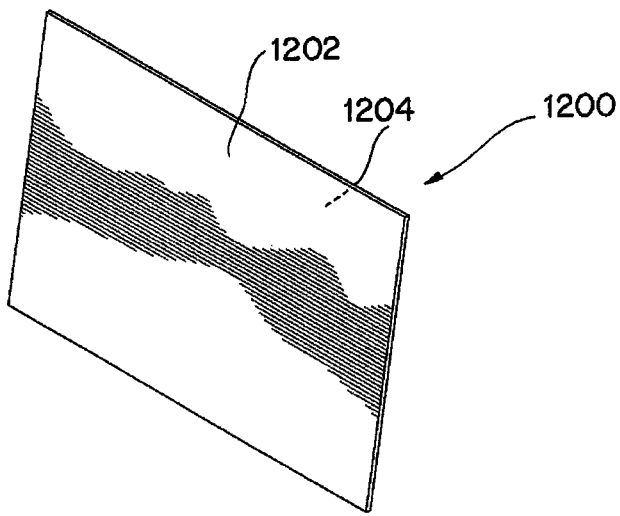
FIG. 10 is a perspective view of a panel of a rigid portion of the vacuum applicator shown in FIG. 8.

FIG. 10 shows a perspective view of an embodiment of the panel 1200 for the rigid portion of vacuum applicator 1015. The panels 1200 resist deformation and are thermally conductive to provide a consistent mechanical and thermal interface between the cooling plates (not shown in FIG. 10) and the subject 11. In the embodiment shown in FIG. 10, the panels 1200 may be an aluminum panel having an interior surface 1202 and an exterior surface 1204. In other embodiments, the panels 1200 may include other materials that are suitably rigid and thermally conductive. The panels 1200 resist deformation, such as bowing, while a vacuum is drawn in the interior cavity 1096 to maintain an uninterrupted thermal path between the cooling plates 50 (FIG. 2) and the subject 11. More specifically, deformation of the panels 1200 could cause the vacuum applicator 1015 to separate from the cooling plates 50 and thereby reduce the ability of the cooling plates 50 to draw heat from the interior cavity 1096 of the vacuum applicator 1015. The panels 1200 may be coupled to the flexible portion 1100 with individual frames 1300.

Figure 11A:
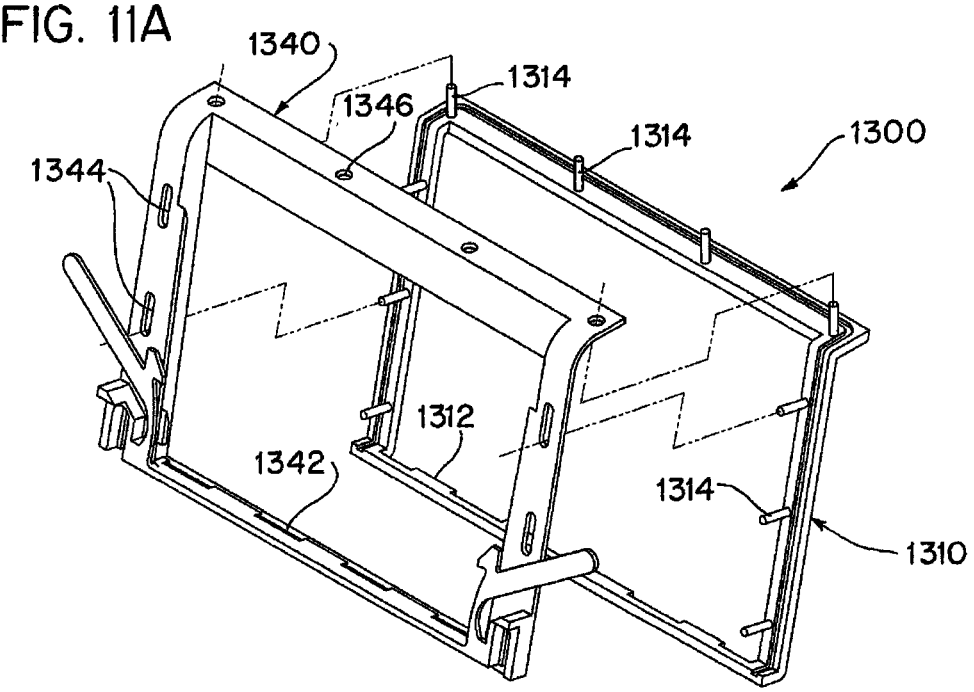
FIG. 11A is an exploded perspective view a frame of the vacuum applicator shown in FIG. 8.

FIG. 11A shows an exploded perspective view of an embodiment according to the present disclosure of an individual frame 1300 of the vacuum applicator 15. The individual frame 1300 may include a first frame portion 1310 and a second frame portion 1340. In the embodiment shown in FIG. 11A, the first frame portion 1310 may have a plurality of tabs 1312 and/or pins 1314 that may be received in corresponding recesses 1342, slots 1344 and/or apertures 1346 of the second frame portion 1340 to secure the first and second frame portions 1310 and 1340 together. For example, tips of the pins 1314 may subsequently be deformed, e.g., by heating and pressing, to prevent the pins 1314 from disengaging the slots 1344 and/or apertures 1346. In other embodiments, screws or any suitable fasteners may be used for securing together the first and second frame portions 1310 and 1340.

Figure 11B:
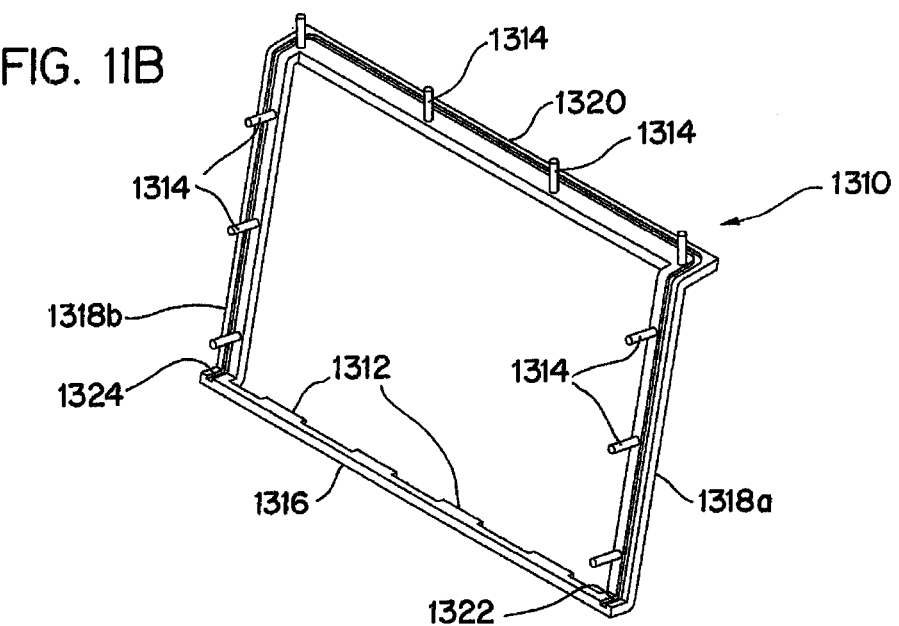
FIG. 11B is a perspective view of a first frame portion of the frame shown in FIG. 11A.

FIG. 11B shows a perspective view of an embodiment of the first frame portion 1310. In the embodiment shown in FIG. 11B, the first frame portion 1310 has a generally rectangular configuration that includes a bottom bar 1316, two side bars 1318a and 1318b, and a top bar 1320. Individual tabs 1312 can project from the bottom bar 1316, and individual pins 1314 may project from the side bars 1318a and 1318b and from the top bar 1320. In the embodiment shown in FIG. 9B, the side bars 1318a and 1318b and the top bar 1320 may include grooves 1322 and/or rib 1324 that provide the first frame portion 310 with a fluid tight seal.

Figure 11C:
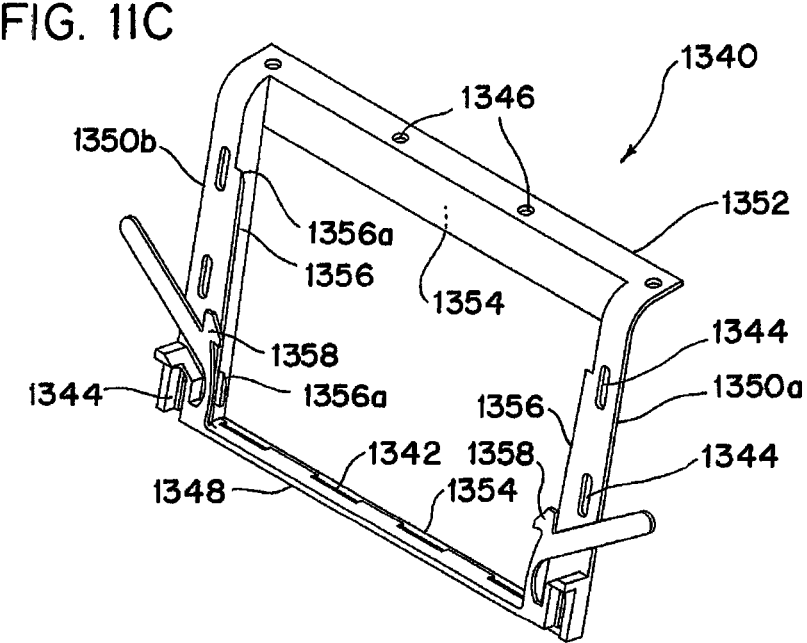
FIG. 11C is a perspective view of a second frame portion of the frame shown in FIG. 11A.

FIG. 11C shows a perspective view of an embodiment according to the present disclosure of the second frame portion 340. In the embodiment shown in FIG. 11C, the second frame portion 1340 may have a generally rectangular configuration including a bottom bar 1348, two side bars 1350a and 1350b, and a top bar 1352. Individual recesses 1342 may be formed in the bottom bar 1348, and individual slots 1344 and/or apertures 1346 may be formed in the side bars 1350a and 1350b and in the top bar 1352. The bottom bar 1348, side bars 1350a and 1350b, and top bar 1352 may mutually define a rectangular surface 1354 surrounding an opening 1354a. The individual side bars 1350 may include one or more cams 1356 that may have inclined surfaces 1356a. The individual side bars 1350 may also include individual latches 1358. In the embodiment shown in FIG. 11C, individual latches 1358 are positioned on individual side bars 1350, e.g., on opposite sides of the opening 1354a, and individual cams 1356 are positioned on confronting lateral sides of the individual side bars 1350.

Several embodiments of the frame 1300 may provide a fluid tight coupling joining the flexible portion 1100 and the panels 1200. This feature may reduce or eliminate leaks that could adversely affect drawing a vacuum in the vacuum applicator 1015. Additionally, the cams 1356 on an individual frame portion 1340 may drive the cooling plates 50 against the panels 1200. The frames 1300 may accordingly provide consistent, uninterrupted thermal contact between the cooling plates 50 and the vacuum applicator 1015 for controlled cooling of the subject 11. Further, the latches 1358 on the second frame portions 1340 may releasably retain the cooling plates 50 with respect to the vacuum applicator 1015 to quickly and easily detach the cooling plates 50 from the panels 1200. This design has the additional benefit of allowing flexible portion 1100 having a different profile or geometry to suit or match particular subject 11 body shapes or profiles. Alternatively, rather than two frame portions 1310 and 1340, the same or a similar functionality may be achieved with a single frame portion (not shown) that is bonded, heat staked, insert molded, or otherwise affixed into flexible portion 1100.

Figure 12A:
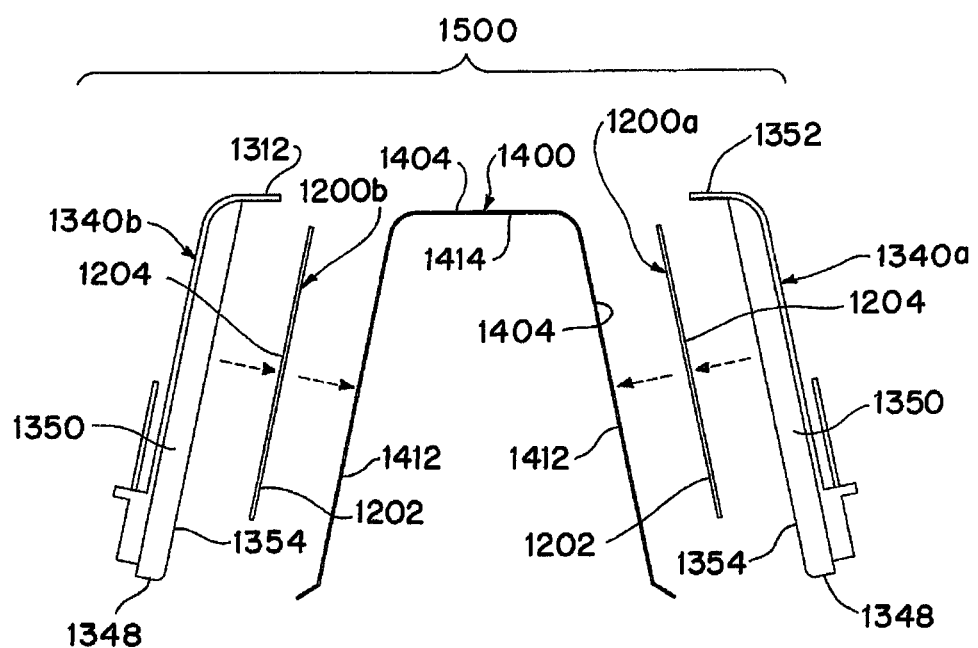
FIG. 12A is an exploded side view of a subassembly of the vacuum applicator shown in FIG. 8 including the panels and the second frame portions.

The assembly of an embodiment according to the present disclosure of a vacuum applicator 1015 will now be described with respect to FIGS. 12A and 12B. FIG. 12A is an exploded view of an embodiment of a subassembly 1500 of the vacuum applicator 1015. The subassembly 1500 may include the panels 1200 (the embodiment shown in FIG. 12A includes individual panels 1200a and 1200b) and the second frame portions 1340 (the embodiment shown in FIG. 12A includes individual frame portions 1340a and 1340b). The individual rectangular surfaces 1354 of the second frame portions 1340 overlay the individual exterior surfaces 1204 of individual panels 1200 and may be secured thereto, e.g., with an adhesive. The exterior surfaces 1204 of the panels 1200 are exposed by the openings 1354a in the second frame portions 1340 to engage the cooling plates 50 (FIG. 2).

FIG. 12B is an exploded view showing an embodiment of a relationship of the flexible portion 1100, the first frame portion 1310, and the subassembly 1500. The first frame portion 1310 is positioned with respect to the flexible portion 1100 such that (1) individual pins 1314 on the first frame portion 1310 may project through individual apertures 1160 in the flexible portion 1100, and (2) the grooves 1322 on the top bar 1320 of the first frame portion 1310 may form a fluid tight seal with the ribs 1158 on the periphery 1154 of the flexible portion 1100. The subassembly 1500 is then positioned on the flexible portion 1100 such that individual pins 1314 on the first frame portion 1310 are received in individual slots 1344 and/or apertures 1346 of the second frame portion 1340. The second frame portion 1340 is moved with respect to the first frame portion 1310 such that individual tabs 1312 on the bottom bar 1316 of the first frame portion 1310 engage in individual recesses 1342 on the bottom bar 1348 of the second frame portion 1340. The tips of the pins 1314 may subsequently be deformed, e.g., by heating and pressing, to prevent the pins 1314 from pulling out of the slots 1344 and/or apertures 1346. Accordingly, the frames 1300 provide a fluid-tight connection between the flexible portion 1100 and the panels 1200. The lips 1144 of the flexible portion 1100 in combination with the panels 1200 and the bottom bar 1348 of the second frame portion 1340 define a vacuum applicator aperture for contiguously engaging the skin 70 during a treatment.

Figure 13A:
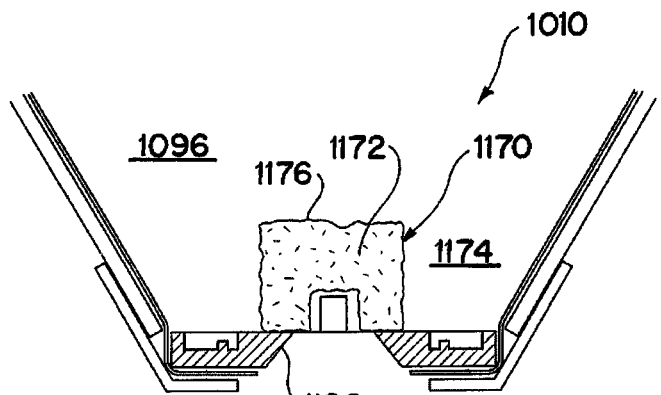
FIG. 13A is a cross-section view showing an embodiment of a fluid separator in fluid communication between an interior cavity and a port of the vacuum applicator shown in FIG. 8.

FIG. 13A is a cross-section view showing an embodiment of a fluid separator 1170 in fluid communication between the interior cavity 1096 and the port 1122 of the vacuum applicator 1015. In the embodiment shown in FIG. 13A, the fluid separator 1170 includes a pad 1172, e.g., a foam pad, through which a gaseous fluid may flow but through which a liquid or gel flow is avoided. A moat 1174 may be formed in a gap between the pad 1172 and the interior surface 1012 of the vacuum applicator 1015. The moat 1174 may provide a holding space for excess liquid or gel so as to make available a relatively liquid or gel free path through a top surface 1176 of the pad 1172 if the vacuum applicator 1015 were to be inverted such that the aperture 1018 was disposed above the pad 1172.

Figure 13B:
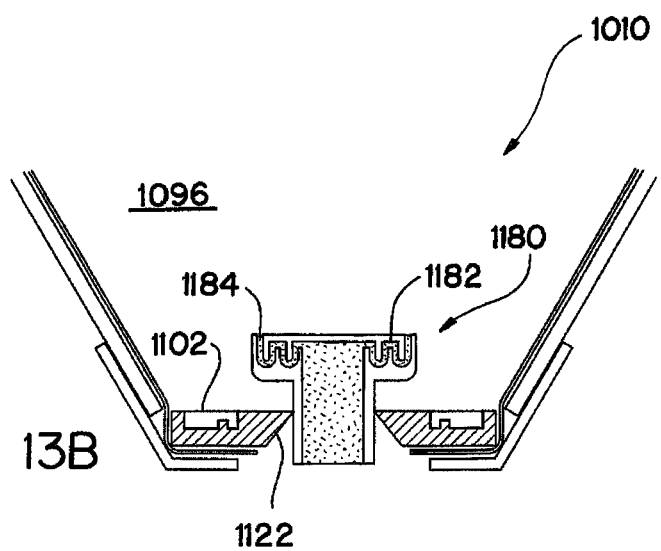
FIG. 13B is a cross-section view showing another embodiment of a fluid separator in fluid communication between an interior cavity and a port of the vacuum applicator shown in FIG. 8.

FIG. 13B is a cross-section view showing another embodiment of a fluid separator 1180 in fluid communication between the interior cavity 1096 and the port 1122 of the vacuum applicator 1015. In the embodiment shown in FIG. 13B, the fluid separator 1180 includes a torturous path 1182, e.g., a labyrinth, through which a gaseous fluid may flow but through which a liquid or gel flow is avoided. An opening 1184 to the torturous path 1182 may be positioned in the interior cavity 1096 spaced from the interior surface 1102 so as to avoid ingesting a liquid or gel into the torturous path 1182.

Figure 14:
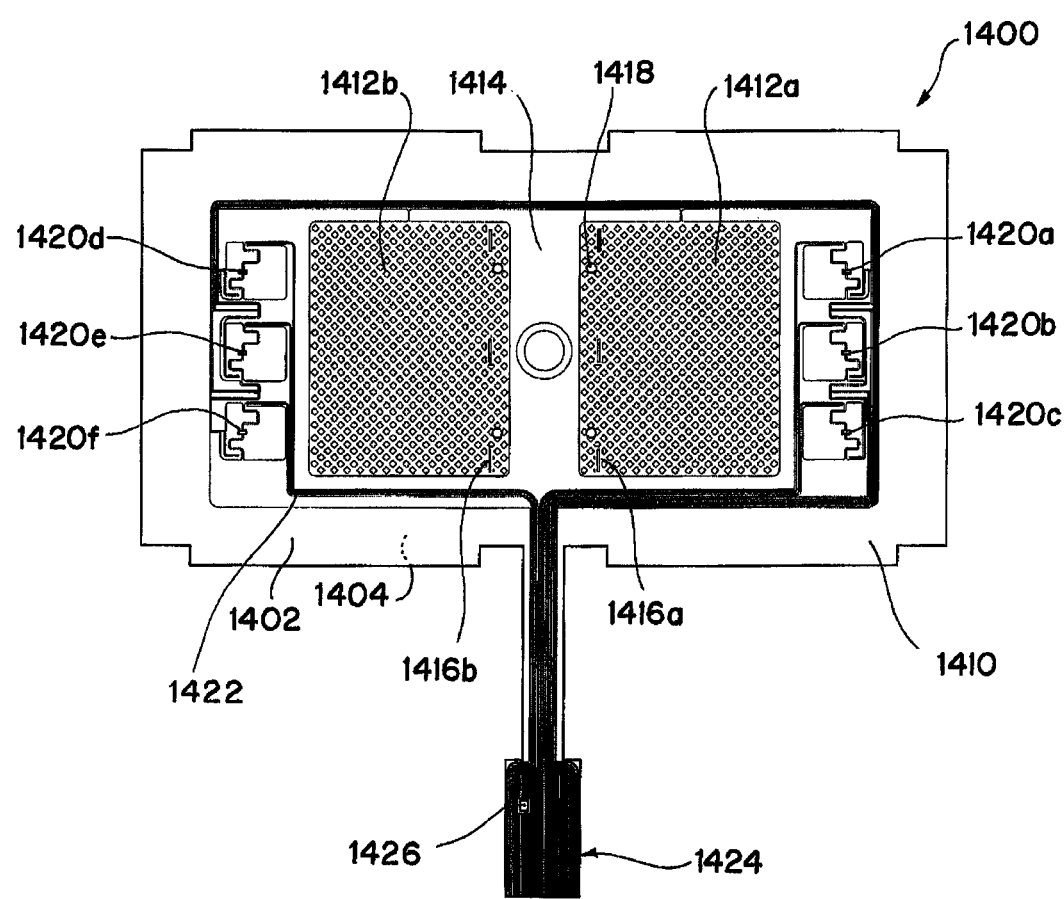
FIG. 14 is a plan view of a personal protection device usable with a vacuum applicator in accordance with an embodiment of the disclosure.

FIG. 14 shows a plan view of an embodiment according to the present disclosure of the PPD 1400. The PPD 1400 is one example of the interface layer 60 (FIG. 2) positioned between the vacuum applicator 1015 and the skin 70 of a subject. The PPD 1400 includes a substrate 1410 having a first surface 1402 for contacting the skin 70 of the subject 11 and a second surface 1404 that faces opposite the first surface 1402. The flexible PPD 1400 may be releasably attached to the vacuum applicator 1015 to be disposed of following a treatment.

The PPD 1400 may include temperature sensors 1420 (the embodiment shown in FIG. 14 includes individual temperature sensors 1420a-1420f) such as thermisters. The signals output from the temperature sensors 1420 can be electrically coupled via conductive traces 1422 to an output connector 1424. According to other embodiments, the signals output from the temperature sensors 1420 can be transmitted wirelessly rather than via the conductive traces 1422. As shown in FIG. 14, the PPD 1400 may also have a microelectronic device 1426. The microelectronic device 1426 may be electrically coupled to the signals output from the temperature sensors 1420 and provide, for example, storage, computing, and/or communications for the output signals.

Embodiments of the applicators 15 and 1015 according to the present disclosure include lips 144 and 1144, respectively, which define at least a portion of the contour that contacts the skin 70 of the subject 11. Contact may be via an interposed pad, e.g., Webril® manufactured by Kendall, which may be saturated with a gel. The shape of the contour should fit easily around a discrete tissue segment that has been identified for treatment. Longitudinal ends of the contour; also referred to as lips 144 with regard to the embodiment shown in FIGS. 5A-5D, may be shaped like ears to correspond to a curved body contour, e.g., the flank of a torso also referred to as a "love handle" area of the body. An approximately air-tight seal may be made between the applicator 15 or 1015 and the pad/skin surface if the contour closely fits the body contour without applying undo force to press the applicator 15 or 1015 against the subject 11. The approximately air-tight seal and the vacuum pressure in the interior cavity 96 or 1096 of the applicator 15 or 1015 act on the subcutaneous fat and overlying skin to draw a tissue segment into the cup for treatment. If the contour does not fit the body of the subject 11, then the approximately air-tight seal may not be achieved and the vacuum pressure is not established in the interior cavity 96 or 1096 to draw tissue into the applicator 15 or 1015 for treatment. An approximately air-tight seal may also be created by applying force to press the applicator 15 or 1015 into the soft tissue; however, the vacuum pressure therefore acts on subcutaneous fat and overlying skin that is under compression by the lips 144 and 1144. Accordingly, less tissue/fat may be drawn into the applicator 15 or 1015 for treatment. Additionally, movement by the subject 11 during the course of treatment may sufficiently increase tension of the skin 70 in the treatment area to pull the skin 70 away from the applicator 15 or 1015. As a result, the applicator 15 or 1015 may lose the approximately air-tight seal with the skin 70, lose the vacuum pressure drawing tissue into the interior cavity 96 or 1096 for treatment, and cause the applicator 15 or 1015 to separate from the body of the subject 11.

The inventors of the present disclosure have derived various contours suitable for treatments of a variety of lipid-rich cell deposits that may be naturally found on the human body. Accordingly, particular contours may be fitted to individual lipid-rich cell deposits to achieve an approximately air-tight seal, achieve the vacuum pressure for drawing tissue into an interior cavity for treatment, and use little or no force to maintain contact between an applicator and a patient. Such an approach may, however, become impractical because of the large number of unique shapes, their cost, and their storage. Embodiments of applicators according to the present disclosure include a firm or approximately rigid cup and one or more flexible or approximately rigid contour elements that may be attached and detached with respect to the cup. Attaching one or more contour elements to an edge of a cup cavity creates a specific contour to approximately fit a tissue segment to be treated. The contour elements can be attached and detached in a plurality of combinations to achieve a desired contour for a treatment. Accordingly, a single applicator including a cup, rigid cooling panels, a vacuum port, control housing and/or umbilical cable may be combined with a set of interchangeable contour elements to form a wide variety of contours for treating different lipid-rich cell deposits in a cost effective manner. Further, a practitioner performing the treatment can demonstrate their expertise to the patient by tailoring the applicator contour to the specific body parts being treated for lipid-rich cell removal. In this manner, the patient understands that their treatment is customized to their body for better comfort and for better treatment results.

Embodiments of some applicators according to the present disclosure include single element attachment systems, two element attachment systems, or attachment systems for any number of contour elements to create a desired applicator contour. The interfaces between cup cavity edges and contour elements cooperate to achieve the approximately air tight seal and achieve the vacuum pressure for drawing tissue into an interior of the cup cavity for treatment. It is desirable for these approximately air tight seals to be sufficiently robust to withstand contour element flex during a vacuum pressure treatment, tissue massage, gravity and patient movement.

Embodiments of some applicators according to the present disclosure may include registers to assure proper positioning of a contour element and/or detectors to determine placement of a contour element. Examples of registers and detectors include mechanical interlocks, magnets, electrical sensors, radio frequency transmitters and receivers, optical sensors, etc. According to some embodiments of the present disclosure, registers and/or detectors may be used to ensure that an applicator can operate only with some form of contour element attached in place. Alternatively, a cup may be configured for an applicator to operate without a contour element attached in place, thereby reducing the need, complexity, and cost associated with including contour element registers or contour element detectors.

Embodiments of some applicators according to the present disclosure include flexible contours that may adjust to allow adaptation to a patient's body while the applicator is applied to the body. In some embodiments, the flexible contour may be adjustable until a steady state condition is achieved, e.g., when tissue is drawn into the cup for treatment. Accordion ribbing and a single piece of material including relatively flexible portions are two examples of a flexible contour. Another example of a flexible contour may include composite parts having different durometers or flexibilities that provide greater strength and rigidity to counter stresses encountered during a treatment while allowing a softer, more flexible contour edge to contact with the patient for greater comfort during the treatment.

Other embodiments of applicators according to the present disclosure include interchangeable cups having different contours. An entire cup could be removed from the applicator housing and replaced with another cup having a contour suitable for treating a lipid-rich cell deposit.

Figure 15A:
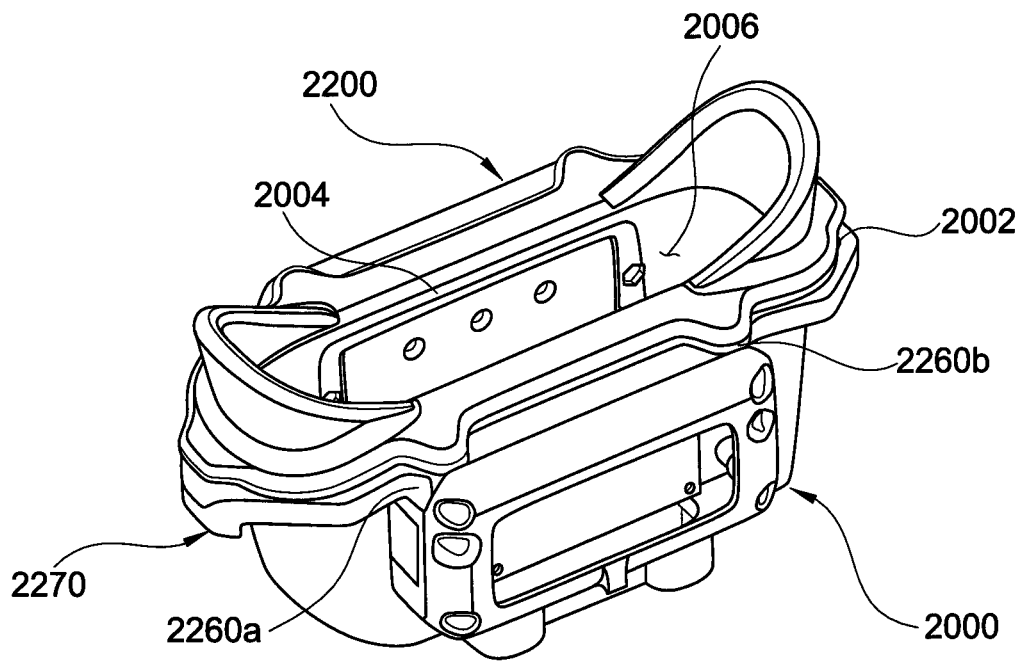
FIGS. 15A and 15B illustrate an embodiment of an applicator according to the present invention.
Figure 15B:
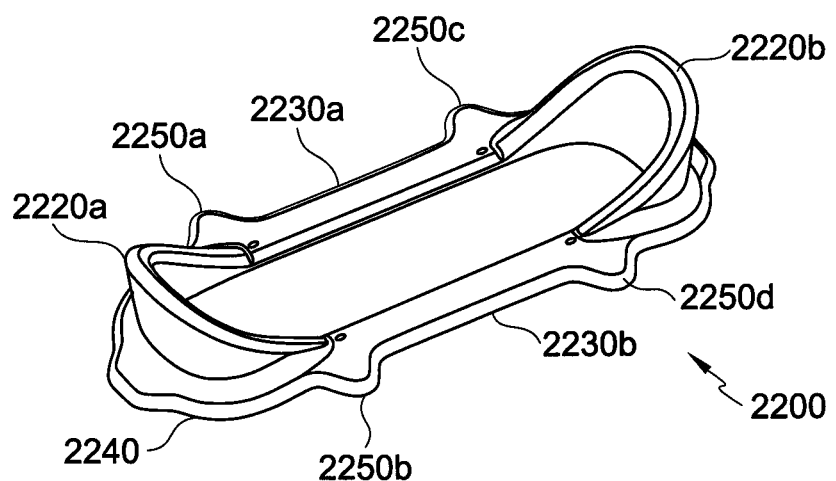

FIGS. 15A and 15B illustrate an embodiment of an applicator according to the present invention. In particular, FIG. 15A shows an example of a single piece contour element 2200 that is magnetically attached to a base 2000, and FIG. 15B shows the contour element 2200 detached therefrom. The magnetically attached contour element 2200 includes a single, integral unit that defines that entire contour. Accordingly, the contour element 2200 is magnetically attached and detached as an integral unit with respect to the base 2000 and is interchangeable with other magnetically attached contour elements providing the same or different contours. Other embodiments according to the present disclosure may include multiple-piece magnetically attached contour elements (not shown). Base 2000 can be generally rigid, e.g., may include a plurality of cooling surfaces as part of the cavity surface 96.

Each magnetically attached contour element 2200 may include lips 2220 (individual lips 2220a and 2220b are indicated) disposed at longitudinal ends and laterally spaced wings 2230 (individual wings 2230a and 2230b are indicated) extending between and coupling the lips 2220. The lips 2220 may provide portions of the contour that fit relatively curved body surfaces of a subject 11, and the wings 2230 may provide portions of the contour that fit relatively flat body surfaces of a subject 11. Wings 2230 may also provide a contour shape such that there is not a flat segment of the contour. The radius of curvature of the lips 2220, the distance that the lips 2220 project from the wings 2230, the lateral spacing between the wings 2230, the longitudinal length of the wings 2230, and any curvature of the wings 2230 define the suitability of a contour element 2200 to achieve an approximately air-tight seal for treating various size and shape areas of the subject 11. The contour element 2200 shown in FIGS. 15A and 15B includes a generally symmetrical contour; however, asymmetrical contours may also be provided by another contour element 2200.

The contour element 2200 also includes an attachment surface 2240 that is opposite the contour defined by the lips 2220 and the wings 2230. The attachment surface 2240 cooperatively engages a base surface 2002 on a cup edge 2004 cincturing an interior cavity 2006 of the base 2000. In the attached arrangement shown in FIG. 15A, the attachment surface 2240 sealingly engages the base surface 2002 for achieving a pressure vacuum in the interior cavity 2006 during a treatment. Each interchangeable contour element 2200 includes a similar attachment surface 2240 but may have a different contour as defined by the lips 2220 and the wings 2230 of an individual contour element 2200.

The wings 2230 are magnetically coupled to the cup edge 2004 of the base 2000 in the attached arrangement (FIG. 15A). In particular, the contour element 2200 includes first connectors 2250 that are magnetically attracted to second connectors 2260 of the base 2000. As shown in FIG. 15A, the wings 2230 may include first connectors 2250 (individual first connectors 2150a-2150d are indicated) that cooperatively mate with second connectors 2260 (individual second connectors 2260a and 2260b are indicated) on the base 2000. The first and second connectors 2250 and 2260 can include magnets and/or ferrous materials that are embedded in or lie proximate to the attachment surface 2240 or the base surface 2002 for aligning and releasably retaining the base 2000 and the contour element 2200 together in the attached arrangement (FIG. 15A) and permitting separation of the base 2000 from the contour element 2200 in the detached arrangement (FIG. 15B).

Figure 16A:
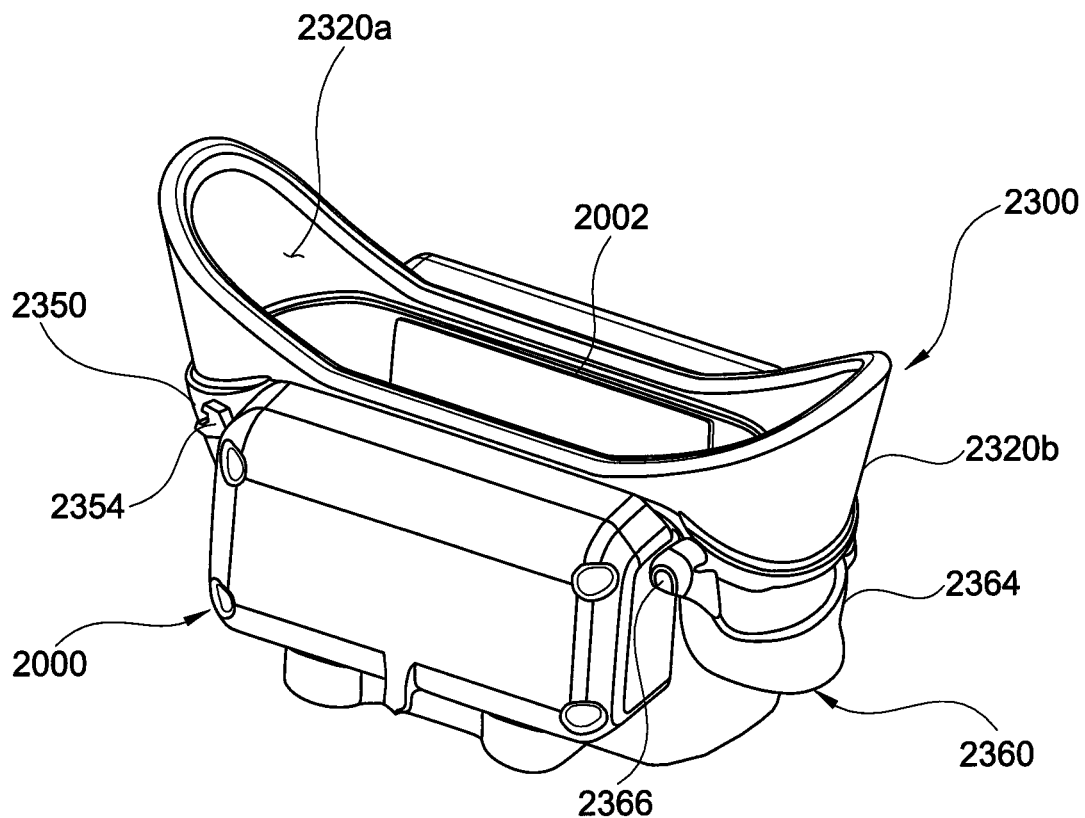
FIGS. 16A and 16B illustrate another embodiment of an applicator according to the present invention.
Figure 16B:
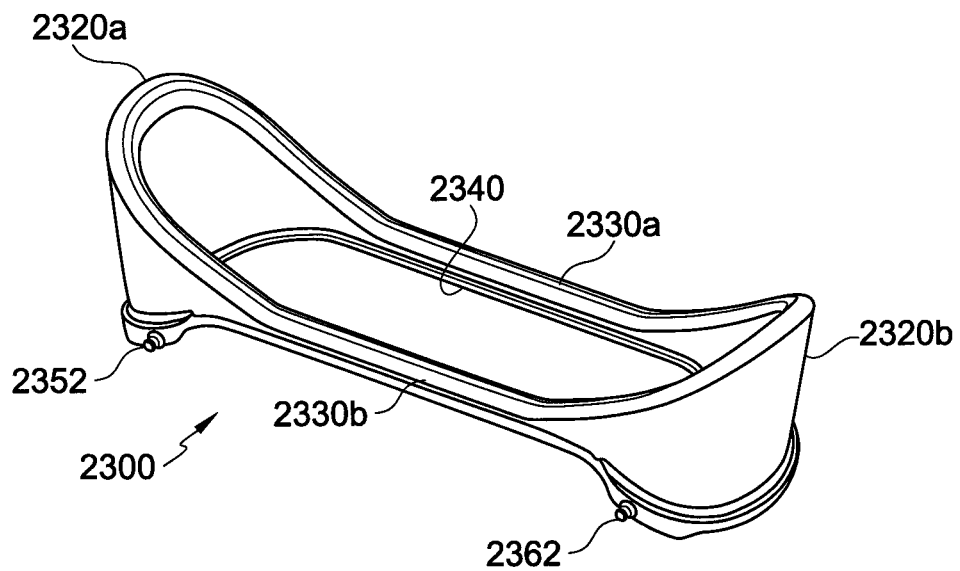

The magnetic attraction between the first and second connectors 2250 and 2260 make the base 2000 and the contour element 2200 self-aligning and self-locking to prevent or avoid unintended separation in the attached arrangement (FIG. 16A). Accordingly, the base 2000 may include an unlocking feature 2270 to permit intended separation in the detached arrangement (FIG. 16B). One embodiment of the unlocking feature 2270 according to the present disclosure includes a release 2010 that is relatively movable with respect to the base 2000 for shuttling the second connectors 2260 to an unlocking position that breaks the magnetic fields between the first and second connectors 2250 and 2260, which accordingly permits separation between the base 2000 and the contour element 2200. A single release 2010 may concurrently enable plural unlocking features 2270, individual releases 2010 may independently disable corresponding unlocking features 2270, or a combination thereof may be used for permitting separation between the base 2000 and the contour element 2200.

FIGS. 16A and 16B illustrate another embodiment of an applicator according to the present invention. In particular, FIG. 16A shows an example of a contour element 2300 attached to the base 2000, and FIG. 16B shows the contour element 2300 detached therefrom. The contour element 2300 may include a single, integral unit that defines that entire contour. Accordingly, the contour element 2300 is attached and detached as an integral unit with respect to the base 2000 and is interchangeable with other contour elements providing the same or different contours. Other embodiments according to the present disclosure may include multiple pieces magnetically attached contour elements (not shown).

The contour elements 2300 may include lips 2320 (individual lips 2320a and 2320b are indicated), wings 2330 (individual wings 2330a and 2330b are indicated), and an attachment surface 2340 that are similar to the lips 2120, wings 2130 and attachment surface 2140 described with respect to FIGS. 15A and 15B. In contrast to the contour element 2200, the base 2000 and the contour element 2300 include a toe clip 2350 and a heel lock 2360 disposed at opposite longitudinal ends of the contour element 2300.

The toe clip 2350 includes at least one first projection 2352 that is cooperatively received in a pivot slot 2354 in the attached arrangement (FIG. 16A). According to the embodiment shown in FIGS. 16A and 16B, the toe clip 2350 includes a pair of the first projections 2352 (only one is indicated in FIG. 16A) that extend laterally from the contour element 2300 and a pair of the pivot slots 2354 (only one is indicated in FIGS. 16A and 16B) that are disposed on opposite lateral sides of the base 2000. The first projections 2352 may be located generally proximate to the juncture between the lips 2320 and the wings 2330 to ensure a seal in that vicinity between the attachment surface 2340 and the base surface 2002. Other embodiments according to the present disclosure may include a single first projection 2352 located at a longitudinal end of the contour element 2300 and cooperatively received in a single pivot slot 2354 located at a longitudinal end of the base 2000.

The heel lock 2360 includes at least one second projection 2362 that cooperatively engages at least one swing arm 2364 in the attached arrangement (FIG. 16A). According to the embodiment shown in FIGS. 16A and 16B, the heel lock 2360 includes a pair of the second projections 2362 (only one is indicated in FIG. 16B) that extend laterally from the contour element 2300 and a bifurcated swing arm 2364 pivotally coupled to opposite lateral sides of the base 2000. The second projections 2362 may be located generally proximate to the juncture between the lips 2320 and the wings 2330 to ensure a seal in that vicinity between the attachment and base surfaces 2340 and 2002. The swing arm 2364 includes individual cam(s) 2366 that cooperatively engage a corresponding second projection(s) 2363 in the attached arrangement (FIG. 16A).

Attaching the contour element 2300 to the base 2000 includes engaging the first projection(s) 2352 and the pivot slot(s) 2354 of the toe clip 2350 while the attachment surface 2340 is oriented at an acute angle with respect to the base surface 2002. The contour element 2300 and the base 2000 are then pivoted toward each other until the attachment and base surfaces 2340 and 2002 engage one another for forming the approximately air-tight seal cincturing the interior cavity 2006 of the base 2000. The heel lock 2360 is then applied by pivoting the swing arm 2364 with respect to the base 2000 so that the cam(s) 2366 swing into contiguous engagement with the second projection(s) 2362. Continuing to pivot the swing arm 2364 to its locked position (FIG. 16A) causes the cam(s) 2366 to act on the second projection(s) 2362 to compress the contour element 2300 against the base 2000 so as to achieve the approximately air-tight seal cincturing the interior cavity 2006 of the base 2000. Detaching the contour element 2300 from the base 2000 may be accomplished by reversing the attaching process.

The base 2000 and the contour element 2300 may include a locking feature to prevent or avoid unintended separation in the attached arrangement (FIG. 16A). One embodiment of the locking feature according to the present disclosure includes pivoting the swing arm 2364 in an overcenter manner to its locked position (FIG. 16A).

Attaching the base 2000 and the contour element 2300 may provide a non-visual sense of positive engagement. Examples of devices that may provide a sense of positive engagement (or disengagement) can include an overcenter mechanism disposed between the base 2000 and the contour element 2100 to provide a tactile sense, a click stop to provide an audible sense, or requiring a greater force during attachment than during detachment to also provide a tactile sense.

Figure 17A:
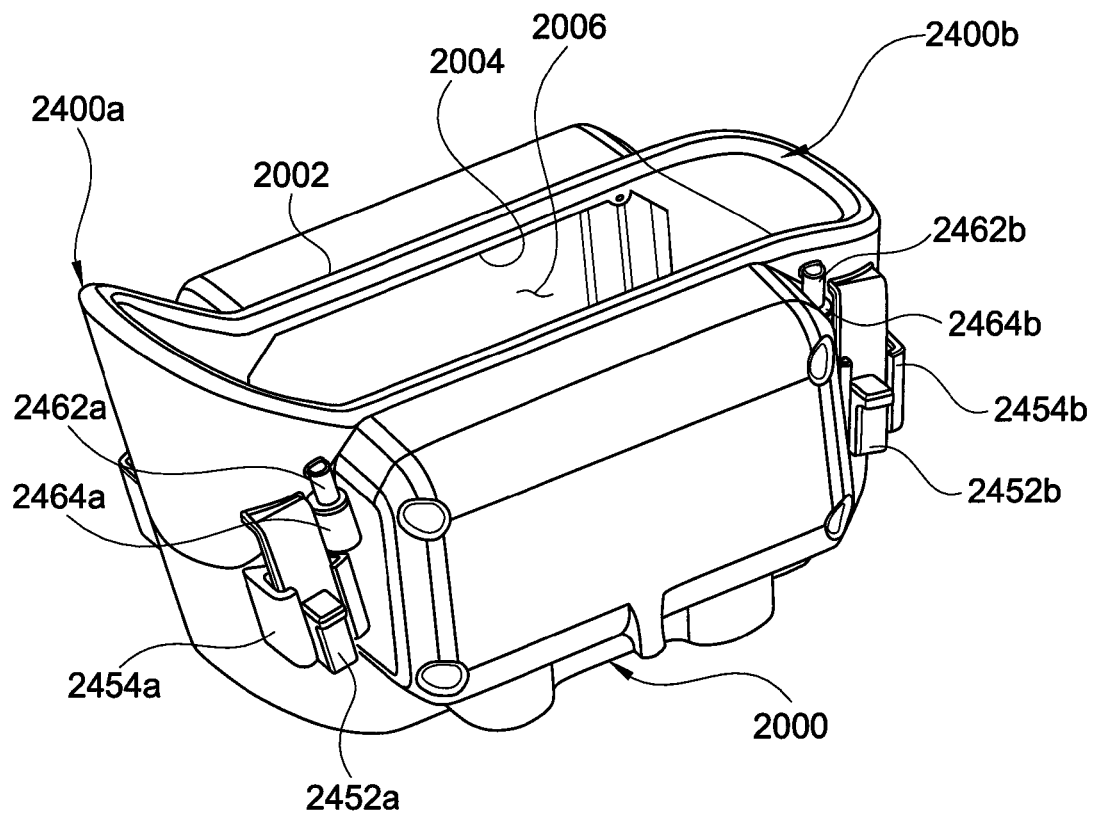
FIGS. 17A and 17B illustrate yet another embodiment of an applicator according to the present invention.
Figure 17B:
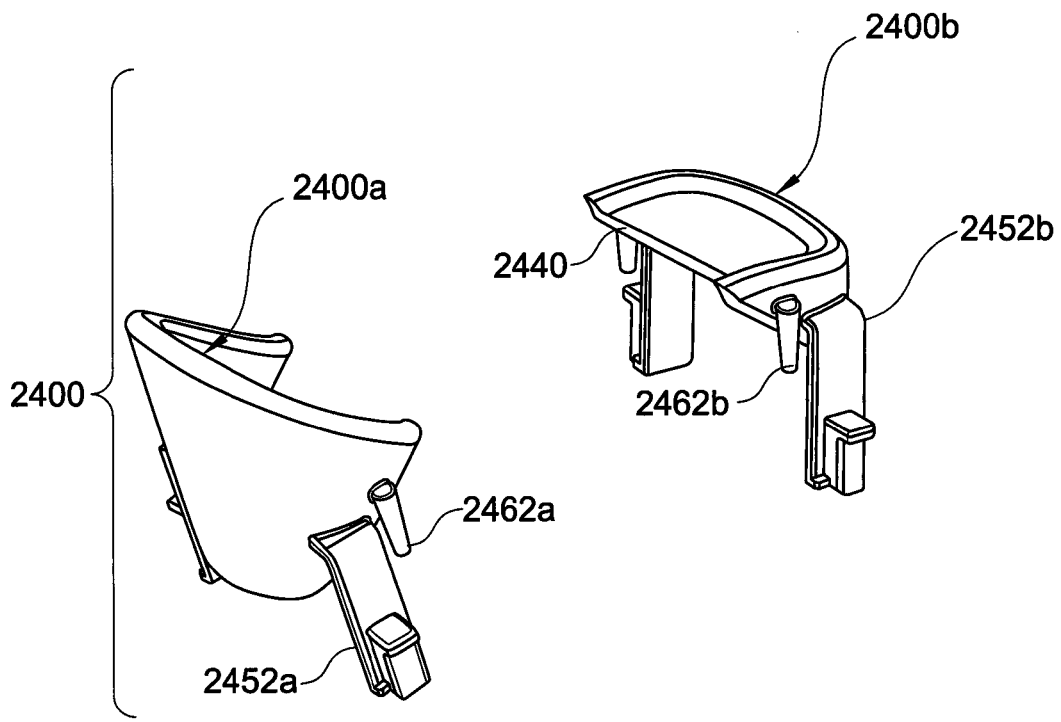

FIGS. 17A and 17B illustrate yet another embodiment of an applicator according to the present invention. In particular, FIG. 17A shows an example of a two-piece contour element 2400 attached to the base 2000, and FIG. 17B shows the two-piece contour element 2400 detached therefrom. The two-piece contour element 2400 includes two independent pieces 2400a and 2400b that partially define the contour. Each piece 2400a and 2400b is attached and detached independently with respect to the base 2000 and each piece is independently interchangeable with other two-piece contour elements to provide the same or different contours.

Each piece 2400a and 2400b provides a lip that is disposed at an opposite longitudinal end of the contour element 2400. In contrast to the magnetically attached contour element 2200 described with reference to FIGS. 15A and 15B, the base surface 2002 on the cup edge 2004 of the base 2000 provides the portions of the contour between the pieces 2400a and 2400b. The contour element 2400 shown in FIGS. 17A and 17B includes a generally asymmetrical contour; however, symmetrical contours may also be provided by using pieces 2400a and 2400b that have generally similar shapes and sizes.

Each piece 2400a and 2400b may include an attachment surface 2440 that cooperatively engages the base surface 2002 for providing an approximately air-tight seal to achieve a pressure vacuum in the interior cavity 2006 during a treatment. Each interchangeable piece of the contour element 2400 includes a similar attachment surface 2440 and still defines portions of different contours.

The base 2000 and the contour element 2400 may include a locking feature 2450 to prevent or avoid unintended separation in the attached arrangement (FIG. 17A) and to permit intended separation in the detached arrangement (FIG. 17B). One embodiment of the locking feature 2450 according to the present disclosure includes at least one resiliently deformable snap arm 2452 that is cooperatively received by a snap pocket 2544 in the attached arrangement (FIG. 17A). The embodiment shown in FIG. 17A shows a pair of the snap arms 2452 (individual snap arms 2452a and 2452b are indicated) for each piece 2400a or 2400b, and corresponding pairs of the snap pockets 2454 (individual snap pockets 2454a and 2454b are indicated) are provided on the base 2000.

The base 2000 and the contour element 2400 may also include an alignment feature 2460 to prevent or avoid unintended deformation of the contour in the attached arrangement (FIG. 17A), which could prevent achieving a pressure vacuum in the interior cavity 2006 during a treatment. One embodiment of the alignment feature 2460 according to the present disclosure includes at least one pin 2462 that is cooperatively received by a hole 2464 in the attached arrangement (FIG. 17A). The embodiment shown in FIG. 17A shows a pair of the pins 2462 (individual pins 2462a and 2462b are indicated) for each piece 2400a or 2400b, and corresponding pairs of the holes 2464 (individual holes 2464a and 2464b are indicated) are provided on the base 2000. The alignment feature 2460 may be located generally proximate to the juncture between tips of the contour elements 2400 and the base surface 2002 to ensure a seal in that vicinity between the attachment and base surfaces 2440 and 2002.

Attaching the contour element 2400 to the base 2000 includes aligning the pin(s) 2462 and the hole(s) 2464 while sliding the snap arm(s) 2452 into the snap pocket(s) 2454. Detaching the contour element 2400 from the base 2000 may be achieved by resiliently deforming the snap arm(s) 2452, e.g., pressing them toward one another, and sliding the contour element away from the applicator.

Embodiments according to the present disclosure may include other attachment devices and/or seals between an applicator and one or more contour elements. For example, the applicator and contour element may include cams, interlocking channel sections, elastic skirts, resilient straps, latches, and other attachments suitable for providing an at least approximately air-tight coupling that may be released to permit interchanging contour elements with respect to the applicator.

Embodiments according to the present disclosure may provide one or more additional advantages. For example, the size, shape and other physical properties of the panels and the frames may be selected to accommodate a standard heat removal source that may be used/reused with individual vacuum applicators. Accordingly, modifications to the flexible portion of individual vacuum applicators may enable the use of a standard heat removal source and accommodate different contours of individual cutaneous layers. In turn, this may make it possible to reuse the relatively expensive heat removal and suction sources, and to dispose of the relatively inexpensive personal protection devices and/or vacuum applicators for different treatments. The rigid portions of the vacuum applicators, which are relatively stiff with respect to the flexible portion, provide an attachment point for the heat removal sources that may resist bowing into the interior cavity and possibly separating from the heat removal sources when a partial vacuum is drawn in the vacuum applicators. The separator may allow the vacuum applicator to retain a thermal coupling fluid, e.g., a cryoprotectant gel including a temperature depressant, in the interior cavity and avoid passage of the fluid through the suction port in the event that the vacuum applicator is inverted. The cams and latches may press and hold the heat removal sources to the rigid portions and thereby facilitate reliable thermal conductivity between the interior cavity of the vacuum applicator and the heat removal source. Disposing the temperature sensors inside the vacuum applicators, e.g., on the patient protection devices, may more accurately measure the temperature of the cutaneous layer. The flexible section also allows some compliance to different subject 11 body contours or geometries.

From the foregoing, it will be appreciated that specific embodiments of the disclosure have been described herein for purposes of illustration, but that various modifications may be made without deviating from the disclosure. For example, structures and/or processes described in the context of particular embodiments may be combined or eliminated in other embodiments. In particular, the attachment features described above with reference to particular embodiments may include one or more additional features or components, or one or more of the features described above may be omitted. Moreover, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure may include other embodiments not shown or described above.

We claim:

1. A device for treating subcutaneous lipid-rich cells, comprising:
    a rigid portion including a thermal conductor having an inside surface and an outside surface positioned opposite the inside surface; and
    a flexible portion having an inner surface, an outer surface positioned opposite the inner surface, and a cutout extending between the inner and outer surfaces;
    wherein the thermal conductor is positioned in the cutout and the flexible and rigid portions define a body having—
        an interior surface including the inside face of the rigid portion and the inner surface of the flexible portion; and
        an exterior surface including the outside face of the rigid portion and the outer surface of the flexible portion.

2. The device of claim 1 wherein the rigid portion comprises:
    at least one thermoelectric cooling unit having a cold side in thermal contact with the thermal conductor and a hot side positioned opposite the cold side; and
    a heat exchanger in thermal contact with the hot side of the thermoelectric cooling unit.

3. The device of claim 2, further comprising a frame coupling the rigid and flexible portions.

4. The device of claim 1 wherein the rigid portion comprises a heat exchanger in thermal contact with the thermal conductor, the heat exchanger includes a passage configured to circulate a heat exchange fluid.

5. The device of claim 1 wherein the inside surface of the thermal conductor comprises a printed circuit.

6. The device of claim 5 wherein the printed circuit includes a first measurement sensor and the thermal conductor includes a first recess receiving the first measurement sensor.

7. The device of claim 5 wherein the printed circuit comprises a first measurement sensor and a second measurement sensor is positioned in a second recess on the outside surface of the thermal conductor.

8. The device of claim 6 or claim 7 wherein the measurement sensors comprise at least one of a temperature sensor and a heat flux sensor.

9. The device of claim 6 or claim 7 wherein the measurement sensors are configured to provide differential measurement signals.

10. The device of claim 1, further comprising:
    a housing coupled to the flexible portion, the housing includes a receptacle having a first electric contact; and
    a token configured to interface with the receptacle, the token including—
        a second contact configured to electrically couple with the first electric contact;
        a microelectronic device electrically coupled with the second contact; and
        an enclosure configured to support the second electric contact and the microelectronic device and to cooperatively engage the receptacle.

11. The device of claim 10, further comprising a measurement sensor positioned on the inside surface of the thermal conductor.

12. The device of claim 11 wherein the measurement sensor electrically communicates via the first electric contact.

13. The device of claim 11 wherein the inside surface of the thermal conductor comprises a printed circuit electrically coupled to the measurement sensor.

14. The device of claim 11 or claim 13 wherein the measurement sensor comprises at least one of a temperature sensor and a heat flux sensor.

15. The device of claim 11, further comprising a plurality of the measurement sensors configured to provide differential measurement signals.

16. The device of claim 10 wherein the receptacle and the enclosure include corresponding asymmetrical features that are cooperatively engaged when the token interfaces with the receptacle.

17. The device of claim 10 wherein the first and second electrical contacts include corresponding asymmetrical features that are cooperatively engaged when the token interfaces with the receptacle.

18. The device of claim 1, further comprising a barrier overlying at least the interior surface of the body.

19. The device of claim 18 wherein the barrier comprises a barrier configured to be disposed between patients.

20. The device of claim 18 wherein the barrier overlies the exterior surface of the body.

21. The device of claim 18 wherein the body includes a magnet and the barrier includes a ferrous material configured to cooperatively engage the magnet.

22. The device of claim 18 wherein the barrier comprises:
    a liner including a thin gauge film; and
    a frame including a frame material that is relatively stiff compared to the thin gauge film, the frame being coupled to the liner and configured to hold the liner taut over the inside surface of the thermal conductor.

23. The device of claim 18 wherein the barrier comprises a selectively permeable membrane coupled to the liner, the member is configured to allow air to pass when drawing a vacuum in the body and to restrict passage of a gel.

24. A system for treating subcutaneous lipid-rich cells in a target area, comprising:
- a treatment device including an applicator configured to operably engage the target area, the applicator including a heat removal source configured to remove heat from the lipid-rich cells; and
- a token permitting a treatment with the treatment device, the token including a microelectronic device electrically coupled with the heat removal source.

25. The system of claim 24, wherein the token interfaces with the treatment device.

26. The system of claim 25, further comprising an asymmetric interface coupling the treatment device and the token.

27. The system of claim 24 wherein the token comprises an asymmetric interface.

28. The system of claim 27 wherein the asymmetric interface comprises asymmetrical male and female members and the asymmetrical female member receives the asymmetrical male member while the token permits a treatment with the treatment device.

29. The system of claim 24, further comprising a liner configured to be positioned between the treatment device and the target area.

30. The system of claim 29 wherein the liner is configured to be disposed between patients and the treatment device is configured to be used for more than one treatment.

31. The system of claim 29 wherein the liner includes a thin gauge film and a ferrous material operably coupled to the film, and wherein the treatment device includes a magnet configured to magnetically couple with the ferrous material.

32. The system of claim 29 wherein a microelectronic device determines when the liner is positioned with respect to the treatment device.

* * * * *